(12) United States Patent
Goh et al.

(10) Patent No.: US 10,925,737 B2
(45) Date of Patent: Feb. 23, 2021

(54) MANDIBLE ENDOPROSTHESIS IMPLANT, IMPLANT SYSTEM, SURGICAL KIT, AND METHODS FOR SURGICALLY REPAIRING A MANDIBLE

(71) Applicant: SINGAPORE HEALTH SERVICES PTE. LTD., Singapore (SG)

(72) Inventors: Bee Tin Goh, Singapore (SG); Yuchun Liu, Singapore (SG); Nattharee Chanchareonsook, Singapore (SG); Wei Yang Edwin Liu, Singapore (SG)

(73) Assignee: SINGAPORE HEALTH SERVICES PTE LTD., Singapore (SG)

( * ) Notice: Subject to any disclaimer, the term of this patent is extended or adjusted under 35 U.S.C. 154(b) by 191 days.

(21) Appl. No.: 16/084,501

(22) PCT Filed: Mar. 22, 2017

(86) PCT No.: PCT/SG2017/050139
§ 371 (c)(1),
(2) Date: Sep. 12, 2018

(87) PCT Pub. No.: WO2017/188892
PCT Pub. Date: Nov. 2, 2017

(65) Prior Publication Data
US 2019/0070006 A1 Mar. 7, 2019

(30) Foreign Application Priority Data

Mar. 22, 2016 (SG) .............................. 10201602227S

(51) Int. Cl.
*A61F 2/28* (2006.01)
*A61F 2/46* (2006.01)
*A61F 2/30* (2006.01)

(52) U.S. Cl.
CPC .......... *A61F 2/2803* (2013.01); *A61F 2/4601* (2013.01); *A61F 2002/3085* (2013.01);
(Continued)

(58) Field of Classification Search
CPC ...................... A61F 2/28; A61F 2/2803; A61F 2002/30395; A61F 2002/30538; A61F 2002/30578; A61F 17/8071
(Continued)

(56) References Cited

U.S. PATENT DOCUMENTS 3,488,779 A 1/1970 Christensen
3,720,959 A 3/1973 Hahn
(Continued)

FOREIGN PATENT DOCUMENTS

CN 101808589 A 8/2010
WO 0205728 A2 1/2002
WO WO2007061382 A1 5/2007

OTHER PUBLICATIONS

Balaji, S.M., "Failed Bone Graft for Lower Jaw Treated Elsewhere Constructed Successfully with rhBMP-2", "http://blog.smbalaji.com/surgery-of-the-week/failed-bone-graft-for-lower-jaw-treated-elsewhere-reconstructed-successfully-with-rhbmp-2", Mar. 26, 2014.
Chanchareonsook, H., et al., "Mandibular Reconstruction With a Bioactive-Coated Cementless Ti6A14V Modular Endoprosthesis in Macaca Fascicularis", "Int. J. Oral Maxillofac. Surg.", 2014, pp. 758-768, vol. 43.
(Continued)

*Primary Examiner* — Bruce E Snow
(74) *Attorney, Agent, or Firm* — Hultquist, PLLC; Steven J. Hultquist

(57) ABSTRACT

Mandible endoprosthesis implant and mandible endoprosthesis implant system and surgical kit comprising the same, the mandible endoprosthesis implant comprising: first end second implant elements which can be coupled in a manner so as to allow a relative pivotal movement therebetween. The present disclosure further provides methods for surgically repairing a mandible.

18 Claims, 46 Drawing Sheets

(52) U.S. Cl.
CPC ............... *A61F 2002/30387* (2013.01); *A61F 2002/30507* (2013.01); *A61F 2002/30538* (2013.01); *A61F 2002/30578* (2013.01); *A61F 2002/30873* (2013.01); *A61F 2002/4688* (2013.01)

(58) Field of Classification Search
USPC ...................................................... 623/17.17
See application file for complete search history.

(56) References Cited

U.S. PATENT DOCUMENTS

| | | |
|---|---|---|
| 5,554,194 A | 9/1996 | Sanders |
| 5,975,904 A | 11/1999 | Spiegel |
| 6,060,641 A | 5/2000 | Manolidis |
| 6,423,068 B1 | 7/2002 | Reisberg et al. |
| 7,704,251 B2 | 4/2010 | Huebner et al. |
| 2003/0108845 A1 | 6/2003 | Giovannone et al. |
| 2007/0276405 A1 | 11/2007 | Huebner et al. |
| 2008/0228278 A1 | 9/2008 | Lee et al. |
| 2013/0041469 A1 | 2/2013 | Phelps |
| 2015/0018829 A1 | 1/2015 | Woodburn et al. |

OTHER PUBLICATIONS

Ebraheim, N.A., et al, "Bone-Graft Harvesting From Iliac and Fibular Donor Sites: Techniques and Complications", "J. Am. Acad. Orthop. Surg.", 2001, pp. 210-218, vol. 9.

Gonzalez-Garcia, R., et al., "Vascularized Fibular Flap for Reconstruction of the Condyle After Mandibular Ablation", "J Oral Maxillofac Surg", 2008, pp. 1133-1137, vol. 66.

Hidalgo, D.A., et al., "A Review of 60 Consecutive Fibula Free Flap Mandible Reconstructions", "Plastic and Reconstructive Surgery", 1995, pp. 585-596, vol. 96.

Holzle, F., et al., "Reconstructive Oral and Maxillofacial Surgery", "Dtsch Arztebl Int", 2008, pp. 815-822, vol. 105, No. 47.

Lee, S., et al., "Modular Endoprosthesis for Mandibular Body Reconstruction: A Clinical, Micro-CT and Histologic Evaluation in Eight Macaca Fascicularis", "Int. J. Oral Maxillofac. Surg.", 2009, pp. 40-47, vol. 38.

Shpitzer, T., et al., "Leg Morbidity and Function Following Fibular Free Flap Harvest", "Ann Plast Surg", 1997, pp. 460-464, vol. 38.

Wong, R., et al., "The Modular Endoprosthesis for Mandibular Body Replacement. Part 2: Finite Element Analysis of Endoprosthesis Reconstruction of the Mandible", "Journal of Cranio-Maxillo-Facial Surgery", 2012, pp. e487-e497, vol. 40.

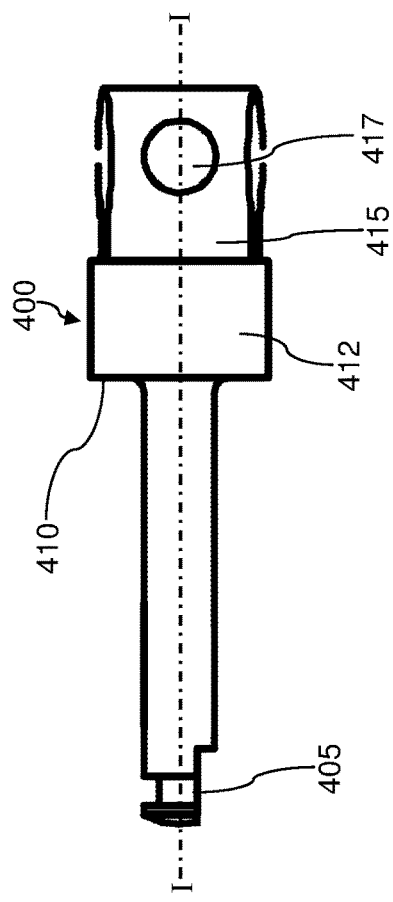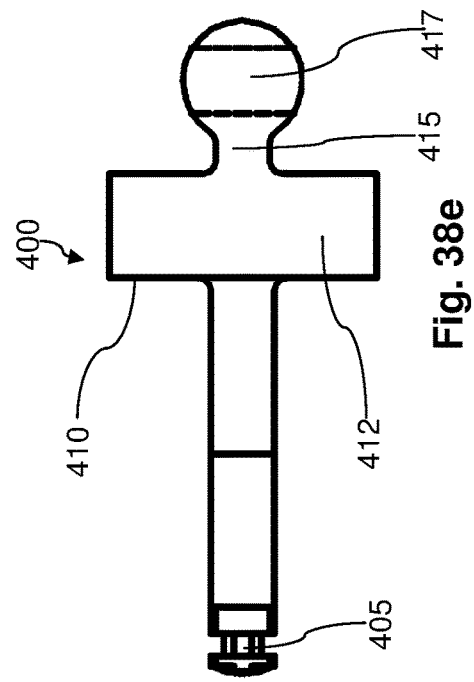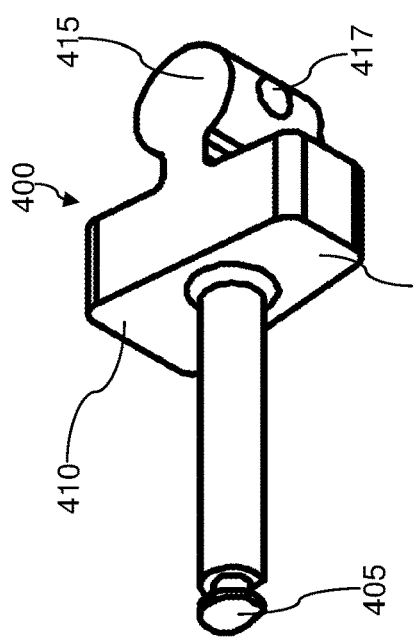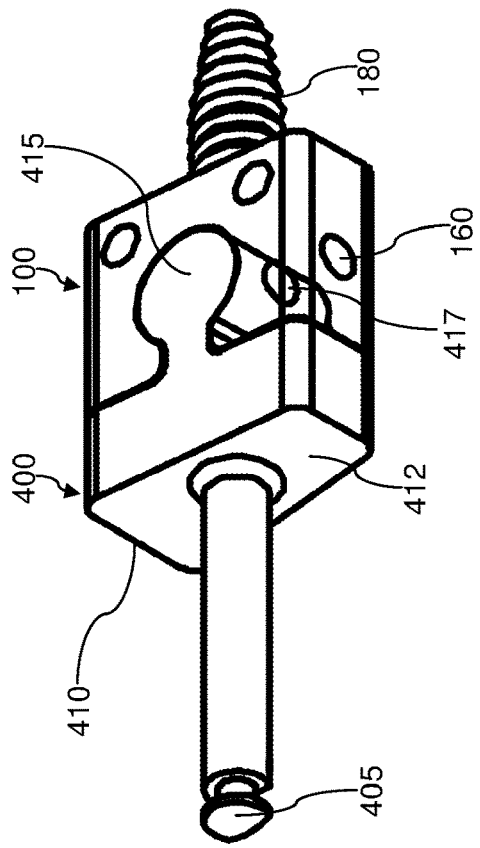

MANDIBLE ENDOPROSTHESIS IMPLANT, IMPLANT SYSTEM, SURGICAL KIT, AND METHODS FOR SURGICALLY REPAIRING A MANDIBLE

CROSS-REFERENCE TO RELATED APPLICATIONS

This is a U.S. national phase under the provisions of 35 U.S.C. § 371 of International Patent Application No. PCT/SG17/50139 filed Mar. 22, 2017, which in turn claims priority of Singapore Patent Application No. 10201602227S filed Mar. 22, 2016. The disclosures of such international patent application and Singapore priority patent application are hereby incorporated herein by reference in their respective entireties, for all purposes.

TECHNICAL FIELD

Various aspects of this disclosure relate to a mandible endoprosthesis implant having a first implant element and a second implant element that are movable relatively to each other and a mandible endoprosthesis implant system including said mandible endoprosthesis implant and relate to a mandible endoprosthesis implant system as well as a surgical kit which comprise the mandible endoprosthesis implant and methods for surgically repairing a human's mandible by use of the mandible endoprosthesis implant according to the invention.

BACKGROUND

Mandibular defects may result from trauma, inflammatory diseases or upon resection of tumors and so.

One possible surgical approach for mandible reconstruction is the microvascular fibula free flap strategy in which a fibula flap is harvested from a donor site, modeled according to the mandible portion to be replaced and finally fixated to the mandibular bone stumps by small plates and a plurality of screws. However, this surgical procedure is time-consuming since it involves two surgeries, one at the secondary donor site and the other at the mandible defect. Further, the integrity of the vessels also needs to be evaluated through various medical imaging modalities to be deemed suitable for use prior to the grafting procedure. There may also be complications at the donor site, such as infection, pain, sensory loss, acute compartment syndrome, ankle instability, and so on. Therefore, the microvascular fibula free flap strategy usually requires a hospitalization stay of several weeks, adding to costs. Patients who undergo the microvascular fibula free flap strategy will also usually need to undergo a period of rehabilitation before returning to pre-operative status of ambulation. Furthermore, elderly or medically compromised patients may not be able to withstand the long surgery durations of this surgical procedure.

As another approach, mandible implants, such as metallic reconstruction plates, may be used to bridge a mandibular defect. Implants are, for example, known from U.S. Pat. No. 6,060,641, from U.S. Pat. No. 6,423,068, and from US Patent Application No. 2008/0228278.

Despite significant efforts made to improve methods and devices in mandible reconstruction, challenges remain and it would be desirable to provide a commercially available implant intended for use in the mandible to restore form and function during mandibular reconstruction and restore patients' quality of life after surgery. It would also be desirable that an implant may be easily adaptable to the exact size of the mandibular defect and that the required surgery can be performed in a shorter duration and without the need for harvesting a patient's own tissue. Further, it would be also desirable that the duration of the post-operative hospitalization and the associated costs could be reduced.

SUMMARY

The present invention seeks to provide an improved mandible endoprosthesis implant which is able to address or alleviate the abovementioned issues.

Accordingly, various aspects of this disclosure provide a mandible endoprosthesis implant and provide mandible endoprosthesis systems, a surgical kit and methods for surgically repairing a human's mandible, which comprise and/or use the mandible endoprosthesis implant according to various aspects of this disclosure. The mandible endoprosthesis implant according to various aspects of this disclosure comprises a first implant element which extends along a first element x-axis and which includes first coupling portion. The first coupling portion comprises an accommodation recess which extends along the first element x-axis, and a first insertion hole which extends along a first element z-axis transverse to the first element x-axis. The mandible endoprosthesis implant further comprises a second implant element which extends along a second element x-axis and which includes a second coupling portion. The second coupling portion comprises a protrusion which extends along the second element x-axis, and a second insertion hole which extends through the protrusion along a second element z-axis transverse to the second element x-axis. The protrusion and the accommodation recess are engageable with each other such that the first and second insertion holes are at least substantially aligned with each other, thereby establishing a coupled condition between the first and second implant elements. The mandible endoprosthesis implant further comprises a fastener which, when the protrusion and the accommodation recess are engaged with each other to have the first and second insertion holes at least substantially aligned with each other, is engageable into both the first and second insertion holes so as to extend along the first element z-axis and so as to maintain a coupled condition of the first and second implant elements, and which is fixedly attachable to the first coupling portion (in connection with engaging the first and second insertions holes). When the first and second implant elements are in their coupled condition and when the fastener is fixedly attached to the first coupling portion, there is provided a first abutment clearance between the first coupling portion and the second coupling portion and there is provided a second abutment clearance between the fastener and the second coupling portion. The first and second abutment clearances are provided such that the first and second implant elements are pivotable relatively to each other about at least one of the first element z-axis and a first element y-axis, which extends transverse to the first element x- and z-axes, by a maximum angle in a range from 0.01 to 10°, optionally from 0.01 to 7°.

BRIEF DESCRIPTION OF THE DRAWINGS

The invention will be better understood with reference to the detailed description when considered in conjunction with the non-limiting embodiments and drawings. In the drawings:

FIG. 28b is a perspective view of the second implant element, which is formed in one piece with the further second implant element, of FIG. 28a.

FIG. 29 is a top view of the second implant element, which is formed in one piece with the further second implant element, of FIG. 28a;

FIG. 38b is a perspective view of the first implant element mount according to the first embodiment;

FIG. 38c is a perspective view illustrating a coupled condition of the first implant element mount according to the first embodiment and the first implant element of the present invention;

FIG. 38d is a top view of the first implant element mount according to the first embodiment;

FIG. 38e is a cross-sectional view along line I-I of FIG. 38d;

FIG. 40b is a perspective view of a first surgical guide of FIG. 40a;

FIG. 41b is a perspective view of a second surgical guide of FIG. 40a;

Figure 1:
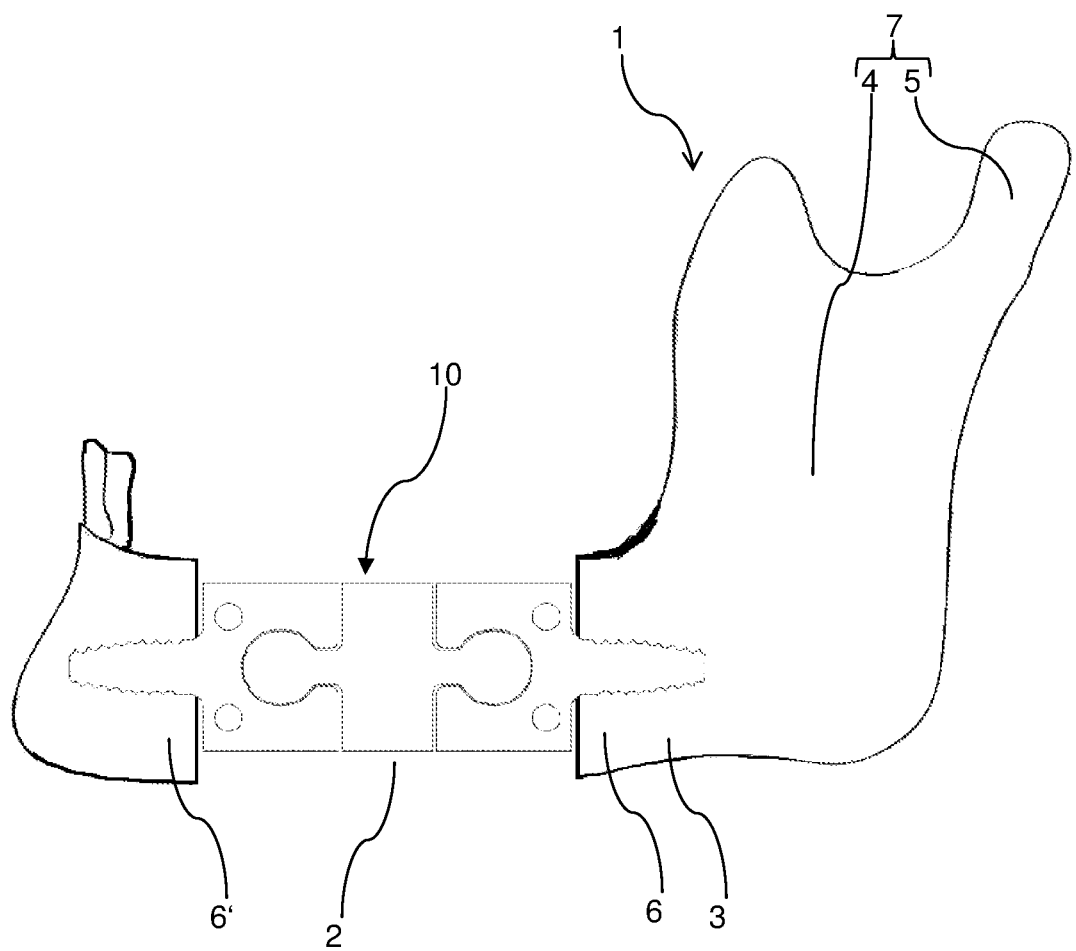
FIG. 1 is a side view of a human's mandible, illustrating a state in which a mandible endoprosthesis implant according to a first embodiment of the present invention is implanted to bridge a resected portion of the mandible body.

It should be understood that the appended drawings are not necessarily to scale, presenting a somewhat simplified representation of various preferred features illustrative of the basic principles of the disclosure. The specific design features of the present disclosure as disclosed herein, including, for example, specific dimensions, orientations, locations, and shapes, will be determined in part by the particular intended application and use environment. The first and second implant elements according to the diverse embodiments as described herein can be applied as first and second implant elements of the diverse embodiments of the mandible endoprosthesis implant and of the mandible endoprosthesis implant system as described herein.

DETAILED DESCRIPTION

The following detailed description refers to the accompanying drawings which show, by way of illustration, specific details and embodiments in which the invention may be practiced. Throughout the description and drawings, reference numbers refer to the same or equivalent parts of the present disclosure.

The word "exemplary" is used herein to mean "serving as an example, instance, or illustration". Any embodiment or design described herein as "exemplary" is not necessarily to be construed as preferred or advantageous over other embodiments or designs.

With regard to the terms "at least substantially aligned" and "at least substantially parallel" as used herein in connection to with elements/parts which experience/can experience an intended relative pivotal movement relative to each other, these terms are to be understood to also include deviations from a perfectly aligned condition and a perfectly parallel condition, e.g. deviations up to the maximum angle (0.01 to 10° (e.g., + usual tolerances)) resulting from the intended possibility of relative pivoting of the first element relative to the second implant element in the coupled condition thereof about at least one of the second and third element axes as described herein. Otherwise, the term "at least substantially", e.g., merely includes usual (manufacturing) tolerances.

According to the diverse embodiments of the invention as can be derived from the attached figures, the invention provides a mandibular endoprosthesis implant (as for example implemented as mandible endoprosthesis implants 10 and 15 shown in FIGS. 1 to 11).

The mandible endoprosthesis implant according to the diverse embodiments comprises a first implant element 100 which extends along a first element x-axis X1. The first implant element 100 includes a first coupling portion 120 comprising an accommodation recess 140 which extends along the first element x-axis X1, and comprising a first insertion hole 160 which extends along a first element z-axis Z1 transverse to the first element x-axis X1.

The mandible endoprosthesis implant also comprises a second implant element 200 which extends along a second element x-axis X2. The second implant element 200 includes a second coupling portion 220 comprising a protrusion 240 which extends along the second element x-axis X2, and comprising a second insertion hole 260 which extends through the protrusion 240 along a second element z-axis transverse to the second element x-axis X2. The protrusion 240 and the accommodation recess 140 are engageable with each other such that the first and second insertion holes 160 and 260 are at least substantially aligned with each other, thereby establishing a coupled condition between the first and second implant elements 100 and 200.

The mandible endoprosthesis implant also comprises a fastener 300 which, when the protrusion 240 and the accommodation recess 140 are engaged with each other to have the first and second insertion holes 160 and 260 at least substantially aligned with each other, is engageable into both the first and second insertion holes 160 and 260 so as to extend along the first element z-axis Z1 and in order to maintain a coupled condition of the first and second implant elements 100 and 200, and which is fixedly attachable to the first coupling portion 120 (when being engaged with (and/or inserted into) the first 160 and second inserted holes 260).

When the first and second implant elements 100 and 200 are in their coupled condition and when the fastener 300 is fixedly attached to the first coupling portion 120, there is provided a first abutment clearance C1 between the first coupling portion 120 and the second coupling portion 220 and there is provided a second abutment clearance C2 between the fastener 300 and the second coupling portion 220, and the first and second abutment clearances C1 and C2 are provided such that the first and second implant elements 100 and 200 are pivotable relatively to each other (e.g. from abutment to abutment) about at least one of the first element z-axis Z1 and a first element y-axis Y1, which extends transverse to the first element x- and z-axes X1 and Z1, by a maximum angle in a range from 0.01 (optionally from 0.02) to 10°, optionally from 0.01 (optionally from 0.02) to 7°, further optionally from 0.01 (optionally from 0.02) to 1°. The relative pivoting between the first and second implant elements 100 and 200 about at least one of the first element z-axis Z1 and a first element y-axis Y1 may be a relative movement between first and second implant elements 100 and 200 from a first position, in which the first element x-axis X1 and the second element x-axis X2 are perfectly aligned with each other, to a second position, in which the first element x-axis X1 and the second element x-axis X2 are pivoted relatively to each other (e.g. form an angle between each other).

Since only a small maximum angle of relative pivoting is allowed, when the mandible endoprosthesis implant is assembled and implanted, the implant can be continuously used even without finally fixing the first and second implant elements 100 and 200 such that they are no longer movable relative to each other. Further, after implantation, a subsequent surgery for fixing the first and second implant elements 100 and 200 together is/can be avoided.

The first abutment clearance C1 may comprise a first abutment sub-clearance C1a provided between the protrusion 240 and the accommodation recess 140, and related to a relative pivoting between the first and second implant elements 100 and 200 about the first element z-axis Z1, a second abutment sub-clearance C1b provided between the protrusion 240 and the accommodation recess 140, and related to relative pivoting between the first and second implant elements 100 and 200 about the first element y-axis Y1, a third abutment sub-clearance C1c provided between a first end face 103, in which the accommodation recess 140 is provided, of the first coupling portion 120 and a corresponding second end face 203, from which the protrusion 240 extends, of the second coupling portion 220, and related to relative pivoting between the first and second implant elements 100 and 200 about the first element z-axis Z1, and a fourth abutment sub-clearance C1d provided between the first end face 103 of the first coupling portion 120 and the corresponding second end face 203 of the second coupling portion 220, and related to a relative pivoting between the first and second implant elements 100 and 200 about the first element y-axis Y1.

It is to be noted that a "sub-clearance provided between the protrusion and the accommodation recess" as described in this application is to be understood as a space (and/or distance) within the accommodation recess 140 between an inner wall (and/or inner wall portion) of the first coupling portion 120, said wall portion defining the accommodation recess 140, and an outer wall (and/or outer wall portion) of the first coupling portion 120, of the protrusion 240 of the second coupling portion 220.

At least one of the first abutment sub-clearance C1a and the third abutment sub-clearance C1c may be set so as to limit the relative pivoting between the first and second implant elements 100 and 200 about the first element z-axis Z1 to the maximum angle. For example, the first abutment sub-clearance C1a may be smaller than the third abutment sub-clearance C1c so that the protrusion 240 and the accommodation recess 140 abut against each other at the maximum angle so as to limit the relative pivoting between the first and second implant elements 100 and 200 about the first element z-axis Z1 to the maximum angle. In another example, the third abutment sub-clearance C1c may be smaller than the first abutment sub-clearance C1a so that the first end face 103 and the corresponding second end face 203 abut against each other at the maximum angle so as to limit the relative pivoting between the first and second implant elements 100 and 200 about the first element z-axis Z1 to the maximum angle (as for example also implemented in the embodiment shown in FIGS. 1 to 9).

Further, at least one of the second abutment sub-clearance C1b and the fourth abutment sub-clearance C1d may be set so as to limit the relative pivoting between the first and second implant elements 100 and 200 about the first element y-axis Y1 to the maximum angle. For example, the second abutment sub-clearance C1b may be smaller than the fourth abutment sub-clearance C1d and smaller than the second abutment clearance C2 so that the protrusion 240 and the accommodation recess 140 abut against each other at the maximum angle so as to limit the relative pivoting between the first and second implant elements 100 and 200 about the first element y-axis Y1 to the maximum angle. In another example, the fourth abutment sub-clearance C1d may be smaller than the second abutment sub-clearance C1b and smaller than the second abutment clearance C2 so that the first end face 103 and the corresponding second end face 203 abut against each other at the maximum angle so as to limit the relative pivoting between the first and second implant elements 100 and 200 about the first element y-axis Y1 to the maximum angle.

In another example, the second abutment clearance C2 may be set such that, during relative pivoting between the first element and second elements 100 and 200 about the first element y-axis Y1, the fastener 300 abuts against the protrusion 240 (e.g. against a peripheral surface 242 of the protrusion 240, the peripheral surface 242 defining the second insertion hole within the protrusion 240) at the maximum angle so as to limit the relative pivoting between the first and second implant elements 100 and 200 about the first element y-axis Y1 to the maximum angle. For example, the second abutment clearance C2 may be smaller than the fourth abutment sub-clearance C1d and the second abutment sub-clearance C1b.

The protrusion 240 and the accommodation recess 140 may be engageable with each other in a form-fit manner. The protrusion 240 and the accommodation recess 140 may, for example, be engaged by complementary shapes providing a form-fit engagement between the protrusion 240 and the accommodation recess 140 such that the protrusion 240 is relatively moveable within the accommodation recess 140 about at least one of the first element z-axis Z1 and a first element y-axis Y1. In addition thereto or alternatively, the protrusion 240 and the accommodation recess 140 may be engageable with each other to form a joint which is configured to allow the first and second coupling portions 120 and 220 to pivot relative to each other about only one or about at least one or about both (e.g. about at least both) of the first element y- and z-axes Y1 and Z1. For example, the joint formed by the protrusion 240 and the accommodation recess 140 may be a hinge joint configured to restrict (pivotal) movement of the protrusion 240 inside the accommodation recess 140 about the first element y-axis Y1 and the first element x-axis X1 while allowing (pivotal) movement of the protrusion 240 inside the accommodation recess 140 about the first element z-axis Z1. In a further example, the joint formed by the protrusion 240 and the accommodation recess 140 may be a hinge joint configured to restrict (pivotal)

movement of the protrusion 240 inside the accommodation recess 140 about the first element z-axis Z1 and the first element x-axis X1 while allowing (pivotal) movement of the protrusion 240 inside the accommodation recess 140 about the first element y-axis Y1. Alternative or other types of joint for the joint formed by the protrusion 240 and the accommodation recess 140 may include a ball joint configured to allow multidirectional movement about each of the first element x-, y- and z-axes X1, Y1 and Z1.

The accommodation recess 140 and the protrusion 240 may comprise complementary shapes in order to be engageable with each other. In one example, the accommodation recess 140 may comprise a hollow cylindrical portion 143 having a first longitudinal cylinder axis which extends along the first element y-axis Y1 and having a diameter D1, and comprises a hollow channel portion 146 extending parallel to the longitudinal cylinder axis and connecting the hollow cylindrical portion 143 to an exterior and having a channel width dimension W1 which is smaller than the diameter D1 of the hollow cylindrical portion 143. Further, the protrusion 240 may comprise an at least substantially cylindrical head portion 243 having a second longitudinal cylinder axis and having a diameter D2 matching the diameter D1 of the hollow cylindrical portion 143, and an elongated neck portion 246 extending parallel to the second longitudinal cylinder axis and having a neck width dimension W2 matching the channel width dimension W1 and connecting the head portion 243 with a remainder of the second implant element 200, whereby the protrusion 240 is insertable into the accommodation recess 140 along the first element y-axis Y1, with its head and neck portions 243 and 246 engaging the hollow cylindrical and hollow channel portions 143 and 146, respectively. However, the present invention is not limited to the above described shapes of the accommodation recess 140 and the protrusion 240. The accommodation recess 140 may for example also have a rectangular, rhomboid, trapezoidal, oval, circular or dove-tail cross-sectional shape and the protrusion 240 may accordingly have a complementary rectangular, rhomboid, trapezoidal, oval, circular or dove-tail cross-sectional shape.

Cylinder end faces 244a and 244b of the head portion 243 may have a (respective) chamfered circumferential edge 245a and 245b. Further, the neck portion 246, on its longitudinal ends 247a and 247b, may respectively have upper and lower chamfered edges 248a and 248b smoothly transitioning into the corresponding chamfered circumferential edge 245a and 245b (as for example also implemented in the embodiments shown in FIGS. 17 to 21, 26 and 27).

The fastener 300 may be a screw which can be tightly screwed into an inner thread 163 formed within the first insertion hole 160 to thereby fixedly attach the fastener 300 to the first coupling portion 120. The screw may have a countersunk head 303, and the first insertion hole 160 may comprise a complementary countersunk hole portion 166 to receive the countersunk head 303 in a flush manner. The fastener 300 may also have a threaded shaft 306 for engagement with the inner thread 163 of the first insertion hole 160 (as for example also implemented in the embodiment shown in FIG. 33).

The first insertion hole 160 may further have a first passage 169 and a second passage 172 which are formed in the first coupling portion 120 on opposite sides of the accommodation recess 140 so that, in the coupled condition of the first and second implant elements 100 and 200, the second insertion hole 260 is arranged between the first and second passages 169 and 172 in a sandwiched manner (as for example also implemented in the embodiments shown in FIGS. 1 to 11). In such a configuration, the inner thread 163 of the first insertion hole 160 may be formed within the second passage 172. When the fastener 300 is a screw having a head 303 and a threaded shaft 306, the threaded shaft 306 can be tightly screwed into the inner thread 163 formed within the second passage 172 to fixedly attach the fastener 300 to the first coupling portion 120 with the head 303 supported against the first coupling portion 120 at a position proximal to the first passage 169 and distal to the second passage 172 (as for example also implemented in the embodiments shown in FIGS. 1 to 11). Further, the countersunk hole portion 166 may be formed in the first passage 169.

The first implant element 100 may further include an elongated first stem portion 180 which extends along the first element x-axis X1 and which is to be inserted into a first bone portion (e.g. bone portion 6, 6') of a human patient's mandible 1 in order to fixedly attach the first implant element 100 to said first bone portion (as for example also implemented in the embodiments shown in FIGS. 1 to 16). The first stem portion 180 is, for example, to be inserted into the cancellous bone region of the first bone portion. The first stem portion 180 may, for example, be formed in an elongated cylindrical or conical shape or a combination thereof, but is not limited thereto. The first stem portion 180 may be provided with an outer thread. The outer thread of the first stem portion 180 may be a self-tapping thread or a thread without self-tapping characteristics. The first stem portion 180 may optionally include surface modification(s), such as a predetermined surface roughness, additional ridges, additional recesses, porous structures, and/or mesh-like portions etc., to promote osseointegration of the first stem portion 180 into the bone portion surrounding the first stem portion 180 and/or may optionally include active material(s), e.g. bioactive molecules and/or bioactive films, such as calcium phosphate, on its outer surface (e.g. coated thereon) to promote osseointegration of the first stem portion 180 into the bone portion surrounding the first stem portion 180. Further, the first implant element 100 may, alternatively or additionally, include surface modification(s) for promoting osseointegration, such as a predetermined surface roughness, additional ridges, additional recesses, porous structures, porous structures, and/or mesh-like portions etc., at surfaces thereof, which are different from the first stem portion 180 and which may come into contact with surrounding bone tissue, to promote osseointegration at these surfaces of the first implant element 100. Additionally or alternatively, the first implant element 100 may, alternatively or additionally, include surface modification(s) for promoting soft tissue integration, such as a predetermined surface roughness, additional ridges, additional recesses, porous structures, and/or mesh-like portions etc., at surfaces, thereof, which are different from the first stem portion 180 and which may come into contact with surrounding soft tissue, to promote soft tissue ingrowth and adhesion of surrounding soft tissue at these surfaces of the first implant element 100. Alternatively or additionally to the aforementioned, active material(s) for promoting osseointegration, e.g. bioactive molecules and/or bioactive films, such as, but not limited to, calcium phosphate, may be disposed (e.g. coated) on the surfaces, which are different from the first stem portion 180 and which may come into contact with surrounding bone tissue, of the first implant element 100 in order to promote osseointegration at these surfaces of the first implant element 100 into the surrounding bone tissue. Further alternatively or additionally to the aforementioned, active material(s) for promoting soft tissue integration, e.g.

bioactive molecules and/or bioactive films, such as, but not limited to, bioglass, may be disposed (e.g. coated) on the surfaces, which are different from the first stem portion 180 and which may come into contact with surrounding soft tissue, of the first implant element 100 to promote ingrowth and adhesion at these surfaces of the first implant element 100 element into the surrounding soft tissue.

The first stem portion 180 may further comprise one or more first stem through-holes 183 which extend through the first stem portion 180 in a direction at least substantially parallel to the first element y-axis Y1, and which are sized for accommodating a stem fixation screw (as for example also implemented in the embodiments shown in FIGS. 1 to 16). The respective first stem through-hole 183 may comprise an inner thread for engagement with an outer thread of the respective stem fixation screw.

The first implant element 100 may also comprise one or more threaded first plate attachment holes 190, 191 which extend in a direction at least substantially parallel to the first element y-axis Y1 and which are arranged between the first coupling portion 120 and the first stem portion 180 and which are sized to accommodate a respective plate attachment screw 63 for attaching a respective implant fixation plate thereto (as for example also implemented in the embodiments shown in FIGS. 1 to 16).

Figure 15:
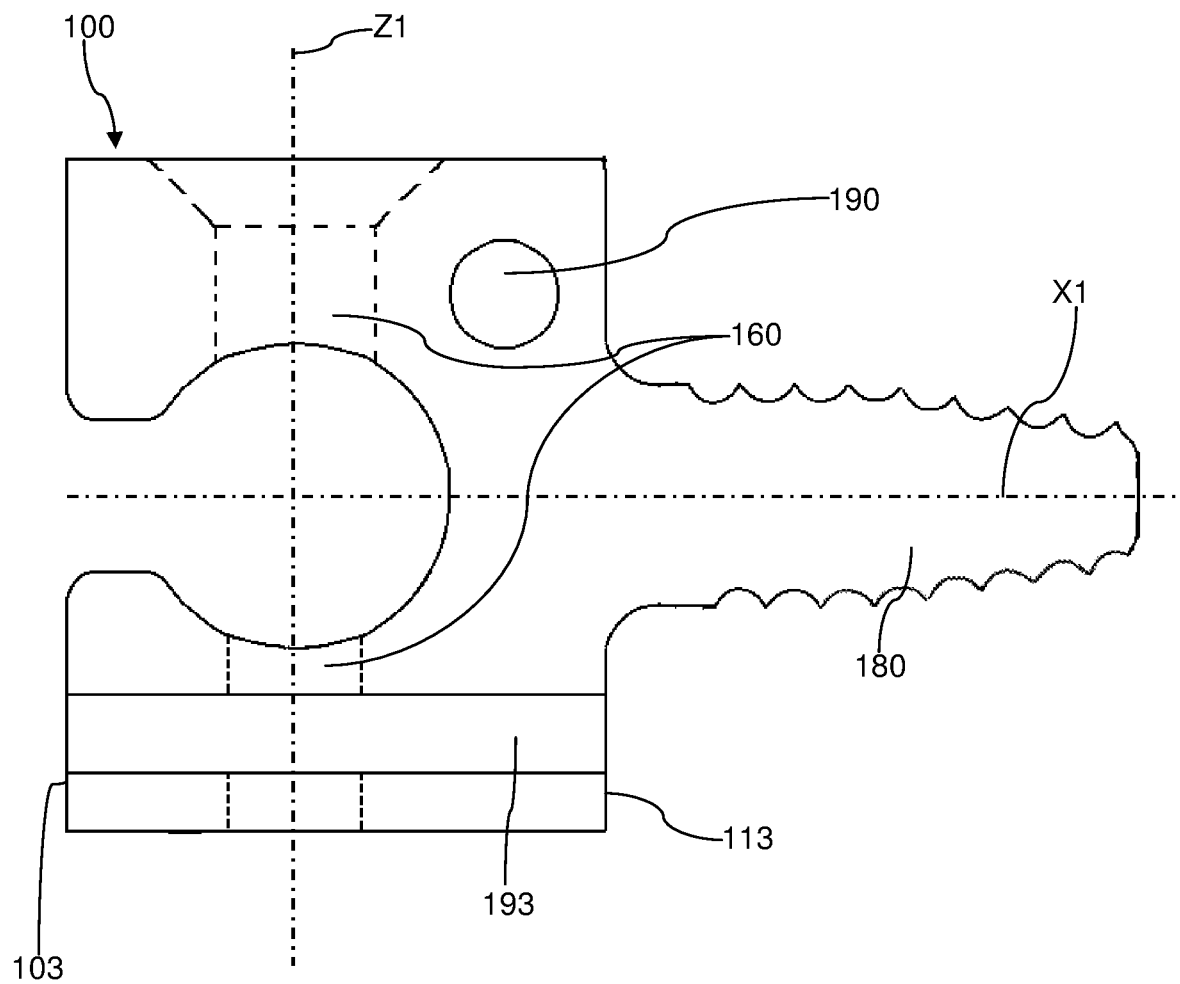
FIGS. 15 and 16 are a sectional view and a top view, respectively, illustrating a first implant element with a stem portion according to an embodiment of the invention, which further comprises first bone screw through-holes instead of a lower plate attachment hole.
Figure 16:
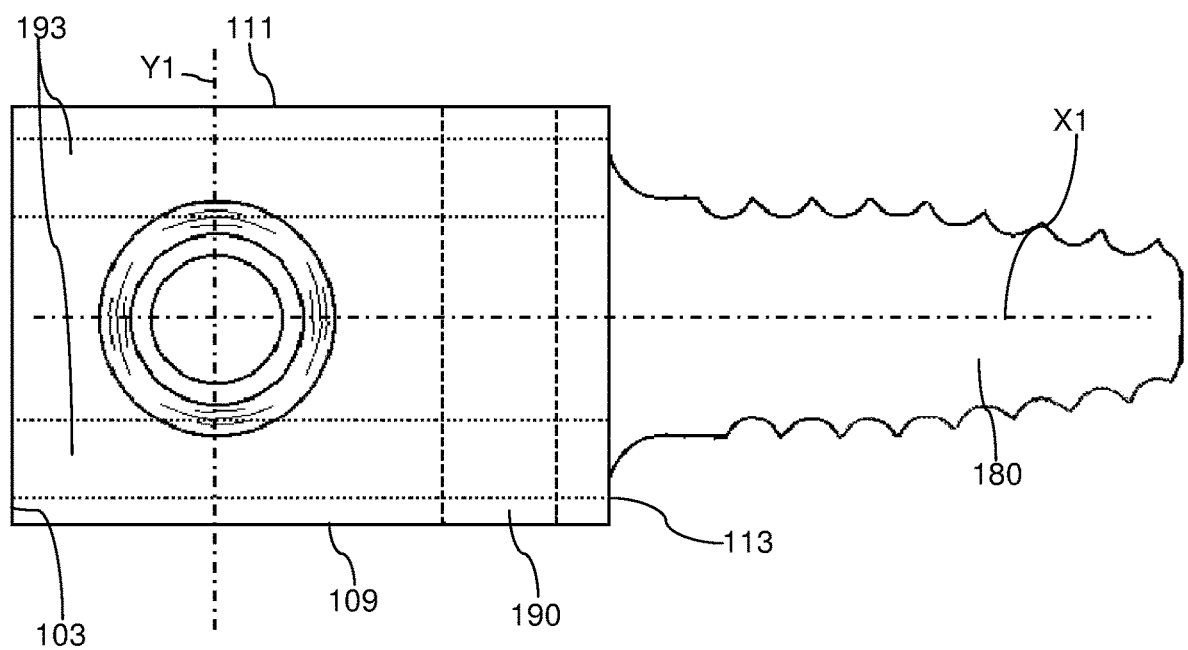

Further, the first implant element 100 may also include one or more first bone screw through-holes 193 which extend therethrough in a direction transverse to the first element z- and y-axes Z1 and Y1 and which are sized for accommodating a respective bone screw (as for example also implemented in the embodiment shown in FIGS. 15 and 16).

The first implant element 100 may comprise the one or more first stem through-holes 183, the one or more first threaded plate attachment holes 190, 191 and the one or more first bone screw through-holes 193 alone or in any combination thereof.

Also, the second implant element 200 may include an elongated second stem portion 280 which extends along the second element x-axis X2 and which is to be inserted into a second bone portion (e.g. bone portion 6, 6') of a patient's mandible 1 in order to fixedly attach the second implant element 200 to said second bone portion (as for example also implemented in the embodiments shown in FIGS. 17 to 21).

The second stem portion 280 is, for example, to be inserted into the cancellous bone region of the second bone portion. The second stem portion 280 may, for example, be formed in an elongated cylindrical or conical shape or a combination thereof, but is not limited thereto. Further, the second stem portion 280 may be provided with an outer thread. The outer thread of the second stem portion 280 may be a self-tapping thread or a thread without self-tapping characteristics. Similar to the first stem portion 180, the second stem portion 280 may include topological surface modification(s) and/or may include active material(s) on its outer surface (e.g. coated thereon) to promote osseointegration of the second stem portion 280 into the bone portion surrounding the second stem portion 280. Further, the second implant element 200 may, alternatively or additionally, include surface modification(s) for promoting osseointegration, such as a predetermined surface roughness, additional ridges, additional recesses, porous structures, and/or mesh-like portions etc., at its surfaces, which are different from the second stem portion 280 and which may come into contact with surrounding bone tissue, to promote osseointegration at these surfaces of the second implant element 200. Additionally or alternatively, the second implant element 200 include surface modification(s) for promoting soft tissue integration, such as a predetermined surface roughness, additional ridges, additional recesses, porous structures, and/or mesh-like portions etc., at surfaces thereof, which are different from the second stem portion 280 and which may come into contact with surrounding soft tissue, to promote soft tissue ingrowth and adhesion of surrounding soft tissue at these surfaces of the second implant element 200. Alternatively or additionally to the aforementioned, active material(s) for promoting osseointegration, e.g. bioactive molecules and/or bioactive films, such as, but not limited to, calcium phosphate, may be disposed (e.g. coated) on the surfaces, which are different from the second stem portion 180 and which may come into contact with surrounding bone tissue, of the second implant element 200 in order to promote osseointegration at these surfaces of the second implant element 200 into the surrounding bone tissue. Further alternatively or additionally to the aforementioned, active material(s) for promoting soft tissue integration, e.g. bioactive molecules and/or bioactive films, such as, but not limited to, bioglass, may be disposed (e.g. coated) on the surfaces, which are different from the second stem portion 280 and which may come into contact with surrounding soft tissue, of second implant element 200 to promote ingrowth and adhesion at these surfaces of the second implant element 200 into the surrounding soft tissue.

The second stem portion 280 may comprise one or more second stem through-holes 283 which extend through the second stem portion 280 in a direction, which is at least substantially parallel to a second element y-axis Y2 which is transverse to the second element x- and z-axes X2 and Z2, and which are sized for accommodating a respective stem fixation screw (as for example also implemented in the embodiments shown in FIGS. 17 to 21). The respective second stem through-hole may comprise an inner thread for engagement with an outer thread of the respective stem fixation screw.

The second implant element may further comprise one or more second threaded plate attachment holes 290, 291 which extend in a direction, which is at least substantially parallel to the second element y-axis Y2, and which are arranged between the second coupling portion 220 and the second stem portion 280 and which are sized to accommodate a respective plate attachment screw 63 for attaching a respective implant fixation plate thereto (as for example also implemented in the embodiments shown in FIGS. 17 to 21).

Figure 19:
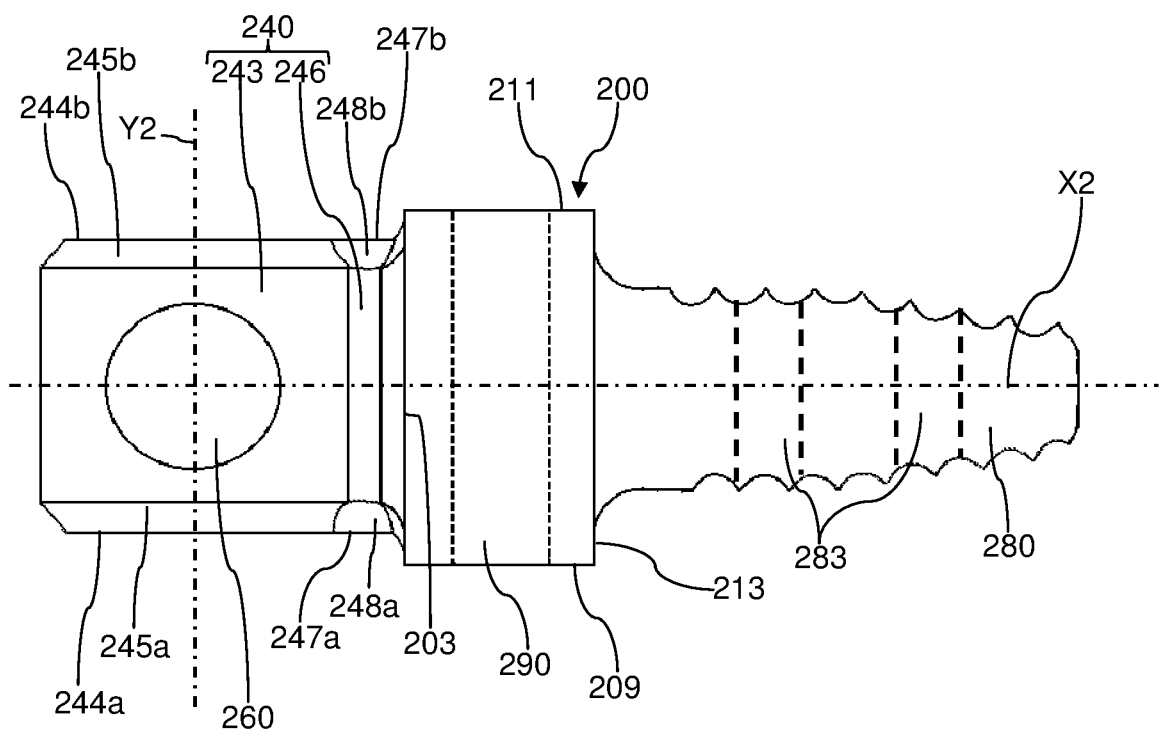
FIG. 19 is a top view of the view of the second implant element of FIG. 17.
Figure 21:
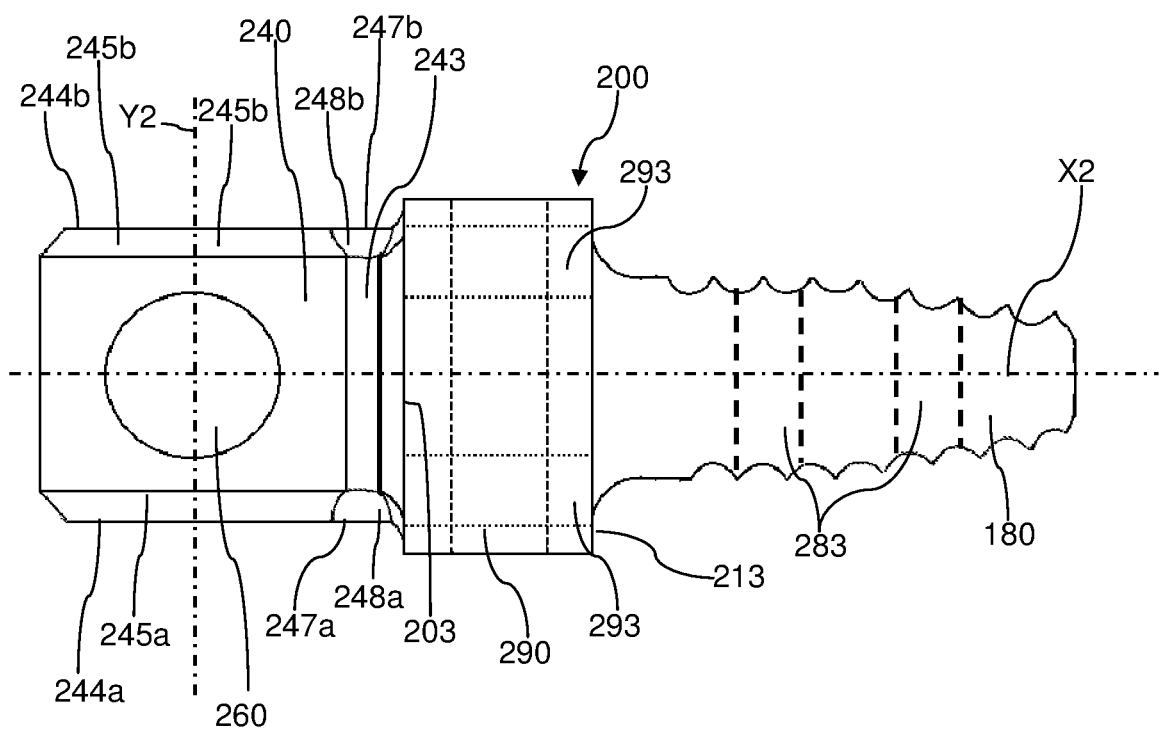

Further, the second implant element may comprise one or more second bone screw through-holes 293 which extend therethrough in a direction, which is transverse to the second element z-axis Z2 and to the second element y-axis Y2, and which are sized for accommodating a respective bone screw (as for example also implemented in the embodiment shown in FIGS. 19 and 21).

The second implant element 200 may comprise the one or more second stem through-holes 283, the one or more second threaded plate attachment holes 290, 291 and the one or more second bone screw through-holes 293 alone or in any combination thereof.

The mandible endoprosthesis implant according to the invention has a modular design in which various first and second elements 100 and 200, having the above described structures, may be combined and assembled so that a surgeon can, prior to or even during surgery, appropriately adapt the mandible endoprosthesis implant to the resected portion 2 of the patient's mandible 1 which is to be bridged by the mandible endoprosthesis implant.

The second implant element 200 may be formed in one piece (i.e. monolithically) with a further first implant element 100' which is formed like the first implant 100 as described in this application, wherein the accommodation recess 140' of the further first implant element 100' and the protrusion 240 of the second implant element 200 may be oppositely arranged. Optionally, the x-axes of the second and further first implant elements 200 and 100' may at least be substantially aligned with each other. It is to be understood that the second and further first implant elements 200 and 100' may also be formed in one piece such that the second and further first implant element 200 and 100' form an angled or curved piece as desired for the specific application. The first implant element 100 may be coupled to the second implant element 200 and a further second implant element 200' may be coupled to the further first implant element 100' in the manner as described in this application by a respective fastener 300, 300'. In this configuration, the first implant element 100 and the further second implant 200' may for example include a respective stem portion 180 and 280' and may be accordingly connected with each other by the monolithically formed second and further first implant elements 200 and 100'.

Figure 28A:
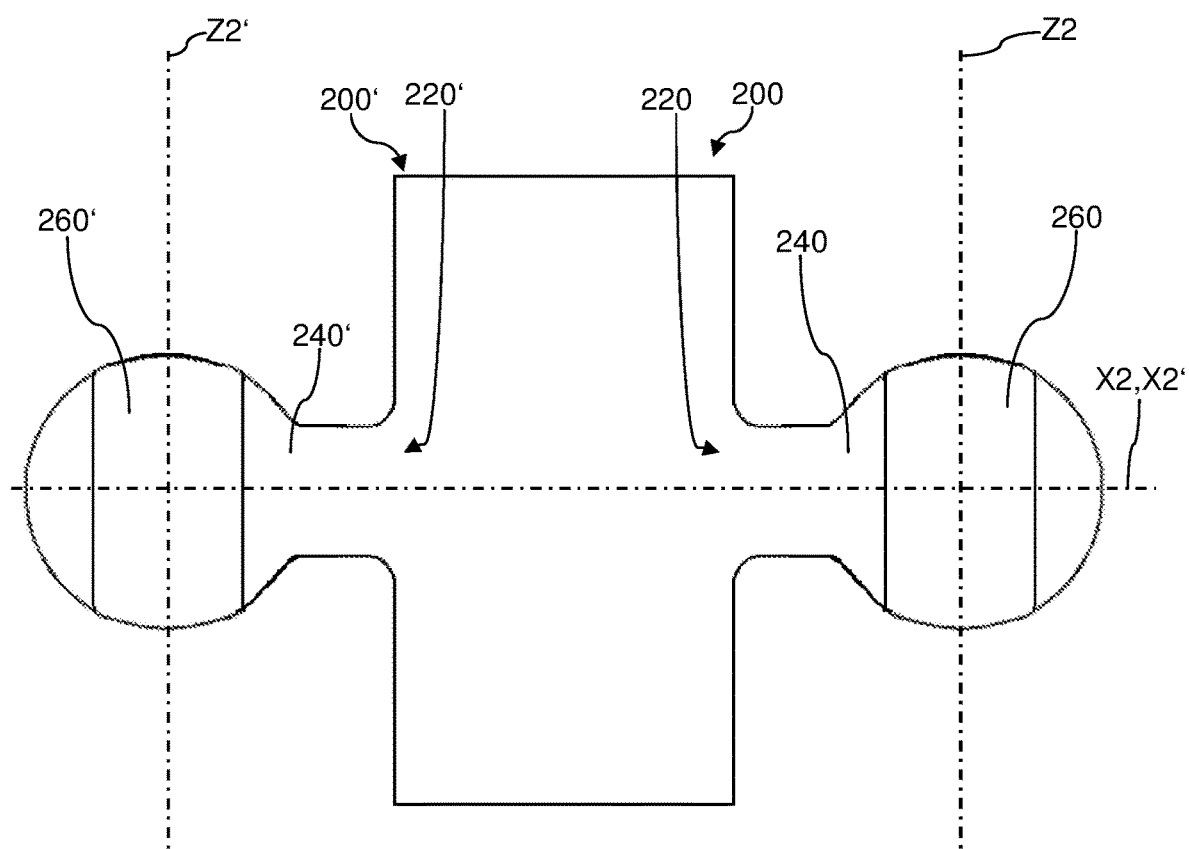
FIG. 28a is a sectional view of a second implant element according to an embodiment of the invention, which is formed in one piece with a further second implant element along the plane formed by the x- and z-axes of the implant elements.
Figure 28B:
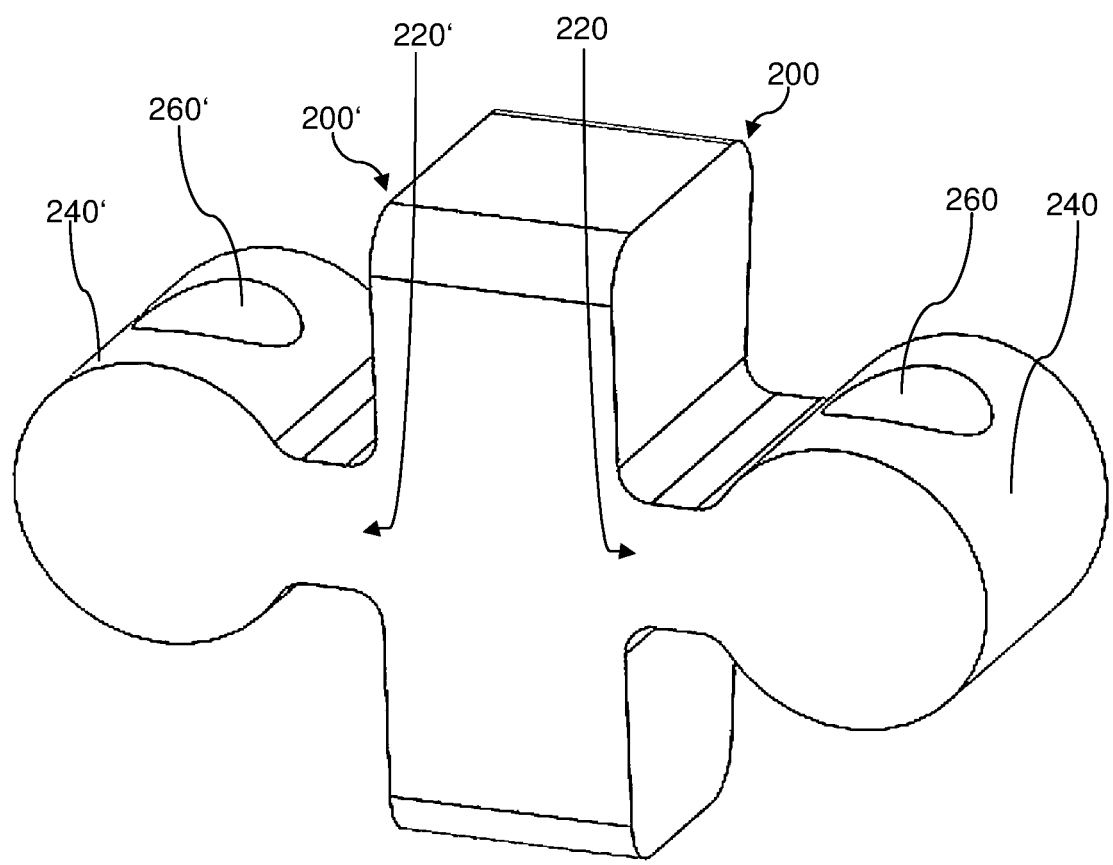
Figure 29:
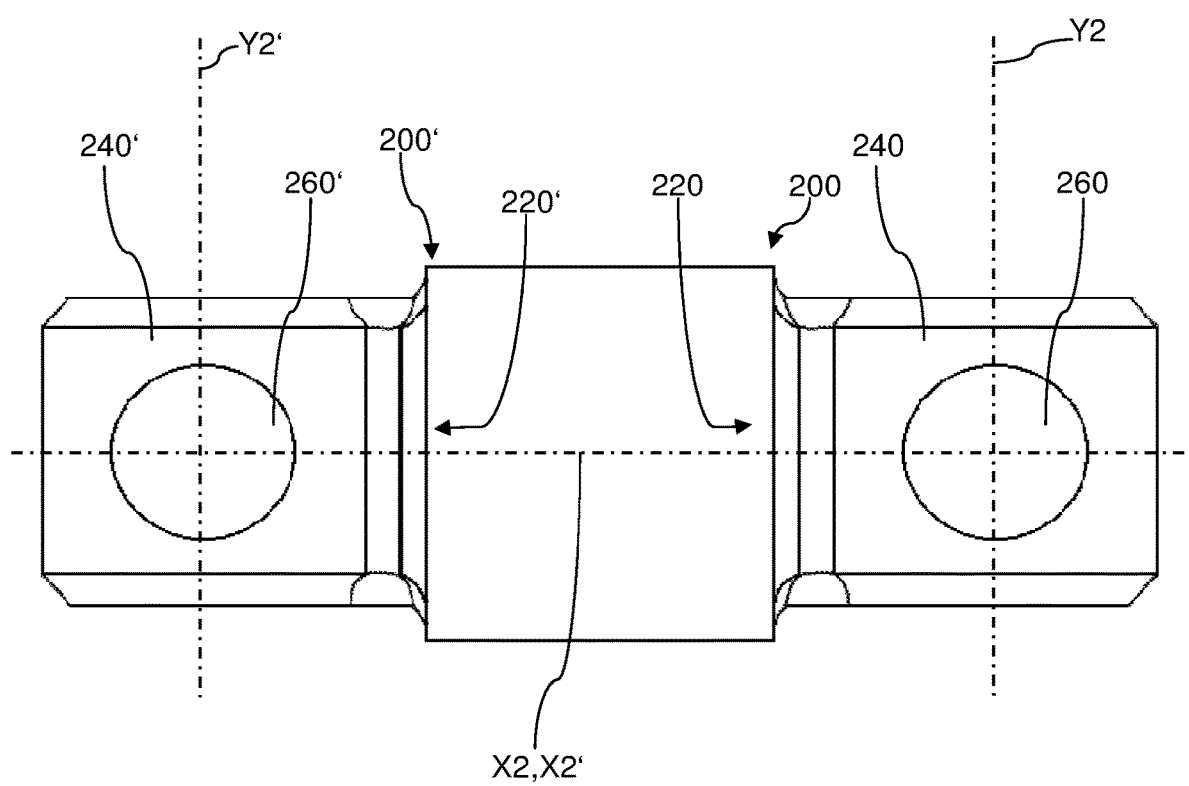

Moreover, the second implant element 200 may be formed in one piece with a further second implant element 200' which is formed like the second implant 200 as described in this application, wherein the protrusion 240' of the further second implant element 200 and the protrusion 240 of the second implant element 200 may be oppositely arranged (as for example also implemented in the embodiment shown in FIGS. 28a, 28b and 29). Further, the x-axes of the second and further second implant elements 200 and 200' may optionally be at least substantially aligned with each other. It is to be understood that the second and further second implant elements 200 and 200' may also be formed in one piece such that the second and further second implant elements 200 and 200' form an angled or curved piece as desired for the specific application. The first implant element 100 may be coupled to the second implant element 200 and a further first implant element 100' may be coupled to the further second implant element 200'. In this configuration, the first implant element 100 and the further first implant element 100' may for example include a respective stem portion 180 and 180' and may be accordingly connected with each other by the monolithically formed second and further second implant elements 200 and 200' (as for example also implemented in the embodiment shown in FIGS. 2 and 3).

Figure 24:
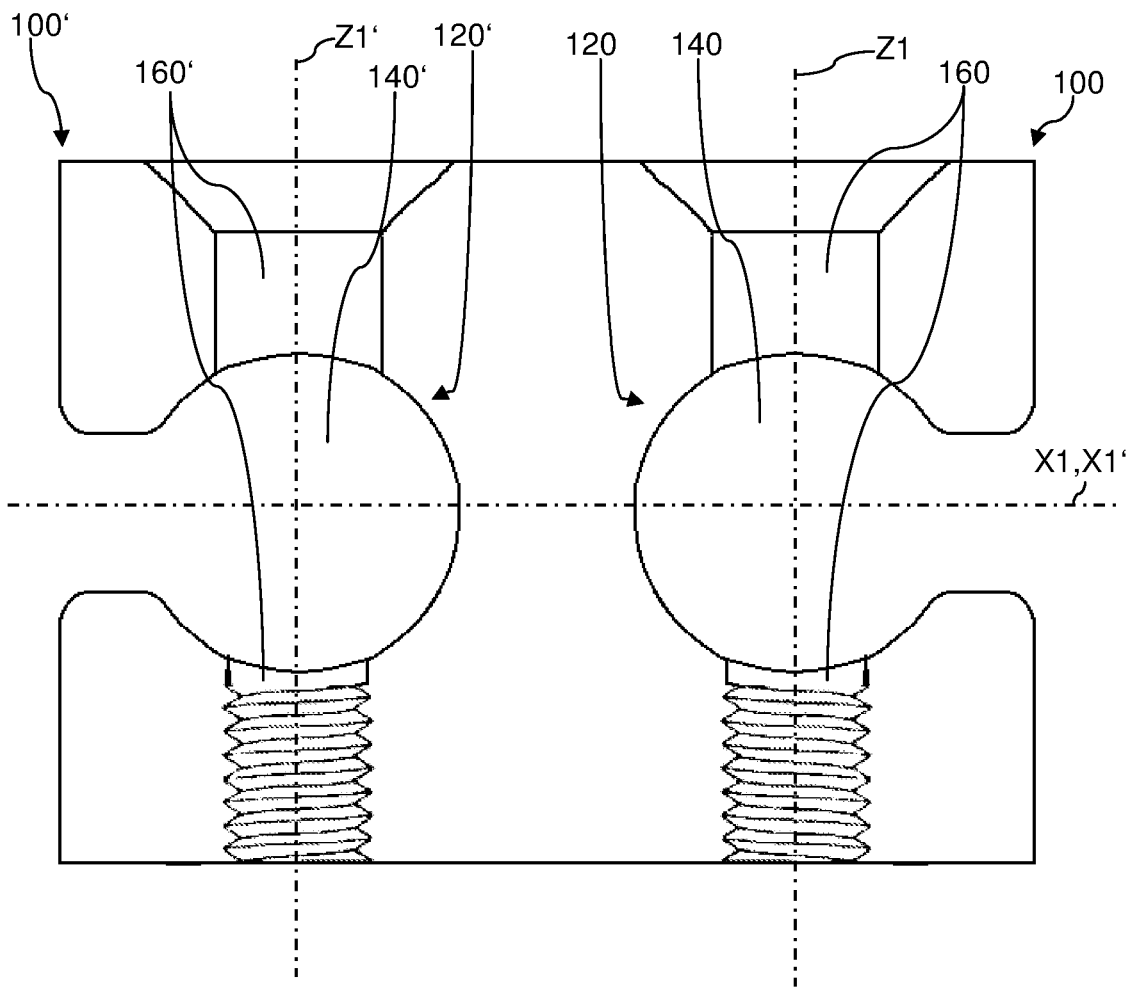
FIG. 24 is a sectional view of a first implant element according to an embodiment of the invention, which is formed in one piece with a further first implant element along the plane formed by the x- and z-axes of the implant elements.
Figure 25:
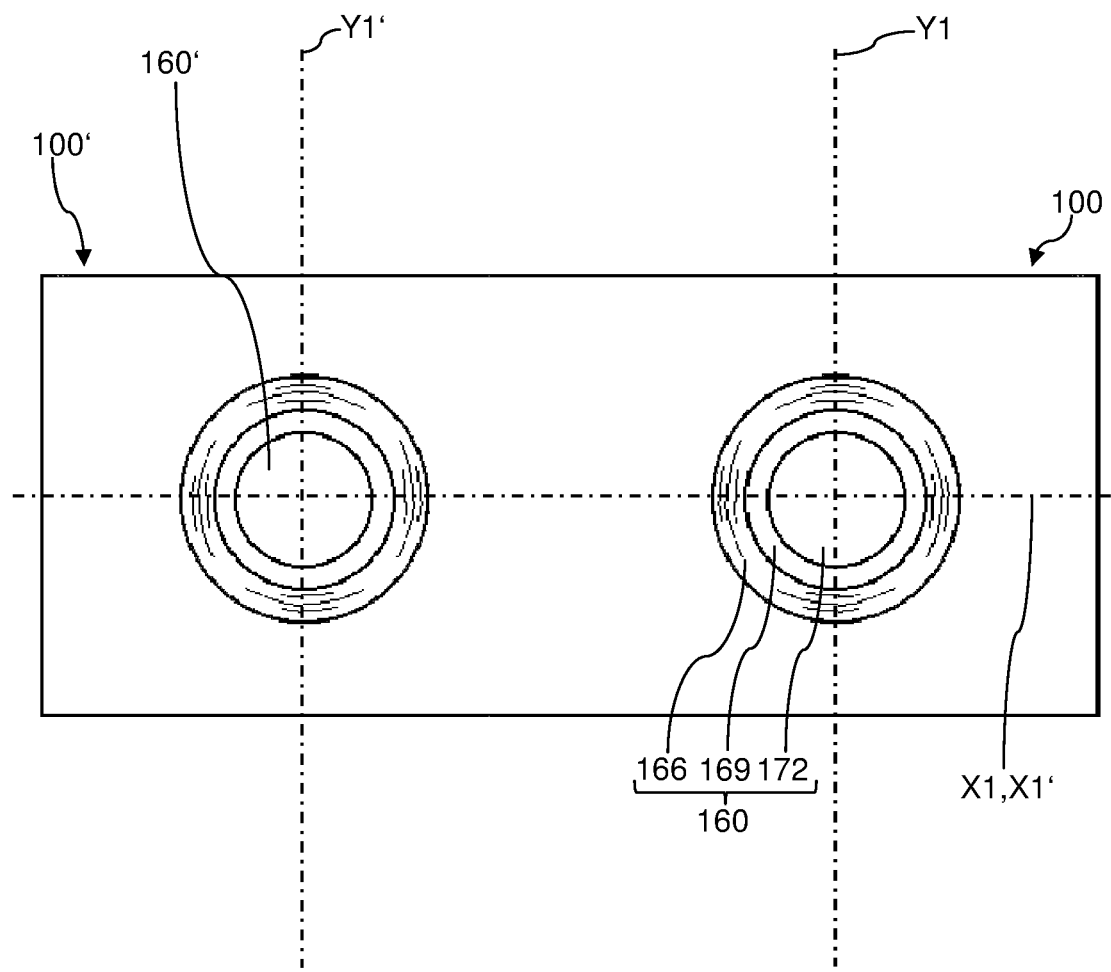
FIG. 25 is a top view of the first implant element, which is formed in one piece with the further first implant element, of FIG. 24.
Figure 30A:
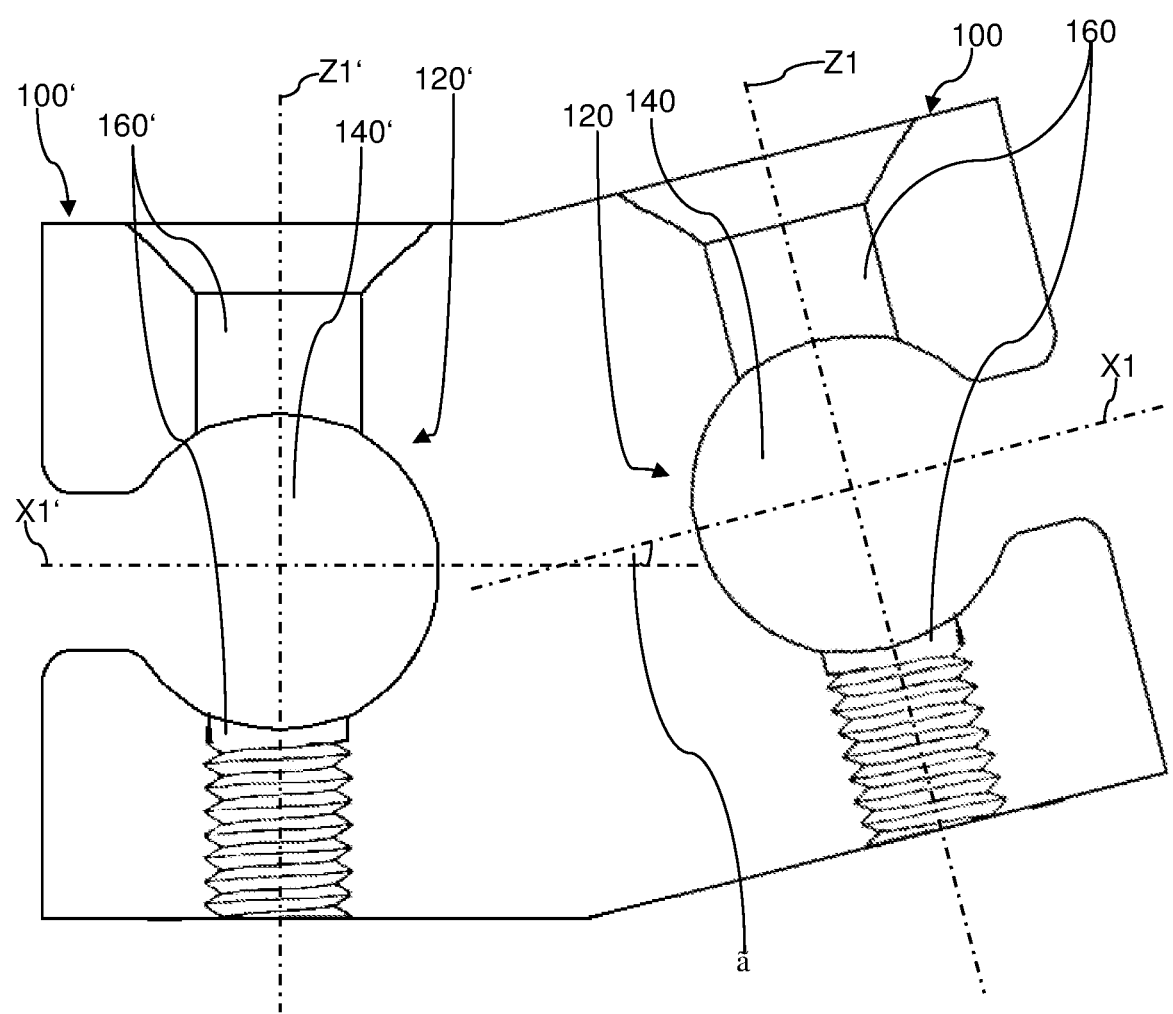
FIG. 30a illustrates a variation of the embodiment of FIGS. 24 and 25, in which the first and further first implant elements are formed in one piece and are orientated at an angle relatively to each other.

Further, the first implant element 100 may be formed in one piece with a further first implant element 100' which is formed like the first implant element 100 as described in this application, wherein the accommodation recess 140' of the further first implant element 100' and the accommodation recess 140 of the first implant element 100 may be oppositely arranged (as for example also implemented in the embodiments shown in FIGS. 24, 25 and 30). Optionally, the x-axes of the first and further first implant elements 100 and 100' may at least be substantially aligned with each other. It is to be understood that the first and further first implant elements 100 and 100' may also be formed in one piece such that the first and further first implant element 100 and 100' form an angled or curved piece as desired for the specific application (as for example also implemented in the embodiment shown in FIG. 30a). The first implant element 100 may be coupled to the second implant element 200 and a further second implant element 200' may be coupled to the further first implant element 100' in the manner as described in this application by a respective fastener 300, 300'. In this configuration, the second implant element 200 and the further second implant 200' may for example include a respective stem portion 280 and 280' and may be accordingly connected with each other by the monolithically formed first and further first implant elements 100 and 100' (as for example also implemented in the embodiment shown in FIGS. 10 and 11).

Figure 26:
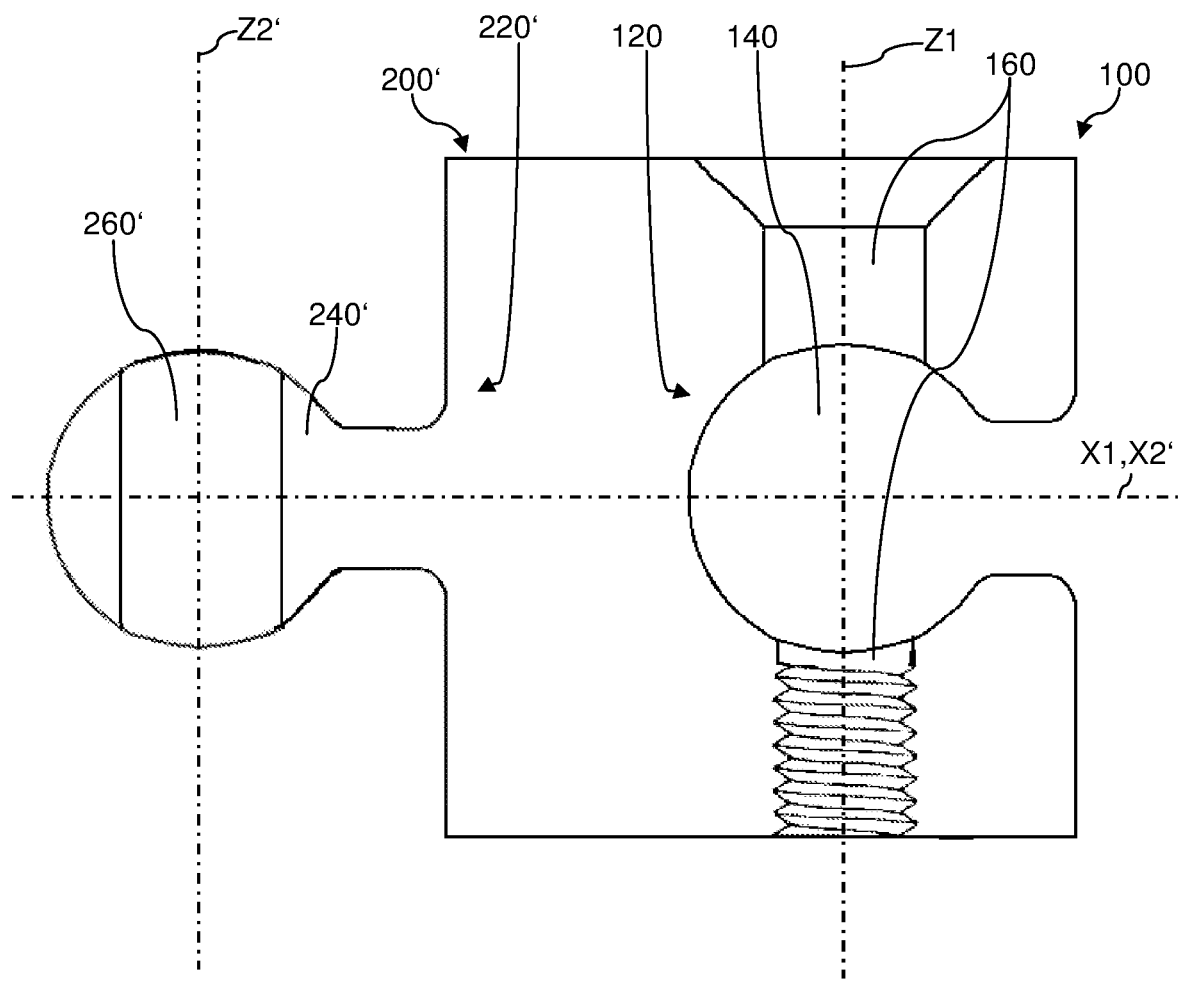
FIG. 26 is a sectional view of a first implant element according to an embodiment of the invention, which is formed in one piece with a further second implant element along the plane formed by the x- and z-axes of the implant elements.
Figure 27:
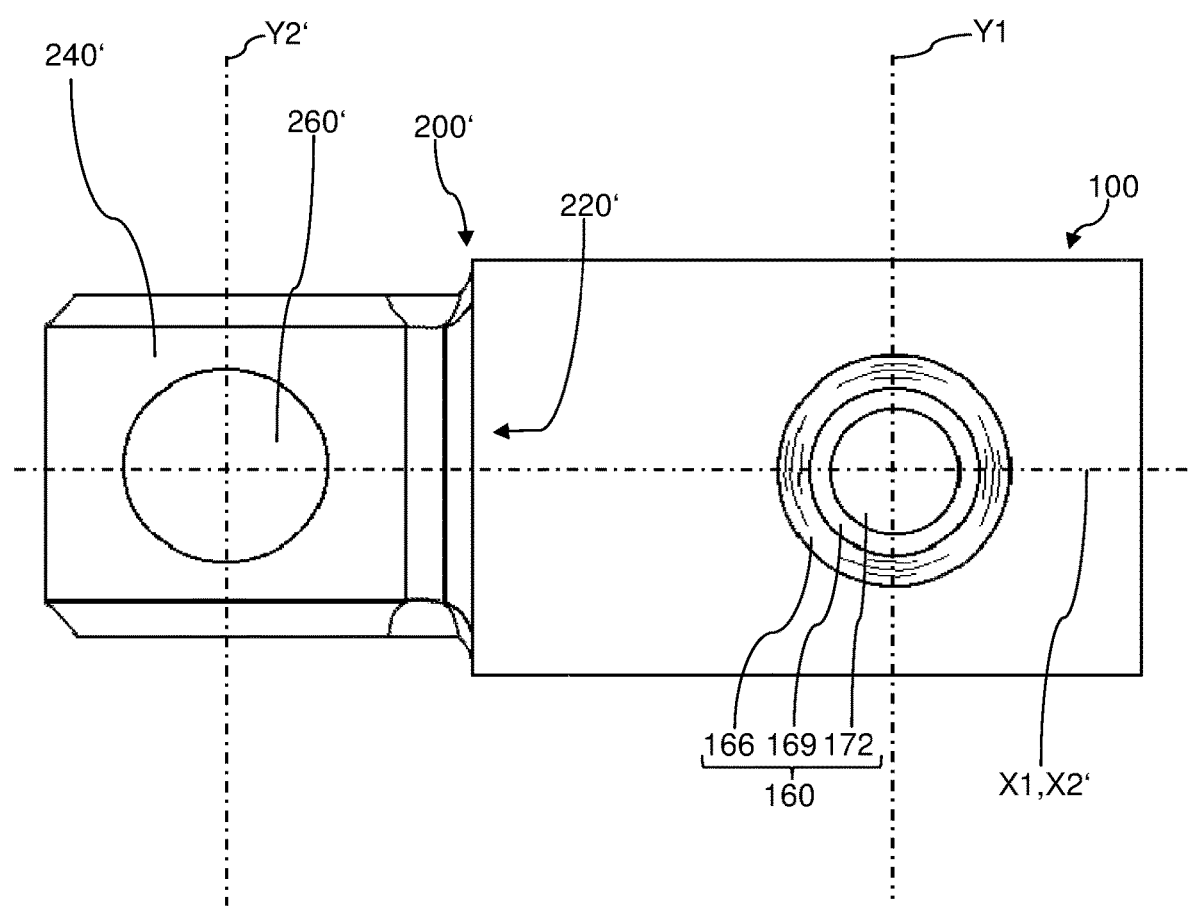
FIG. 27 is a top view of the first implant element, which is formed in one piece with the further second implant element, of FIG. 26.

Also, the first implant element 100 may be formed in one piece with a further second implant element 200', which is formed like the second implant 200 as described in this application, wherein the protrusion 240' of the further second implant element 200 and the accommodation recess 140 of the first implant element 100 may be oppositely arranged (as for example also implemented in the embodiment shown in FIGS. 26 and 27). Further, the x-axes of the first and further second implant elements 100 and 200' may optionally be at least substantially aligned with each other. It is to be understood that the first and further second implant elements 100 and 200' may also be formed in one piece such that the first and further second implant element 100 and 200' form an angled or curved piece as desired for the specific application. The first implant element 100 may be coupled to the second implant element 200 and a further first implant element 100' may be coupled to the further first implant element 200' in the manner as described in this application by a respective fastener 300, 300'. In this configuration, the first implant element 100 and the further first implant 100' may for example include a respective stem portion 180 and 180' and may be accordingly connected with each other by the monolithically formed first and further second implant elements 100 and 200'.

The above described monolithically formed implant elements may be used for reconstruction of the mandible body of a patient's mandible 1. When reconstructing the mandible body by the one or more monolithically formed implants elements as described in this application, it may be desired that osseointegration and/or soft tissue integration occurs at the used one or more monolithically formed implants elements. To this end, one, some or all of the used one or more monolithically formed implant elements may include surface modification(s) for promoting osseointegration, such as a predetermined surface roughness, additional ridges, additional recesses, porous structures, and/or mesh-like portions etc., at surfaces thereof, which may come into contact with surrounding bone tissue, to promote osseointegration of the monolithically formed implant element. Alternatively or additionally, one, some or all of the used one or more monolithically formed implant elements may be (e.g., entirely or partially) formed with a mesh-like or trabecular-like structure (e.g. made from a trabecular metal material, such as trabecular metal material available from Zimmer Biomet) to promote ingrowth of surrounding bone and/or soft tissue. Further alternatively or additionally, one, some or all of the used one or more monolithically formed implant elements may include surface modification(s) for promoting soft tissue integration, such as a predetermined surface roughness, additional ridges, additional recesses, porous structures, and/or mesh-like portions etc., at surfaces thereof, which may come into contact with surrounding soft tissue, to promote soft tissue ingrowth and adhesion of surrounding soft tissue to the monolithically formed implant element. Alternatively or additionally to the aforementioned, active material(s) for promoting osseointegration, e.g. bioactive molecules and/or bioactive films, such as, but not limited to, calcium phosphate, may be disposed (e.g. coated) on the surfaces, which may come into contact with surrounding bone tissue, of the one, some or all of the used one or more monolithically formed implant elements in order to promote osseointegration at these surfaces. Further alternatively or additionally to the aforementioned, active material(s) for promoting soft tissue integration, e.g. bioactive molecules and/or bioactive films, such as, but not limited to, bioglass, may be disposed (e.g. coated) on the surfaces, which may come into contact with surrounding soft tissue, of the one, some or all of the used one or more monolithically formed implant elements to promote soft tissue integration at these surfaces.

The modular design of the endoprosthesis of the present invention allows for reconstruction of variable defect sizes for different patients using standardized pre-fabricated modular components, eliminating the need for customization of the implant to fit each patient's defect. As the exact defect size is often only determined during surgery, the present invention will also allow surgeons to match and select the appropriate-sized standardized components to reconstruct each mandible defect at the time of surgery.

The present invention also provides a mandible endoprosthesis implant that is suited for reconstruction of the condyle-ramus region 7 of the mandible 1. To this end, the first implant element 100 may further comprise a curved shaft portion 196 which is formed in a shape that corresponds to the ramus region, which is to be replaced by the first implant element 100, of a patient's mandible. The shaft portion 196 of the first implant element 100 may further comprise a joint head 198 which is shaped so that it can engage with the natural articular disk and fossa of a temporomandibular joint of the patient (as for example also implemented in the embodiment shown in FIG. 22). According to a further example, the second implant element 200 may comprise a curved shaft portion 296 which is formed in a shape that corresponds to a ramus region, which is to be replaced by the second implant element 200, of a patient's mandible (as for example also implemented in the embodiment shown in FIG. 23). Similar to the shaft portion 196 of the first implant element 100, the shaft portion 296 of the second implant element 200 may further a joint head 298 which is shaped so that it can engage with the natural articular disk and fossa of a temporomandibular joint of the patient.

One, some or all of the implant elements used in a mandible endoprosthesis implant according to the invention may have a height along their respective z-axis and a width along their respective y-axis which correspond approximately to the height and width of the bone portions of the mandible which are to be bridged by the mandible endoprosthesis implant, respectively. For example, said height along the respective z-axis may be about 70% of the total height of the bone portions (e.g. the bone portions 6, 6' as illustrated in the Figures) of the mandible which are to be bridged by the mandible endoprosthesis. In this regard, the heights (height of the respective implant element(s) and the total height of the mandible) may be measured from the bottom of the mandible so that the upper surface of the respective implant element is positioned below the top of the mandible. Further, one, some or all of the implant elements used in a mandible endoprosthesis implant according to the invention may be adapted for attaching dental implants, such as prosthetic teeth, thereto in order to further reconstruct the patient's mandible. For example, a monolithically formed implant element (as for example implemented in the embodiment shown in FIGS. 24 to 30) may include one or more prosthetic teeth attachment holes which extend in parallel to the respective z-axes into the monolithically formed implant element from a top surface thereof and which serve for insertion of one or more dental implants. It is also to be understood that one, some or all of the implant elements used in a mandible endoprosthesis implant according to the invention may be provided with surface modification(s) and/or active material(s) for promoting osseointegration, such as those described hereinbefore, on one or more surfaces that may come into contact with surrounding bone tissue and/or may be provided with surface modification(s) and/or active material(s) for promoting soft tissue integration, such as those described hereinbefore, one or more surfaces that may come into contact with surrounding soft tissue.

The present invention also provides a mandible endoprosthesis implant system. The mandible endoprosthesis implant system comprises a mandible endoprosthesis implant, wherein the mandible endoprosthesis implant may comprise one or more first plate attachment holes 190, 191 in the first element 100 as described in this application (as for example also implemented in the embodiments shown in FIGS. 34 to 37). The system also comprises one or more implant fixation plates (e.g. implant fixation plates 320*a* to 320*b* as shown in FIGS. 34 to 37), each having at least a first and a second screw insertion through-hole (e.g. first and a second screw insertion through-holes 322*a* to 322*d* and 324*a* to 324*d* as shown in FIGS. 34 to 37), and comprises one or more plate attachment screws (e.g. plate attachment screws 66 to 69 as shown in FIGS. 34 to 37) and one or more bone screws (e.g. bone screws 60 to 63 as shown in FIGS. 34 to 37). A respective implant fixation plate may be attachable to the first implant element 100 by the respective plate attachment screw passing through the first screw insertion through-hole and engaging the respective first plate attachment hole 190, 191, and may be attachable to the first bone portion of the patient's mandible 1 by the respective bone screw passing through the second screw insertion through-hole and engaging the first bone portion of the patient's mandible 1. The one or more implant fixation plates may be elongated and may have a length which is at maximum the length of the first implant element 100 along the first element x-axis.

In such a mandible endoprosthesis implant system, with the mandible endoprosthesis implant may also have one or more plate attachment holes 290, 291 in the second element 200 as described in this application. A respective implant fixation plate is attachable to the second implant element 200 by the respective plate attachment screw passing through the first screw insertion through-hole and engaging the respective second plate attachment hole 290, 291, and is attachable to the second bone portion of the patient's mandible 1 by the respective bone screw passing through the second screw insertion through-hole and engaging the second bone portion of the patient's mandible 1. The one or more implant fixation plates may be elongated and may have a length which is at maximum the length of the second implant element 100 along the second element x-axis.

The one or more implant fixation plates may be plastically deformable. Therefore, the one or more implant fixation plates can be plastically deformed, e.g. prior to or during the surgery, so as to follow the contour of the bone portion, to which they are to be attached, of the patient's mandible. The system may further include one or more elongated bone fixation plates 340 having first and second longitudinal plate ends 341 and 343, each provided with a respective bone fixation through-hole 342 and 344 for being passed by a respective one of the one or more bone screws 68 and 69, wherein the one or more bone fixation plates 340 are each longer than each of the one or more implant fixation plates (as for example also implemented in the embodiment shown in FIG. 37).

It is to be understood that the various plates (implant fixation plates and/or bone fixation plates) may be attached to the implant elements and/or to the bone portions by one or more corresponding screws, respectively, depending on the required stability and the available space. Exemplarily described for connecting the first implant element and the first bone portion to each other, it may be contemplated to use, e.g., one, two or more bone screws in order to attach the first implant fixation plate to the first bone portion and to use, e.g., one, two or more plate fixation screws in order to attach the first implant fixation plate to the first implant element. It is apparent that various numbers of screws may similarly also be used in the case of connecting the second implant element and the second bone portion to each other and/or in the case of connecting the bone fixation plate to the bone portions and/or to implant elements.

The present invention also provides a surgical kit comprising a plurality of mandible endoprosthesis implants as described in this application. For example, the surgical kit may comprise fasteners 300 and a plurality of complementary first and second implant elements 100 and 200 in various configurations, such as first and second implant elements 100 and 200 provided with respective stem portions 180 and 280, first implant elements 100 which are formed in one piece with a further first or further second implant element 100' or 200' and/or second implant elements 200 which are formed in one piece with a further first or further second implant element 100' or 200'. The surgical kit may also comprise implant fixation plates 320a to 320d, a bone fixation plate 340, bone screws 60 to 63 and plate attachment screws 66 to 69.

The surgical kit according to the present invention may further include an elongated first locking device (e.g. in the form of a first locking rod 420 or in the form of first and second locking caps 420a and 420b as implemented in the embodiments shown in FIGS. 38a to 38g) and a first implant element mount 400, 400' (as for example also implemented in the embodiment shown in FIGS. 38a to 38g). The first implant element mount 400, 400' comprises a first end 405, 405' and a second end 410, 410'. The first end 405, 405' of the first implant element mount 400, 400' is attachable to a hand tool 430. The second end 410, 410' of the first implant element mount 400, 400' comprises a mount protrusion 415, 415' which is engageable with the accommodation recess 140 of the first implant element 100 (e.g. of a first implant element 100 having a first stem portion 180), thereby establishing a coupled condition between the first implant element mount 400, 400' and the first implant element 100. The first locking device is engageable with the first implant element mount 400, 400' and is engageable with the first implant element 100 to lock the first implant element 100 and the first implant element mount 400, 400' together.

The surgical kit according to the present invention may further include an elongated second locking device (e.g. in the form of a second locking rod 470 as implemented in the embodiment shown in FIG. 39) and a second implant element mount 450 (as for example also implemented in the embodiment shown in FIG. 39), wherein the second implant element mount 450 comprises a first end 455 and a second end 460. The first end 455 of the second implant element mount 450 is attachable to a hand tool 430. The second end 460 of the second implant element mount 400 comprises a mount recess 465 which is engageable with the protrusion 240 of the second implant element 200 (e.g. of a second implant element 200 having a second stem portion 280), thereby establishing a coupled condition between the second implant element mount 450 and the second implant element 200. The second locking device is engageable with the second implant element 200 and engageable with the second implant element mount 450 to lock the second implant element 200 and the second implant element mount 450 together.

The surgical kit according to the present invention may further include a hand tool 430 which comprises a mount attachment portion 435 for attaching the first end 405, 405', 455 of a respective implant element mount 400, 450 thereto, and comprises a grip portion 440 to be gripped by a surgeon, wherein the hand tool 430 (e.g. the mount attachment portion 435 thereof) may be configured to rotate the respective implant element mount 400, 450 when the respective implant element mount 400, 450 is attached to the mount attachment portion 435 of the hand tool 430. It may be contemplated that the hand tool 430 is a dental handpiece (or dental drill) well known to the skilled person in the art.

The surgical kit according to the present invention may further include a first surgical guide 500 which comprises a first guide plate 510 and a first guide locking head 520 connected to the first guide plate 510 (as for example also implemented in the embodiment shown in FIGS. 40a to 40d). The first guide locking head 520 comprises a guide protrusion 525 which is engageable with the accommodation recess 140 of the first implant element 100. The first guide plate 510 may comprise one or more first guide apertures 515 which are matchable with (e.g. pre-determined) positions of one or more first stem through-holes 183 on the first stem portion 180, respectively, by engaging the guide protrusion 525 with the accommodation recess 140 of the first implant element 100.

The surgical kit according to the present invention may further include a second surgical guide 550 which comprises a second guide plate 560 and a second guide locking head 570 connected to the second guide plate 560 (as for example also implemented in the embodiment shown in FIGS. 41a to 41d). The second guide locking head 570 comprises a guide recess 575 which is engageable with the protrusion 240 of the second implant element 200. The second guide plate 560 comprises one or more second guide apertures 565 which are matchable with (e.g. pre-determined) positions of one or more second stem through-holes 283 on the second stem portion 280, respectively, by engaging the guide recess 565 with the protrusion 240 of the second implant element 200.

The surgical kit according to the present invention may also include a plurality of screws (e.g. plate attachment screws, stem attachment screws, stem fixation screws, bone screws, etc.). It is to be understood that the surgical kit of the present invention is not limited to the above mentioned components and may include further components, such as (dental) surgical instruments and apparatuses required for the desired application. It is to be further understood that the components of the surgical kit of the present invention may be sold in combination (e.g. the surgical kit may comprise selected or all of the components mentioned herein) or may be sold alone (e.g. the surgical kit may comprise only one selected component, such as a single implant element, a single mandible endoprothesis implant (i.e. its multiple implant elements and fastener(s)), the first implant element modular mount, the second implant element modular mount, the first surgical guide, the second surgical guide, and so on).

Further, the present invention provides a method of surgically repairing a human's mandible by the use of a mandible endoprothesis implant according to the present invention.

Figure 2:
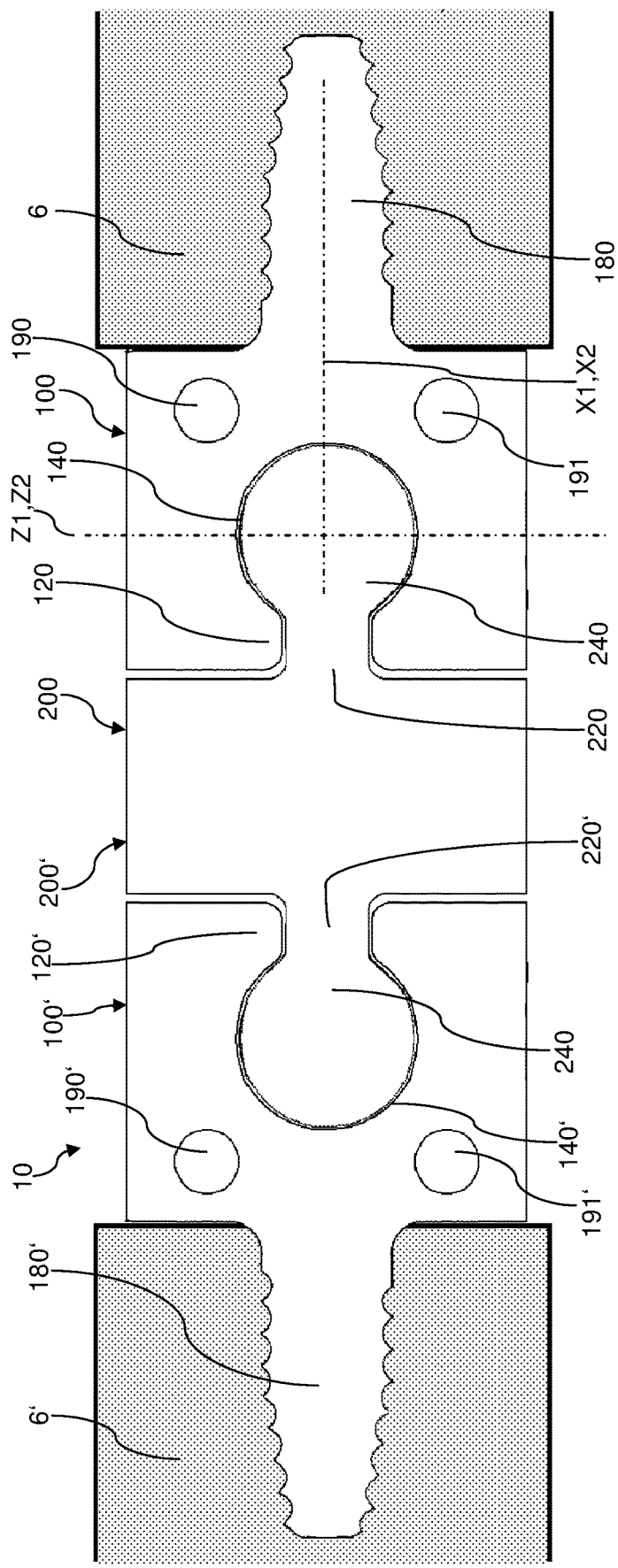
FIG. 2 is a side view of a mandible endoprosthesis implant according to the first embodiment fixed to bone portions of the mandible.
Figure 10:
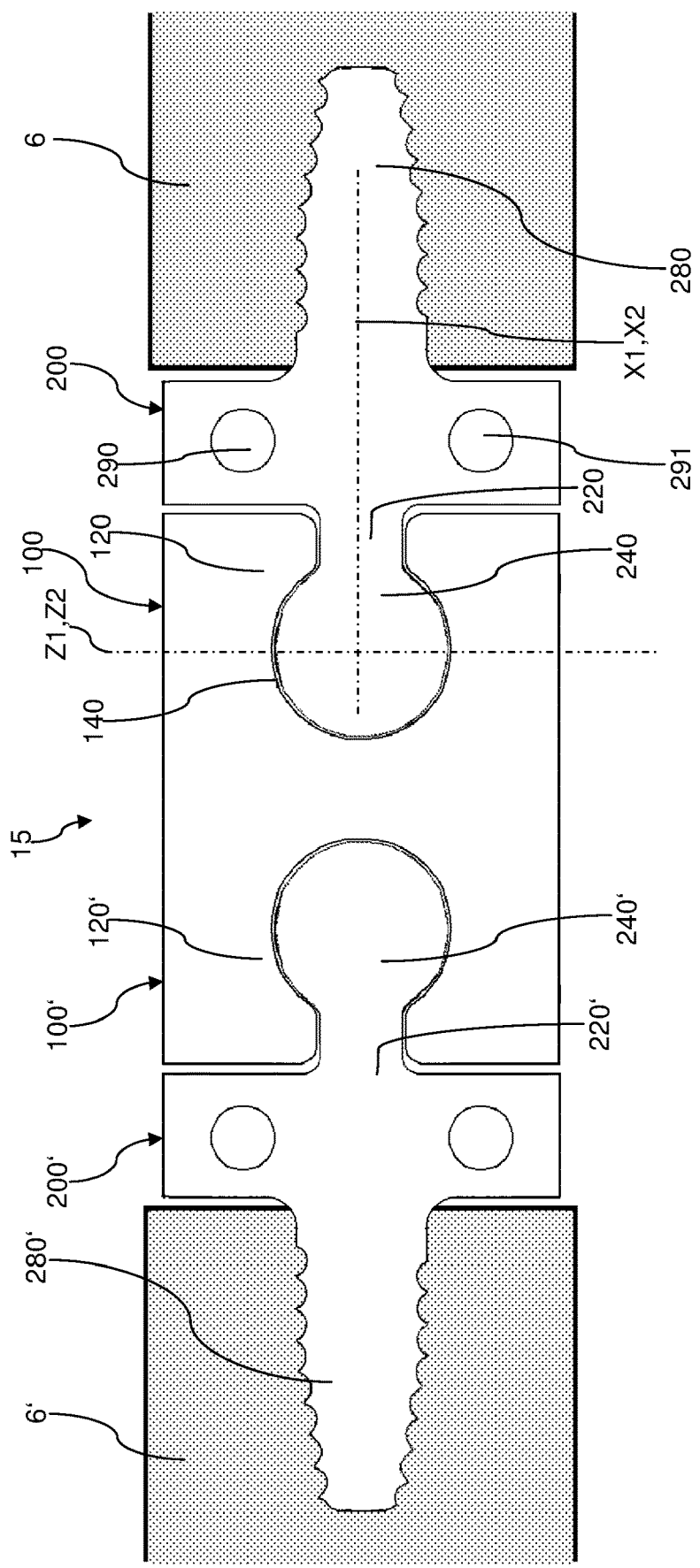
FIG. 10 is a side view of a mandible endoprosthesis implant according to a second embodiment fixed to bone portions of the mandible.
Figure 12:
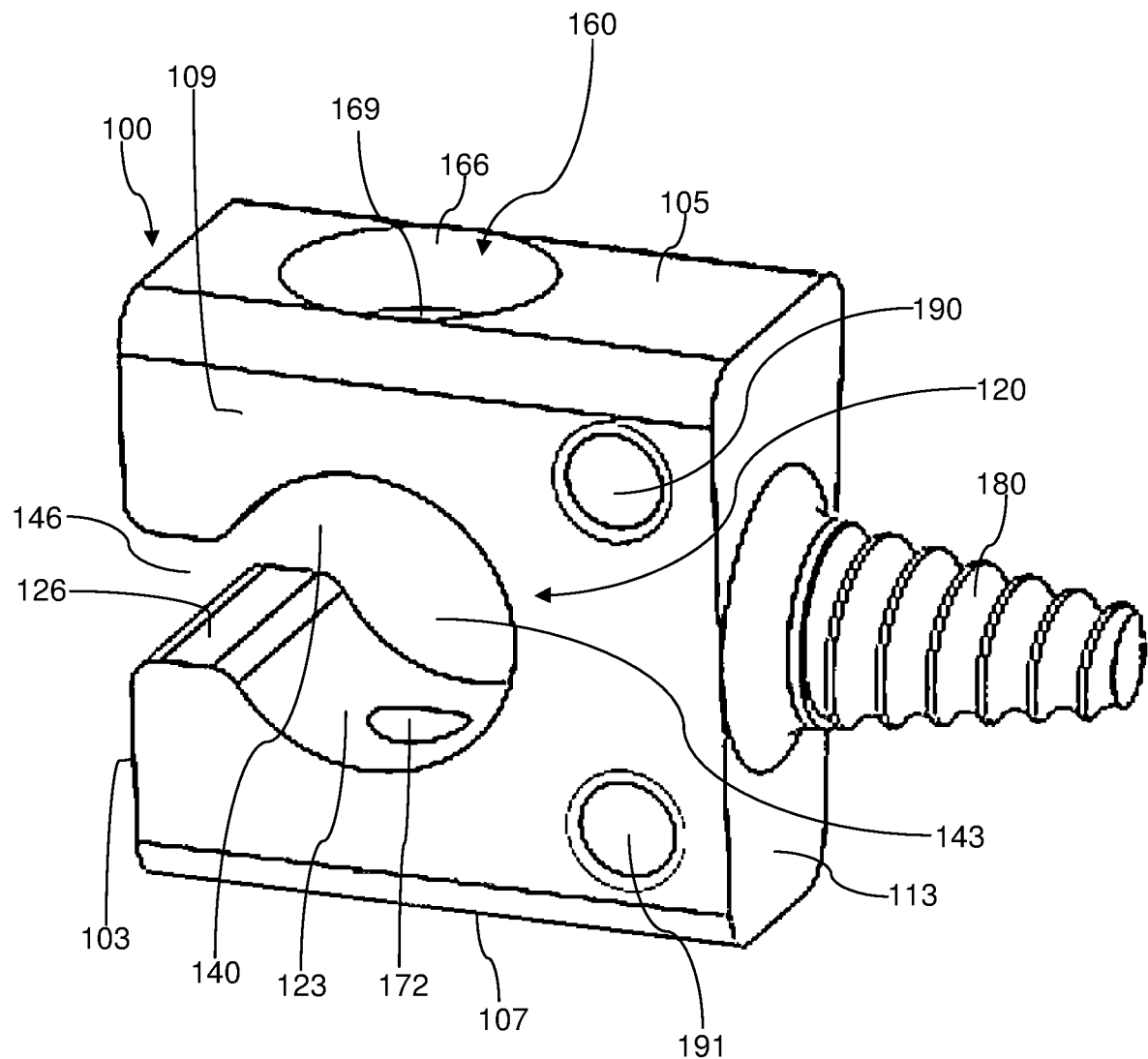
FIG. 12 is a perspective view of a first implant element with a stem portion according to an embodiment of the invention.

In a first example according to the present invention, the method of surgically repairing a human's mandible may include providing a mandible endoprosthesis implant which comprises a first implant element (e.g. a first implant element 100 having a first stem portion 180 as shown in, e.g., FIGS. 2 and 12) and a second implant element which is formed in one piece with a further first implant element (e.g. a monolithically formed implant element similar to the one shown in FIG. 26), and the method may further include providing a further second implant element (e.g. a further second implant element 200' having a corresponding stem portion 280' as shown in FIG. 10). The method may further include providing a further fastener. The method may further include fixedly attaching the first implant element to a bone portion (e.g. bone portion 6) on a first side of a resected portion of the mandible and may include fixedly attaching the further second implant element to a bone portion (e.g. bone portion 6') on a second side of the resected portion of the mandible. The method may include engaging the protrusion of the second implant element and the accommodation recess of the first implant element with each other such that the first and second insertion holes of the first implant element and the second implant element are at least substantially aligned with each other, thereby establishing the coupled condition between the first implant element and the second implant element. Further, the method may include engaging the protrusion of the further second implant element and the accommodation recess of the further first implant element with each other such that the first and second insertion holes of the further first implant element and the further second implant element are at least substantially aligned with each other, thereby establishing the coupled condition between the further first implant element and the further second implant element. The method according to the first example may also include engaging the fastener into both the first and second insertion holes of the first implant element and the second implant element and fixedly attaching the fastener to the first coupling portion of the first implant element and may include engaging the further fastener into both the first and second insertion holes of the further first implant element and the further second implant element and fixedly attaching the further fastener to the first coupling portion of the further first implant element.

In a second example according to the present invention, the method of surgically repairing a human's mandible may, include may include providing a mandible endoprosthesis implant which comprises a first implant element (e.g. a first implant element 100 having a first stem portion 180 as shown in, e.g., FIGS. 2 and 12) and a second implant element which is formed in one piece with a further second implant element (e.g. a monolithically formed implant element similar to the one shown in, e.g., FIGS. 2 and 28), and the method may further include providing a further first implant element (e.g. a further second implant element 100' having a corresponding stem portion 180' as shown in, e.g., FIG. 2). The method may also include providing a further fastener. Further, the method may include fixedly attaching the first implant element to a bone portion (e.g. bone portion 6) on a first side of a resected portion of the mandible and may include fixedly attaching the further first implant element to a bone portion (e.g. bone portion 6') on a second side of the resected portion of the mandible. According to the second example, the method may also include engaging the protrusion of the second implant element and the accommodation recess of the first implant element with each other such that the first and second insertion holes of the first implant element and the second implant element are at least substantially aligned with each other, thereby establishing the coupled condition between the first implant element and the second implant element, and may include engaging the protrusion of the further second implant element and the accommodation recess of the further first implant element with each other such that the first and second insertion holes of the further first implant element and the further second implant element are at least substantially aligned with each other, thereby establishing the coupled condition between the further first implant element and the further second implant element. Further, the method may include engaging the fastener into both the first and second insertion holes of the first implant element and the second implant element and fixedly attaching the fastener to the first coupling portion of the first implant element and may include engaging the further fastener into both the first and second insertion holes of the further first implant element and the further second implant element and fixedly attaching the further fastener to the first coupling portion of the further first implant element. The method according to the third example may result in a mandible defect which is repaired by use of a mandible endoprothesis implant according to the present invention as shown in, e.g., FIGS. 1 to 3.

Figure 17:
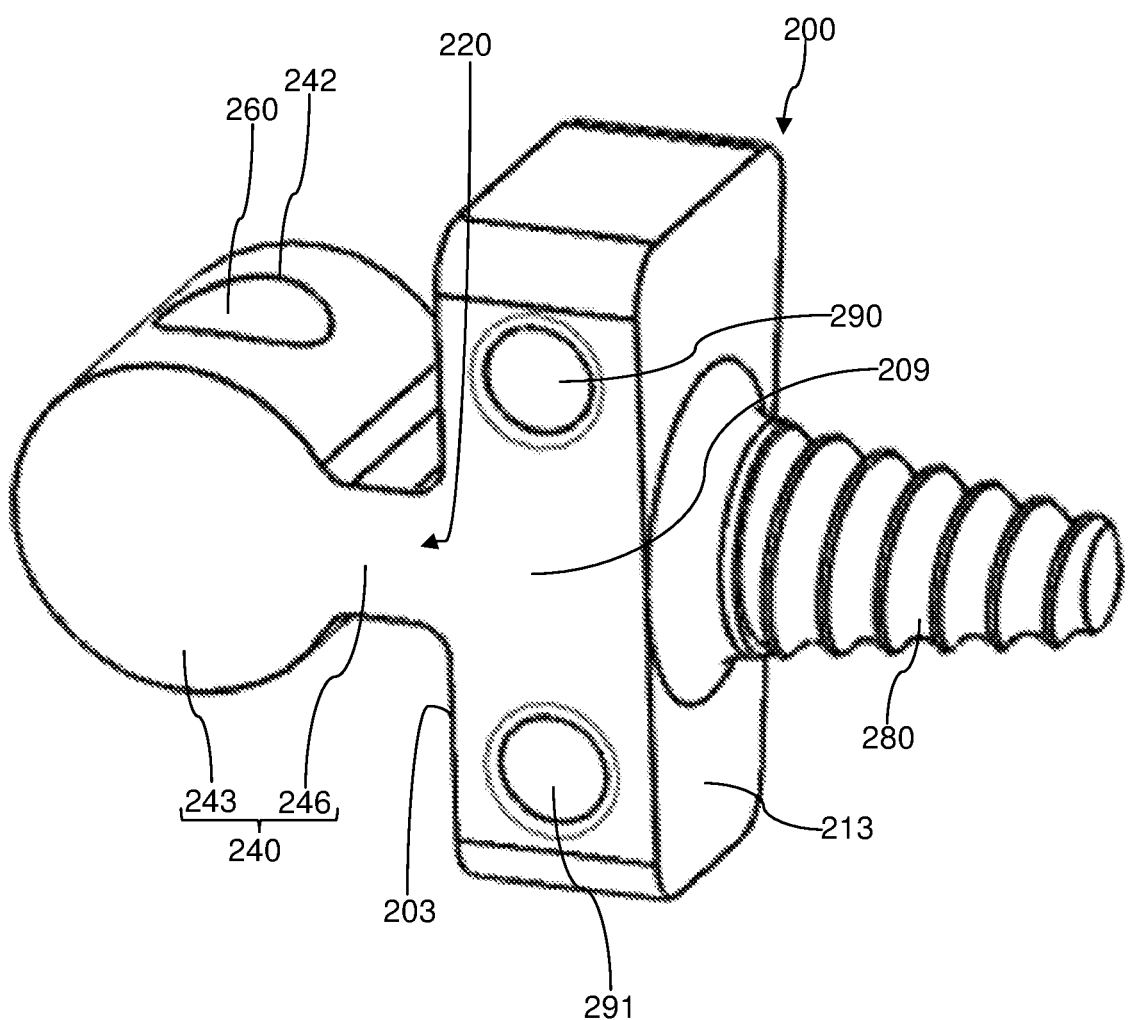
FIG. 17 is a perspective view of a second implant element with a stem portion according to an embodiment of the invention.

In a third example according to the present invention, the method of surgically repairing a human's mandible may include providing a mandible endoprosthesis implant which comprises a first implant element which is formed in one piece with a further first implant element (e.g. a monolithically formed implant element similar to the one shown in, e.g., FIGS. 10 and 24) and a second implant element (e.g. a second implant element 200 having a second stem portion 280 as shown in, e.g., FIGS. 10 and 17), and the method may further include providing a further second implant element (e.g. a further second implant element 200' having a corresponding stem portion 280' as shown in, e.g., FIG. 10). The method according to the third example may further include providing a further second implant element and may include providing a further fastener. Further, the method may include fixedly attaching the second implant element to a bone portion (e.g. bone portion 6) on a first side of a resected portion of the mandible and may include fixedly attaching the further second implant element to a bone portion (e.g. bone portion 6') on a second side of the resected portion of the mandible. The method may then include engaging the protrusion of the second implant element and the accommodation recess of the first implant element with each other such that the first and second insertion holes of the first implant element and the second implant element are at least substantially aligned with each other, thereby establishing the coupled condition between the first implant element and the second implant element, and may include engaging the protrusion of the further second implant element and the accommodation recess of the further first implant element with each other such that the first and second insertion holes of the further first implant element and the further second implant element are at least substantially aligned with each other, thereby establishing the coupled condition between the further first implant element and the further second implant element. Further, the method according to the third example may include engaging the fastener into both the first and second insertion holes of the first implant element and the second implant element and fixedly attaching the fastener to the first coupling portion of the first implant element, and may include engaging the further fastener into both the first and second insertion holes of the further first implant element and the further second implant element and fixedly attaching the further fastener to the first coupling portion of the further first implant element. The method according to the third example may result in a mandible defect which is repaired by use of a mandible endoprothesis implant according to the present invention as shown in, e.g., FIGS. 10 and 11.

In a fourth example according to the present invention, the method of surgically repairing a human's mandible may include providing a mandible endoprosthesis implant which comprises a first implant element which is formed in one piece with a further second implant element (e.g. a monolithically formed implant element similar to the one shown in, e.g., FIG. 26) and a second implant element (e.g. a second implant element 200 having a second stem portion 280 as shown in, e.g., FIGS. 10 and 17), and the method may further include providing a further second implant element (e.g. a further second implant element 200' having a corresponding stem portion 280' as shown in, e.g., FIG. 10). The method according to the fourth example may further include providing a further first implant element and may also include providing a further fastener. Furthermore, the method may include fixedly attaching the second implant element to a bone portion on a first side of a resected portion of the mandible and may include fixedly attaching the further first implant element to a bone portion on a second side of the resected portion of the mandible. The method may then include engaging the protrusion of the second implant element and the accommodation recess of the first implant element with each other such that the first and second insertion holes of the first implant element and the second implant element are at least substantially aligned with each other, thereby establishing the coupled condition between the first implant element and the second implant element, and include engaging the protrusion of the further second implant element and the accommodation recess of the further first implant element with each other such that the first and second insertion holes of the further first implant element and the further second implant element are at least substantially aligned with each other, thereby establishing the coupled condition between the further first implant element and the further second implant element. Furthermore, the method may include engaging the fastener into both the first and second insertion holes of the first implant element and the second implant element and fixedly attaching the fastener to the first coupling portion of the first implant element and include engaging the further fastener into both the first and second insertion holes of the further first implant element and the further second implant element and fixedly attaching the further fastener to the first coupling portion of the further first implant element.

It is to be understood that, in the first to fourth example of the method of surgically repairing a human's mandible according to the present invention, the step of engaging the protrusion and the accommodation recess of respective two adjacent implant elements may be immediately followed by the step of engaging the fastener into both the first and second insertion holes of these respective two adjacent implant elements. It may also be contemplated that the step of engaging the protrusion and the accommodation recess of respective two adjacent implant elements is immediately followed by engaging the protrusion and the accommodation recess of respective other two adjacent implant elements.

Figure 22:
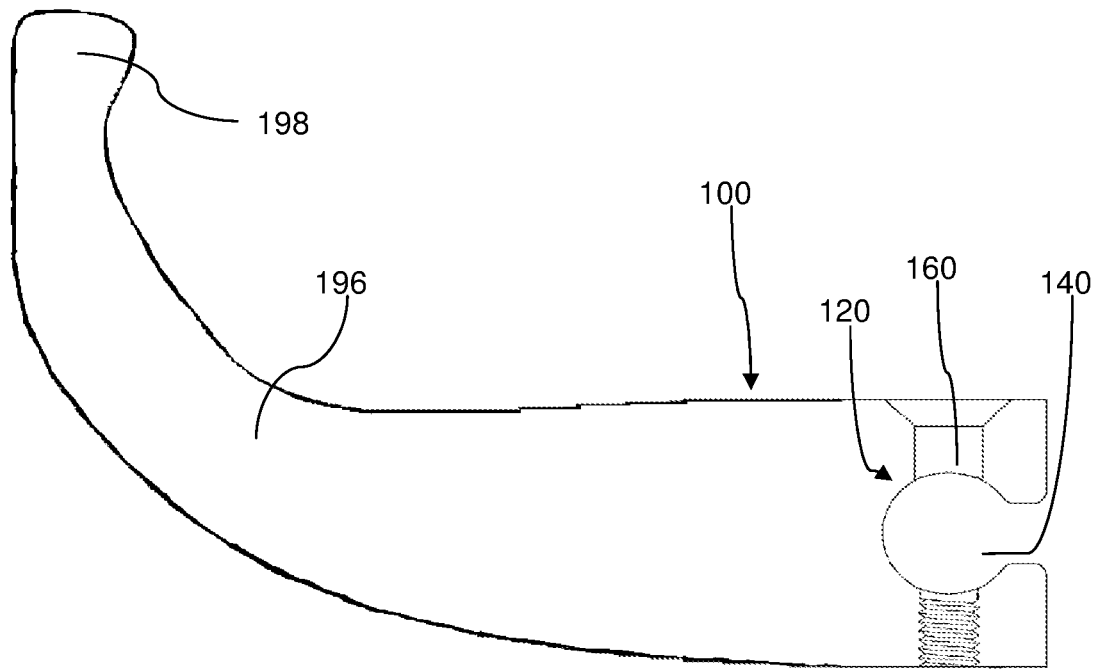
FIG. 22 illustrates a first implant element according to an embodiment of the invention, which can be used for reconstruction of the condyle-ramus region of the mandible.

In a fifth example according to the present invention, the method of surgically repairing a human's mandible may include providing a first implant element which, among others, comprises a curved shaft portion with a joint head as described in this application (e.g. a first implant element which comprises a curved shaft portion 196 with a joint head 198 as for example implemented in the embodiment shown in FIG. 22) and a second implant element (e.g. a second implant element 200 having a second stem portion 280 as shown in, e.g., FIGS. 10 and 17). The method according to the fifth example may further include fixedly attaching the second implant element to a bone portion (e.g. bone portion 6) of a resected portion of the mandible and include engaging the protrusion of the second implant element and the accommodation recess of the first implant element with each other such that the first and second insertion holes of the first implant element and the second implant element are at least substantially aligned with each other, thereby establishing the coupled condition between the first implant element and the second implant element. The method may include engaging the fastener into both the first and second insertion holes of the first implant element and the second implant element and fixedly attaching the fastener to the first coupling portion of the first implant element, and may include engaging the joint head of the shaft portion of the first implant element with the natural articular disk and fossa of the temporomandibular joint of the patient.

Figure 23:
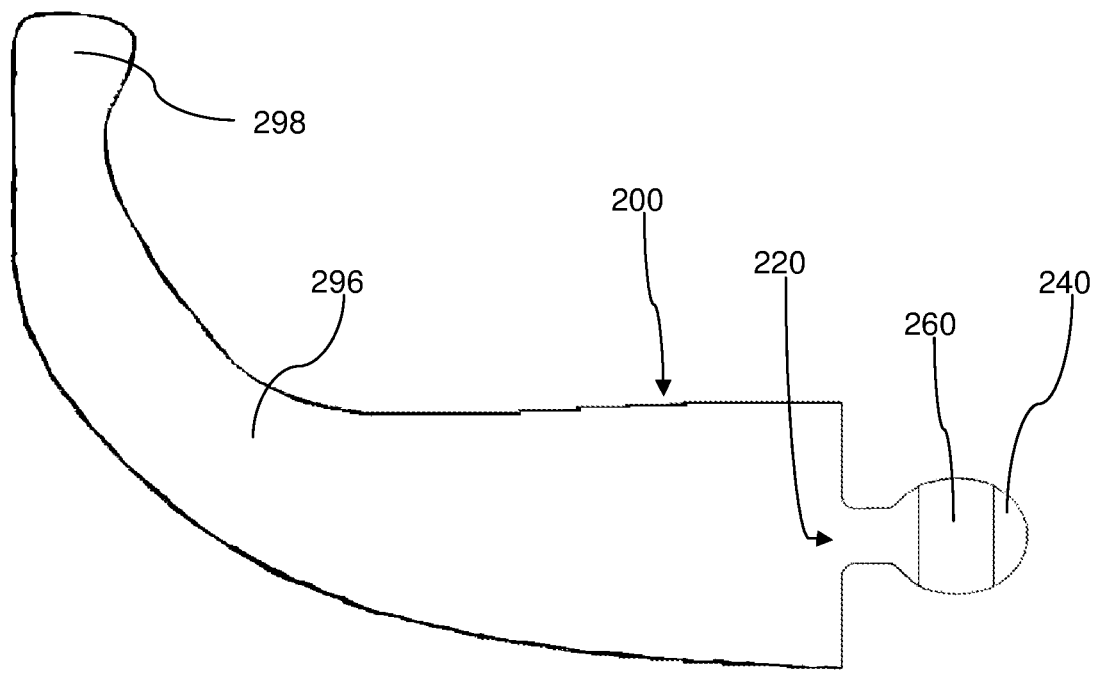
FIG. 23 illustrates a second implant element according to an embodiment of the invention, which can be used for reconstruction of the condyle-ramus region of the mandible.

In a sixth example according to the present invention, the method of surgically repairing a human's mandible may include providing a second implant element which, among others, comprises a curved shaft portion with a joint head as described in this application (e.g. a second implant element which comprises a curved shaft portion 296 with a joint head 298 as for example implemented in the embodiment shown in FIG. 23) and a first implant element (e.g. a first implant element 100 having a first stem portion 180 as shown in, e.g., FIGS. 2 and 12). The method according to the sixth example may further include fixedly attaching the first implant element to a bone portion (e.g. bone portion 6) of a resected portion of the mandible and may include engaging the protrusion of the second implant element and the accommodation recess of the first implant element with each other such that the first and second insertion holes of the first implant element and the second implant element are at least substantially aligned with each other, thereby establishing the coupled condition between the first implant element and the second implant element. The method may then include engaging the fastener into both the first and second insertion holes of the first implant element and the second implant element and fixedly attaching the fastener to the first coupling portion of the first implant element, and may include engaging the joint head of the shaft portion of the second implant element with the natural articular disk and fossa of the temporomandibular joint of the patient.

The step of fixedly attaching a respective implant element to a corresponding bone portion may be performed in the various manners as described in this application for example, the step of fixedly attaching a respective implant element to a corresponding bone portion may include inserting the stem portion of the respective implant element into the corresponding bone portion (e.g. into a predrilled hole therein), wherein the insertion of the stem portion may be performed by use of a corresponding implant element mount (as for example implement like the first implant element mount 400 and the second implant element mount 450 as described in this application). The step of fixedly attaching a respective implant element to a corresponding bone portion may, alternatively or additionally, include attaching a respective implant fixation plate to both the respective implant element (e.g. a corresponding plate attachment hole thereof) and the corresponding bone portion in a manner as described in this application (see for example FIGS. 34 to 37). Further, the step of fixedly attaching a respective implant element to a corresponding bone portion may, alternatively or additionally, include inserting a respective stem fixation screw into a respective stem through-hole for engaging the stem to the surrounding bone portion, wherein the insertion of the stem fixation screw may be performed by use of a corresponding surgical guide (as for example implement like the first surgical guide 500 and the second surgical guide 550 as described in this application). It is to be understood that the method for surgically repairing a mandible according to the present invention is not limited to the above mentioned examples and may include a different order of steps and/or further, such as, but not limited to, the step of resecting a defect portion of the mandible such that a bone portion on a first side of the resected portion and a bone portion on a second side of the resected portion remain.

In the following, specific embodiments of the present invention will be described in further detail with reference to the FIGS. 1 to 37.

In FIG. 1, a mandible endoprosthesis implant 10 according to a first embodiment, which is fixed to the patient's mandible 1, is shown. The mandible endoprosthesis implant 10 serves to bridge a resected portion 2 between the remaining bone portion 6 on a first side of the resected portion 2 and 6' of the mandible body 3 on a second side of the resected portion 2 of the mandible 1. A condyle-ramus region 7 of the mandible 1 comprises the ramus 4 and the condyle 5 of the mandible 1. The resected portion 2 is the result of resection of a portion of the mandible body 3 by surgery which was required due to a mandibular defect, e.g. mandibular trauma, inflammatory diseases or upon resection of tumors, etc. The exact size and location of the resected portion 2 may depend on the type and severity of the mandibular defect. In some cases, it may be necessary to resect a part of the mandible body 3 of the mandible 1 as shown in FIG. 1. In other cases, it may however also be necessary to remove part of the mandible body 3 as well as part of or the entire condyle-ramus region 7 of the mandible 1.

Figure 3:
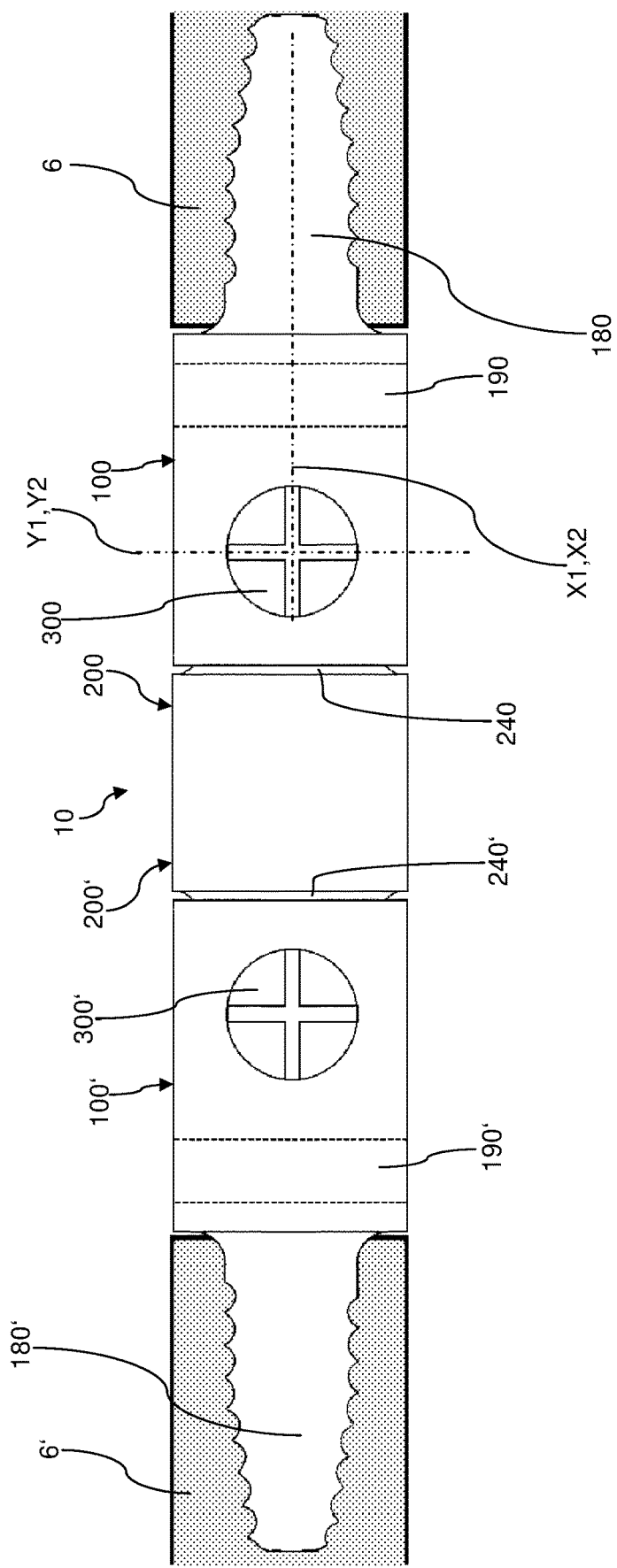
FIG. 3 is a top view of the mandible endoprosthesis implant according to the first embodiment of FIG. 2.

The mandible endoprosthesis implant 10 according to the first embodiment is formed by coupling first and second implant elements 100, 100', 200 and 200' by respective fasteners 300, 300' as shown in FIGS. 1 to 3.

With reference to FIGS. 4 to 7, the principles of the coupling mechanism of the present invention will be exemplarily described in more detail for the mandible endoprosthesis implant 10 according to the first embodiment, wherein it is to be understood that said principles also apply to other mandible endoprosthesis implants 10 according to the present invention which are formed in different configurations by coupling other first and second implant elements than those used in the mandible endoprosthesis implant 10 according to the first embodiment.

As shown in FIGS. 1 to 7, the mandible endoprosthesis implant 10 according to the first embodiment comprises the first implant element 100 having the first stem portion 180 which is fixed to the corresponding bone portion 6, comprises the second implant element 200 which is formed in one piece with the further second implant element 200', and comprises the further first implant element 100' having the further first stem portion 180' which is fixed to the corresponding bone portion 6'. The protrusion 240 of the first implant element 100 and the accommodation recess 140 of the second implant element 200 are engaged with each other. To this end, the head portion 243 of the protrusion 240 is inserted and engaged into the hollow cylindrical portion 143 of the accommodation recess 140 and the neck portion 246 of the protrusion 240 is inserted and engaged into the channel portion 146 of the accommodation recess 140. Thus, a coupled condition between the first and second implant elements 100 and 200 is established. Further, the fastener 300 is engaged into both the first and second insertion holes 160 and 260 and extends along the first element z-axis. The fastener 300 is tightly screwed into the inner thread 163 of the first coupling portion 120 of the first implant element 100 and thereby fixedly attached to the first coupling portion 120 of the first implant element 100. Therefore, the fastener 300 maintains the coupled condition of the first and second implant elements 100 and 200. The countersunk head 303 of the fastener 300 is also received in the countersunk hole portion 166 in a flush manner with the upper surface 105 of the first implant element 100. The further first and further second implant element 100' and 200' are coupled together in the same manner by their corresponding coupling portions and by the respective fastener 300'.

Further, as shown in FIGS. 4 to 7, the first abutment clearance C1 is provided between the first coupling portion 120 and the second coupling portion 220 and the second abutment clearance C2 is provided between the fastener 300 and the second coupling portion 220, when the first and second implant elements 100 and 200 are in their coupled condition and when the fastener 300 is fixedly attached to the first coupling portion 120. The first and second abutment clearances C1 and C2 are provided such that the first and second implant elements 100 and 200 are pivotable relatively to each other about at least one of the first element z-axis Z1 and the first element y-axis Y1 by a maximum angle which may be in a range from 0.01 (optionally from 0.02°) to 10°, optionally from 0.01 (optionally from 0.02°) to 7°, further optionally from 0.01 (optionally from 0.02°) to 1°, depending on the dimensions of the first and second abutment clearances C1 and C2.

By allowing the relative pivoting between the first and second implant elements 100 and 200, external loads (e.g. applied by movement of the mandible) can be distributed between the coupled first and second implant elements in order to avoid stress concentration at the first stem portion 180 fixed to the corresponding bone portion 6 of the patient's mandible. Thus, movement of the first stem portion 180 at interface between the first stem portion 180 and the corresponding bone portion 6 can be reduced due to the distribution of the loads by the relative pivoting between the first and second implant elements 100 and 200. Due to the reduced movement of the first stem portion 180 within the bone portion 6, the risk of loosening of the first stem portion 180 from the bone portion 6 can be reduced and the osseointegration process of the first stem portion 180 with the surrounding bone tissue of the bone portion 6 can take place.

Figure 4:
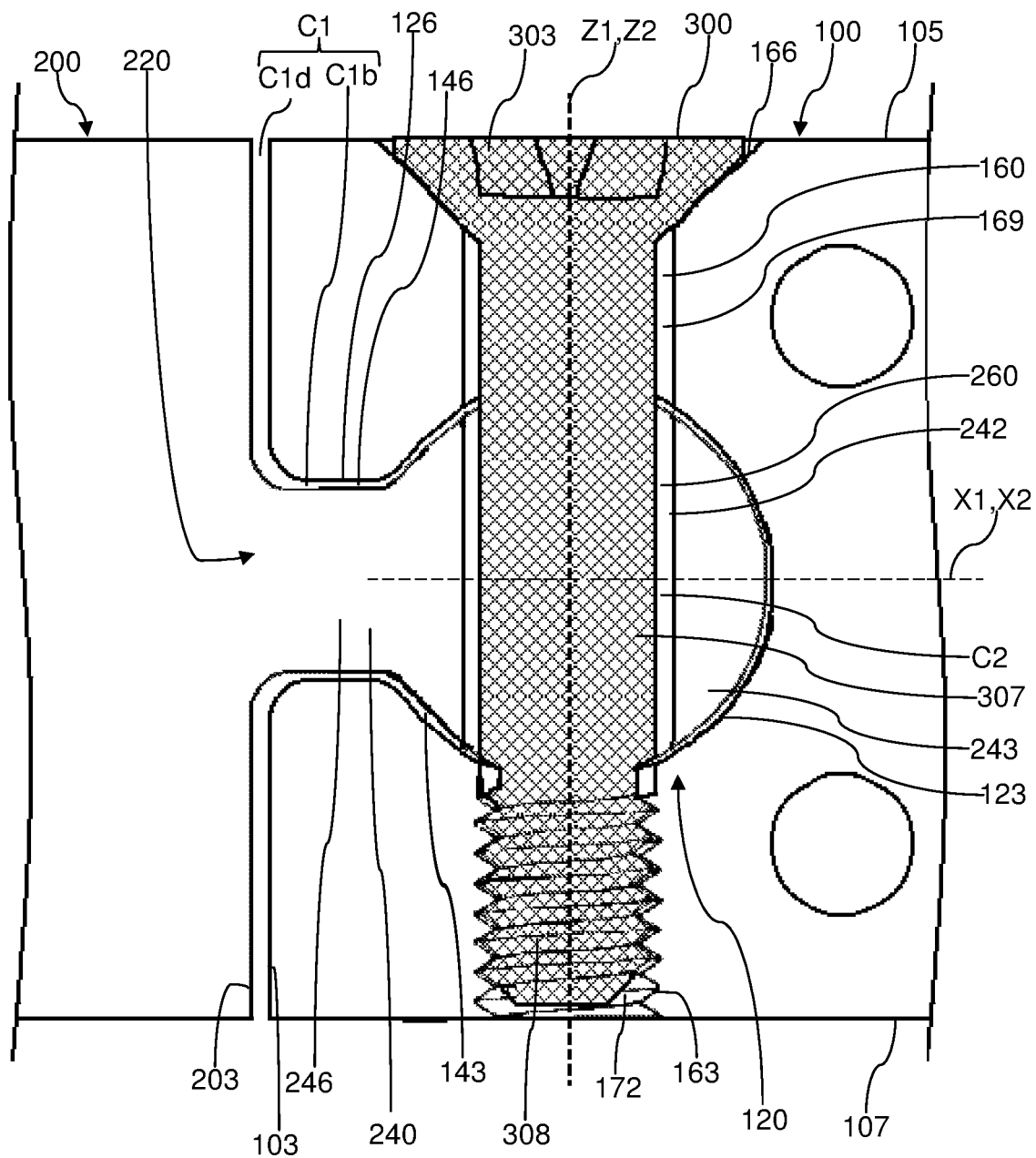
FIG. 4 is a sectional view of the mandible endoprosthesis implant according to the first embodiment along a plane formed by the first element x- and z-axes, illustrating a state in which the first and second implant elements are not pivoted relative to each other about the first element y-axis.
Figure 5:
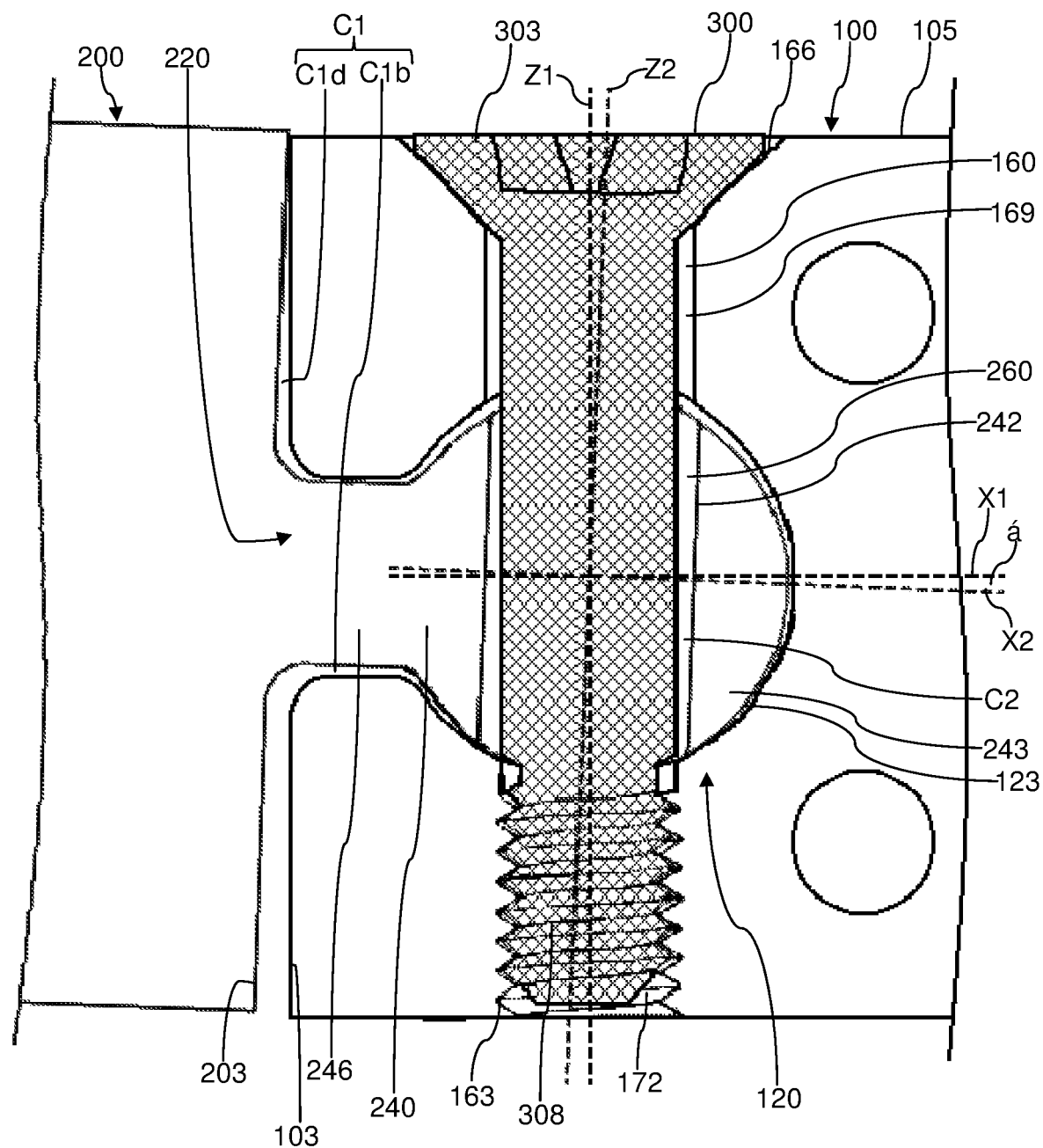
FIG. 5 is a sectional view of the mandible endoprosthesis implant according to the first embodiment along a plane formed by the first element x- and z-axes, illustrating a state in which the first and second implant elements are maximally pivoted relative to each other about the first element y-axis.
Figure 18:
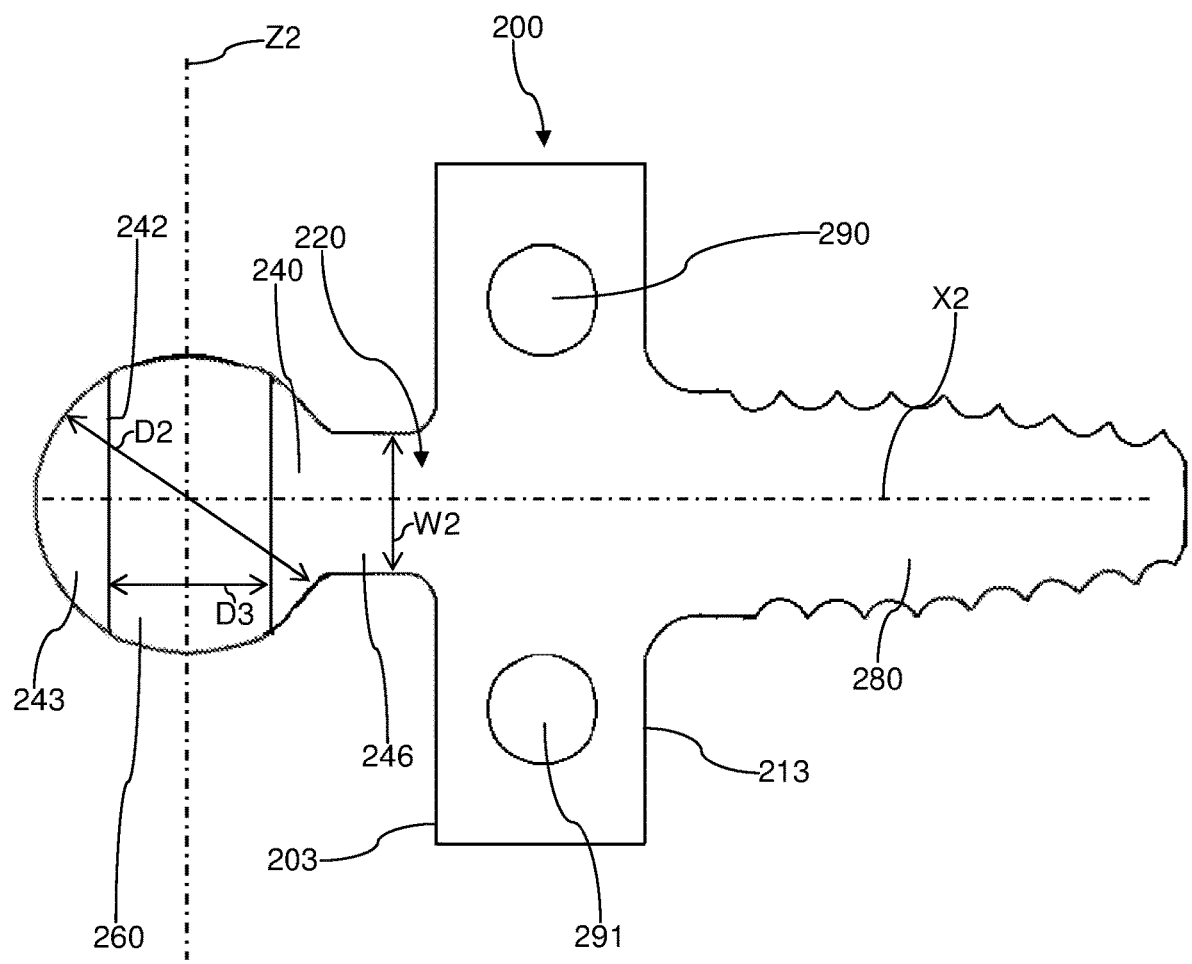
FIG. 18 is a sectional view along the plane formed by the first element x- and z-axis of the second implant element of FIG. 17.
Figure 33:
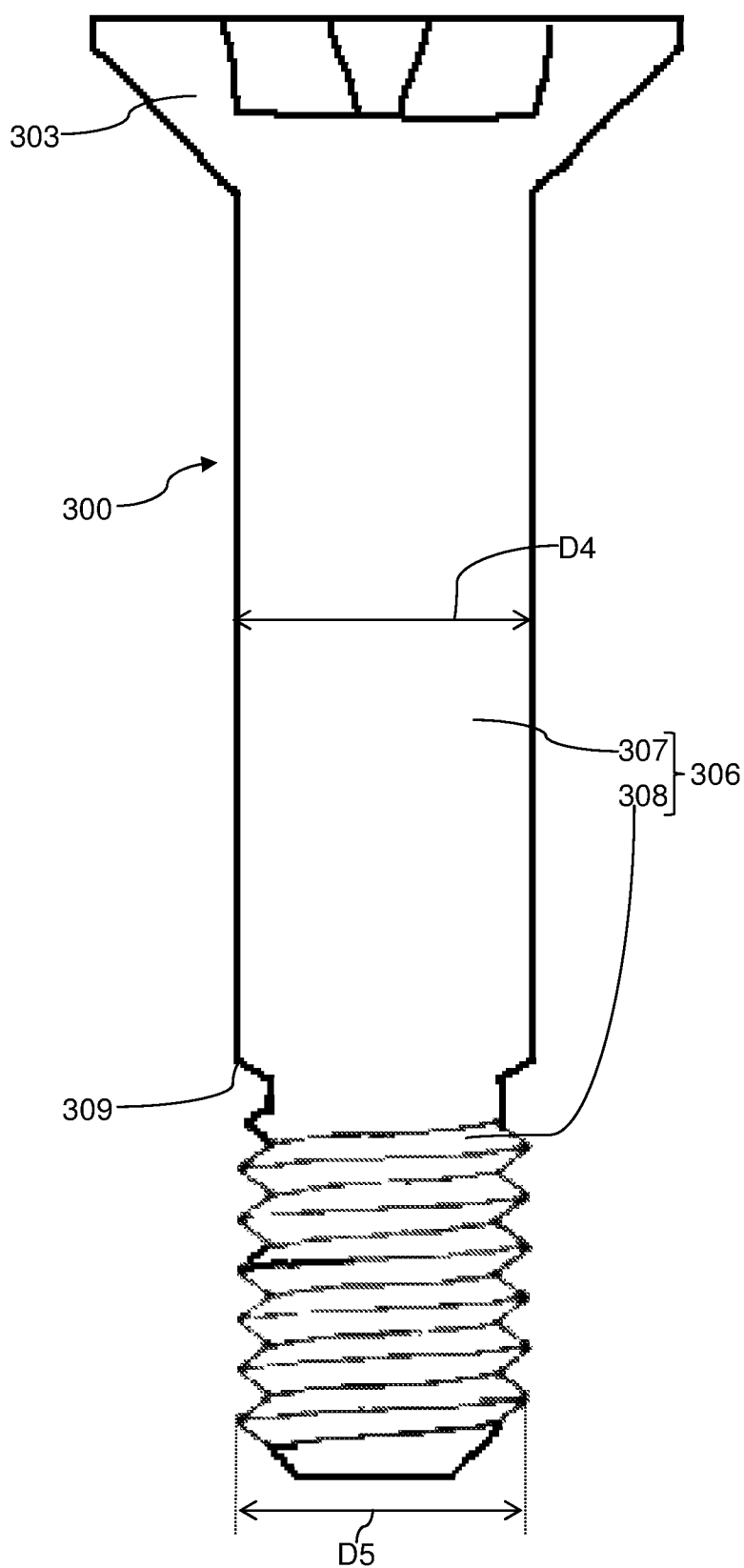
FIG. 33 is a cross-sectional view of a fastener of the mandible endoprosthesis implant according to an embodiment of the present invention.

The second abutment clearance C2 between the fastener 300 and the second coupling portion 220 is the gap between the shaft portion 307 of the fastener 300 and the peripheral surface 242 of the protrusion 240 as shown in FIGS. 4 and 5. Said gap may be formed as a result of different diameters D3 and D4 (as illustrated in FIGS. 18 and 33, respectively) of the second insertion hole 260 and the shaft portion 307 of the fastener 300 and may be accordingly adjusted by increasing or decreasing the difference between the two diameters D3 and D4.

The first abutment clearance C1 comprises the first abutment sub-clearance C1a provided between the protrusion 240 and the accommodation recess 140, and related to the relative pivoting between the first and second implant elements 100 and 200 about the first element z-axis Z1. The first abutment sub-clearance C1a may be the gap between the circumferential edges 245a and 245b of the head portion 243 of the protrusion 240 and an inner wall 123 of the first coupling portion 120, wherein said inner wall 123 defines the hollow cylindrical portion 143 of the accommodation recess 140. The circumferential edges 245a and 245b of the head portion 243 may be chamfered to provide for a larger first abutment sub-clearance C1a (as illustrated in FIG. 19), and the first abutment sub-clearance C1a may be adjusted by appropriately chamfering the circumferential edges 245a and 245b of the head portion 243 so as to increase or decrease the first abutment sub-clearance C1a.

The first abutment clearance C1 also comprises the second abutment sub-clearance C1b provided between the protrusion 240 and the accommodation recess 140, and related to relative pivoting between the first and second implant elements 100 and 200 about the first element y-axis Y1. In FIGS. 4 and 5, the second abutment sub-clearance C1b is the gap which extends between the outer surface of the neck portion 246 of the protrusion 240 and a channel wall 126 of the first coupling portion 120 in a direction parallel to the first element z-axis Z1. Accordingly, the second abutment sub-clearance C1b may be provided by correspondingly designing the neck portion 246 and/or the channel wall 126 to reduce the gap therebetween.

The first abutment clearance C1 further comprises the third abutment sub-clearance C1c provided between the first end face 103 of the first coupling portion 120 and the second end face 203 of the second coupling portion 220 (see FIGS. 6 and 7), and related to relative pivoting between the first and second implant elements 100 and 200 about the first element z-axis Z1. The third abutment sub-clearance C1c may be (e.g., defined by) a portion of the gap which extends between the first end face 103 of the first coupling portion 120 and the second end face 203 of the second coupling portion 220.

Furthermore, the first abutment clearance C1 comprises the fourth abutment sub-clearance C1d provided between the first end face 103 of the first coupling portion 120 and the corresponding second end face 203 of the second coupling portion 220 (see FIGS. 4 to 5), and related to a relative pivoting between the first and second implant elements 100 and 200 about the first element y-axis Y1. The fourth abutment sub-clearance C1d may be (e.g., defined by) another portion of the gap which extends between the first end face 103 of the first coupling portion 120 and the second end face 203 of the second coupling portion 220.

The maximum angle of relative pivoting between the first and second implant elements 100 and 200 can be adjusted by correspondingly designing the dimensions of the abutment sub-clearances C1a to C1d of the first abutment clearance C1 and the dimension of the second clearance C2.

In the mandible endoprosthesis implant 10 according to the first embodiment, the fourth abutment sub-clearance C1d is set so that, during relative pivoting between the first and second implant elements 100 and 200 about the first element Y-axis Y1, the first end face 103 and the corresponding second end face 203 abut against each other at the angle α (which is half of the maximum angle of allowed relative pivoting between the first and second implant elements 100 and 200 about the first element Y-axis Y1 from abutment to abutment), as shown in FIG. 5, while the second abutment sub-clearance C1b is set so that no interference between the protrusion 240 and the accommodation recess 140 (e.g. between the neck portion 246 and the channel wall 126) occurs and the second abutment clearance C2 is set so that no interference between the fastener 300 and the protrusion 240 occurs. FIG. 5 exemplarily illustrates that the first end face 103 and the second end face 203 (e.g. at an upper portion thereof) abut against each other at the angle α when the second implant element 200 pivots about the first element y-axis Y1 in the clockwise direction. Likewise, the first end face 103 and the second end face 203 (e.g. at a lower portion thereof) abut against each other at the angle α when the second implant element 200 pivots about the first element y-axis Y1 in the counter-clockwise direction. Thus the relative pivoting between the first and second implant elements 100 and 200 about the first element Y-axis Y1 is limited to the maximum angle (having the value of two times α) defined by the dimension of the fourth abutment sub-clearance C1d.

Figure 7:
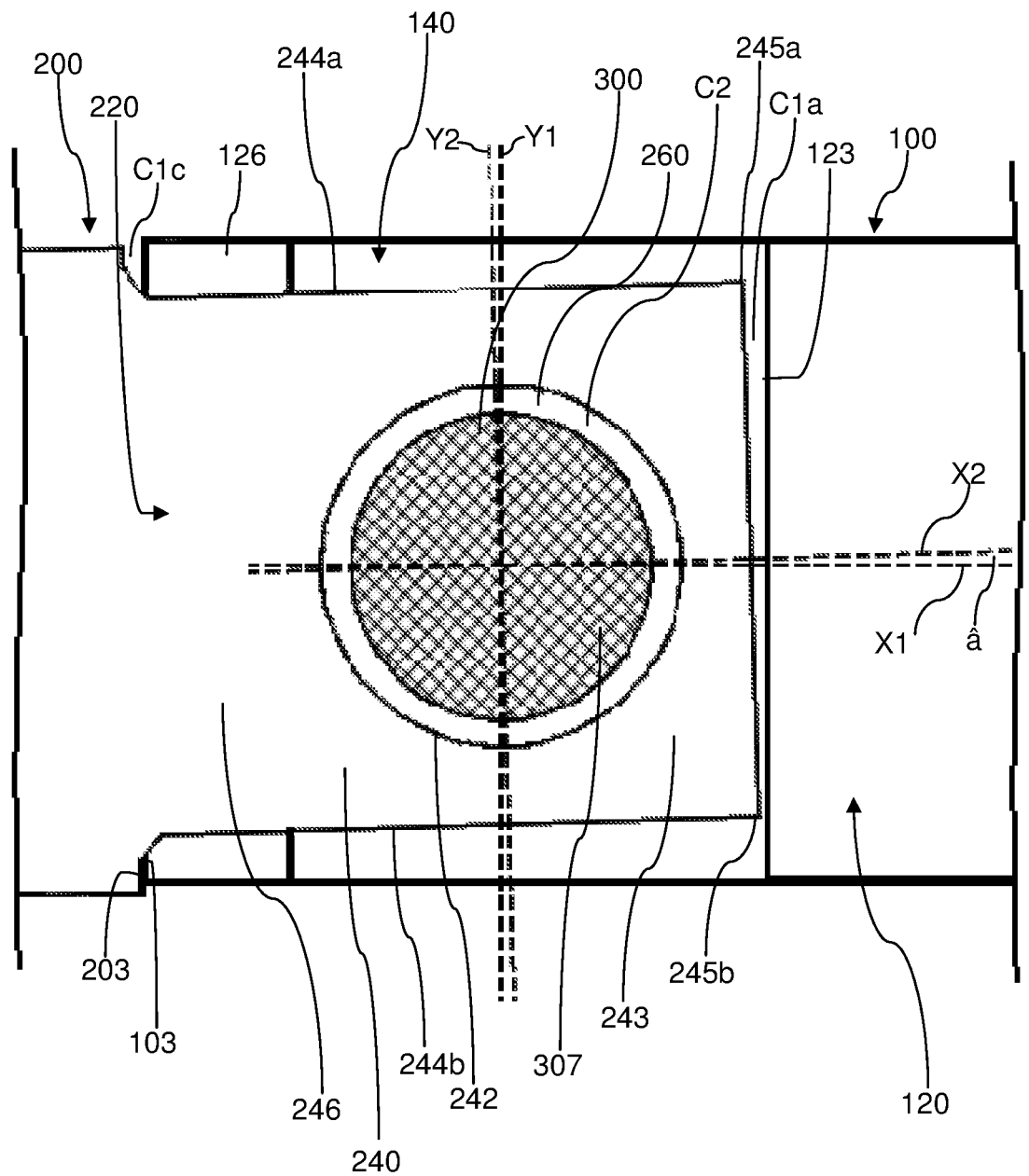
FIG. 7 is a sectional view of the mandible endoprosthesis implant according to the first embodiment along a plane formed by the first element x- and y-axes, illustrating a state in which the first and second implant elements are maximally pivoted relative to each other about the first element z-axis.

Further, the third abutment sub-clearance C1c in this embodiment is set so that, during relative pivoting between the first and second implant elements 100 and 200 about the first element z-axis Z1, the first end face 103 and the corresponding second end face 203 abut against each other at the angle β (which is half of the maximum angle of allowed relative pivoting between the first and second implant elements 100 and 200 about the first element z-axis Z1 from abutment to abutment), as shown in FIG. 7, while the first abutment sub-clearance C1a is set so that no interference between the protrusion 240 and the accommodation recess 140 (e.g. between head portion 243 and the inner wall 123) occurs. FIG. 7 exemplarily illustrates that the first end face 103 and the second end face 203 abut against each other at the angle β when the second implant element 200 pivots about the first element z-axis Z1 in the counter-clockwise direction. Likewise, the first end face 103 and the second end face 203 abut against each other at the angle β when the second implant element 200 pivots about the first element y-axis Y1 in the clockwise direction. Since the fastener 300 extends along the first element z-axis Z1, also no interference between the fastener 300 and the protrusion 240 occurs during the relative pivoting between the first and second implant elements 100 and 200 about the first element z-axis Z1. Thus the relative pivoting between the first and second implant elements 100 and 200 about the first element z-axis Z1 is limited to the maximum angle (having the value of two times β) defined by the dimension of the third abutment sub-clearance C1c.

Figure 6:
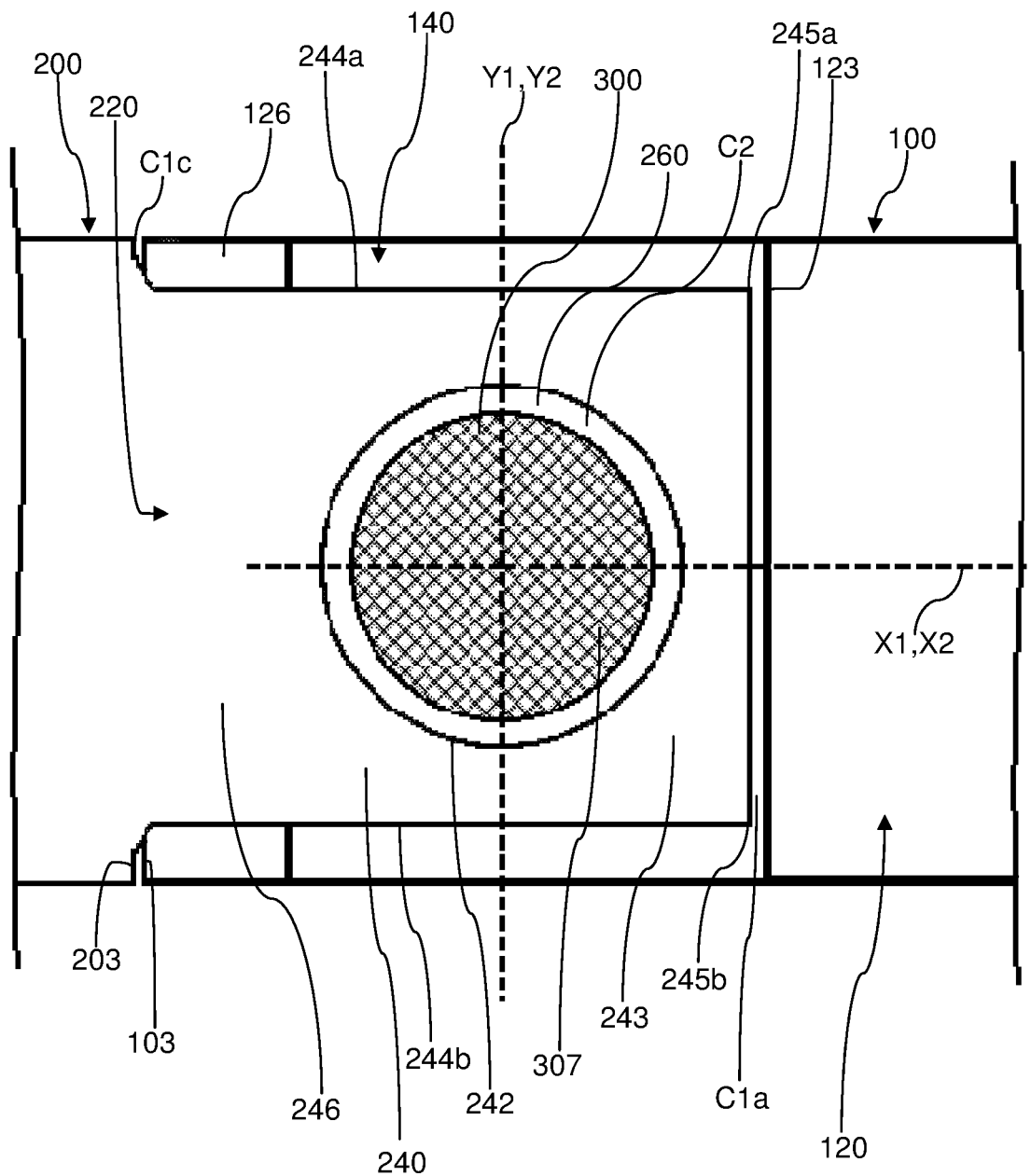
FIG. 6 is a sectional view of the mandible endoprosthesis implant according to the first embodiment along a plane formed by the first element x- and y-axes, illustrating a state in which the first and second implant elements are not pivoted relative to each other about the first element z-axis.

For the convenience and purpose of describing the coupling mechanism of the mandible endoprosthesis implant according to the present invention, FIGS. 4 and 5 illustrate the relative pivoting between the first and second implant elements 100 and 200 about the first element y-axis Y1, while FIGS. 6 and 7 illustrate the relative pivoting between the first and second implant elements 100 and 200 about the first element z-axis Z1. However, it is to be understood that also combination of the relative pivoting about the first element y-axis Y1 and the first element z-axis Z1 are possible by the mandible endoprosthesis implant according to the present invention.

Further, exemplary values for the first abutment clearance C1 (and its abutment sub-clearances C1a to C1d) and the second abutment clearance C2 for a mandible endoprosthesis implant according to the invention will be given together with the maximum angles allowed by such values, wherein the present invention is not limited to these values. In an exemplary mandible endoprosthesis implant according to the invention which allows a maximum angle of at least substantially 2 degree (e.g. 1 degree in the clockwise and 1 degree in the counter-clockwise direction, respectively) for the relative pivoting between the first and second implant elements 100 and 200 about the first element y-axis Y1 from abutment to abutment and which allows a maximum angle of at least substantially 2 degree (e.g. 1 degree in the clockwise and 1 degree in the counter-clockwise direction, respectively) for the relative pivoting between the first and second implant elements 100 and 200 about the first element z-axis Z1 from abutment to abutment, the fourth abutment sub-clearance C1$d$ and the third abutment sub-clearance C1$c$ may have each a value of at least substantially 0.1 mm, and the second abutment sub-clearance C1$b$ may have a value of at least substantially 0.2 mm, while the first abutment sub-clearance C1$a$ may have a value of at least substantially 0.05 mm. In a further exemplary mandible endoprosthesis implant according to the invention which allows a maximum angle of at least substantially 6 degree (e.g. 3 degree in the clockwise and 3 degree in the counter-clockwise direction, respectively) for the relative pivoting between the first and second implant elements 100 and 200 about the first element y-axis Y1 from abutment to abutment and which allows a maximum angle of at least substantially 6 degree (e.g. 3 degree in the clockwise and 3 degree in the counter-clockwise direction, respectively) for the relative pivoting between the first and second implant elements 100 and 200 about the first element z-axis Z1 from abutment to abutment, the fourth abutment sub-clearance C1$d$ and the third abutment sub-clearance C1$c$ may have each a value of at least substantially 0.25 mm, and the second abutment sub-clearance C1$b$ may have a value of at least substantially 0.31 mm, while the first abutment sub-clearance C1$a$ may have a value of at least substantially 0.1 mm. In the further exemplary a mandible endoprosthesis implant which allows 3 degree for the relative pivoting between the first and second implant elements 100 and 200 about the first element z-axis Z1, the circumferential edges of the head portion and/or of the neck portion may be chamfered as described in this application.

Although not particularly necessary in the present invention, it may also be contemplated to rigidly fix at least some or all of the implant elements of the mandible endoprosthesis implant of the present invention together (i.e. to fix at least some or all of the implant elements such that relative pivoting in the mandible endoprosthesis implant of the present invention is prevented) after a certain time (e.g. one month) has elapsed from the time of implantation. Referring exemplarily to FIGS. 1 to 3, after a certain has elapsed and sufficient osseointegration of the stem portions 180 and 180' into the bone portions 6 and 6' has occurred, respectively, it may be decided to rigidly fix the first implant element 100 and the second implant element 200 together and to fix the further first implant elements 100 and the further second implant elements 200' together. The rigid connection (which may also be referred to as "non-pivotable connection") between adjacent implant elements may be achieved, for example, by the use of rigid element connection plates which are attached by the use of respective screws to each of adjacent implant elements and which thus connect adjacent implant elements with each other. Further, the adjacent implant elements to be rigidly fixed together may comprise additional holes (e.g. through-holes) for attaching the rigid element connection plates by the use of screws to the adjacent implant elements to be rigidly fixed together. Still referring exemplarily to FIGS. 1 to 3, it is to be understood that also the plate attachment holes 190, 191, 190', 191 may be used for attaching rigid element connection plate(s) to rigidly fix the first implant element 100 to the further first implant element 100', wherein the rigid element connection plate(s) then extend over (e.g. span) the monolithically formed second and further first implant element 200 and 200' of the mandible endoprosthesis implant 10 shown in FIGS. 1 to 3. It is to be understood that a variety of different devices and methods for rigidly fixing the implant elements of a mandible endoprosthesis implant according to the invention together may be used and the present invention is not limited to the aforementioned rigid element connection plates.

Figure 8:
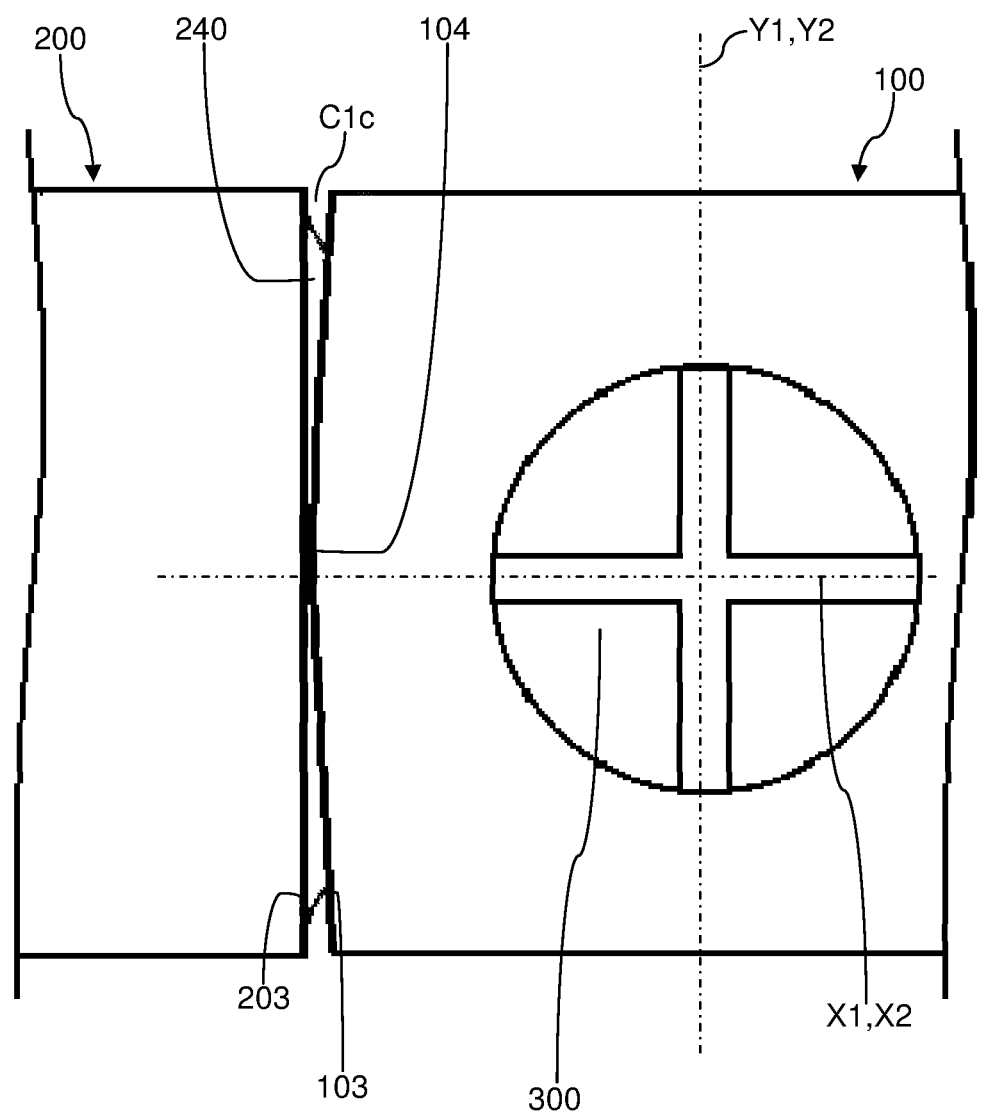
FIG. 8 is a top view of a variation of the mandible endoprosthesis implant according to the first embodiment.
Figure 9:
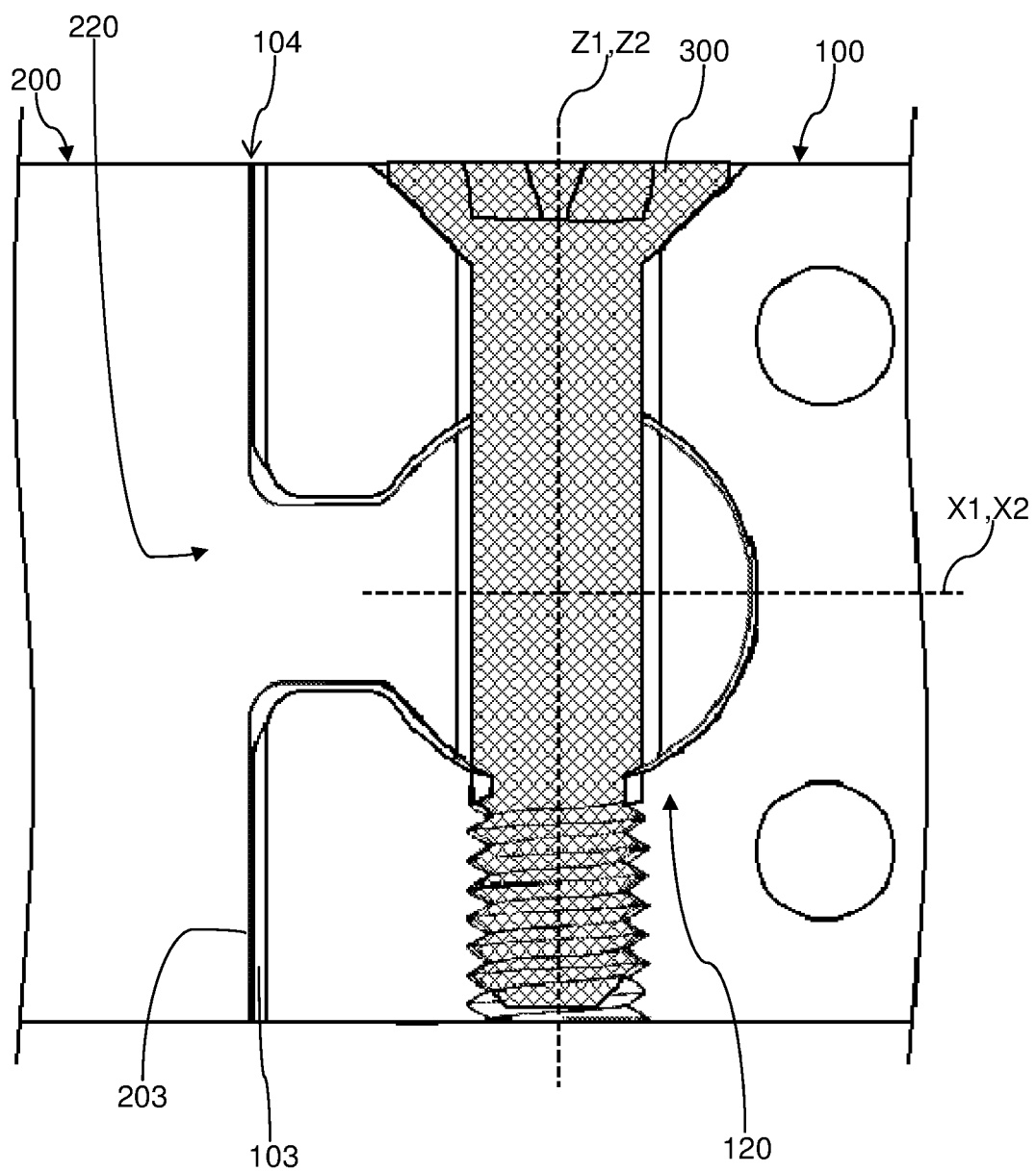
FIG. 9 is a sectional view of the variation of the mandible endoprosthesis implant according to the first embodiment along a plane formed by the first element x- and z-axes.

A variation of the mandible endoprosthesis implant 10 according to the first embodiment is illustrated in FIGS. 8 and 9.

In the variation of the mandible endoprosthesis implant 10 according to the first embodiment, relative pivoting between the first and second implant elements 100 and 200 about the first element y-axis Y1 is at least substantially prevented and relative pivoting between the first and second implant elements 100 and 200 about the first element z-axis Z1 is allowed. As can be seen in the top view of FIG. 8, the first end face 103 of the first implant element 100 of this variation is formed with a curved profile (e.g. with an at least substantially triangular profile) when viewed from above (e.g. in a cross section transverse to the first element z-axis Z1). The curved profile of the first end face 103 of the first implant element 100 of this variation has an apex 104 on the first element x-axis X1 so that the fourth abutment sub-clearance C1$d$ is at least substantially zero in the coupled condition of the first and second implant elements 100 and 200 (and thus C1$d$ is not illustrated in FIGS. 8 and 9). For example, the first and second end faces 103 and 203 are immediately in contact at the apex 104 of the first end face 103 in the coupled condition of the first and second implant elements 100 and 200 (as shown in FIG. 9) so that relative pivoting between the first and second implant elements 100 and 200 about the first element y-axis Y1 is entirely or at least substantially prevented. On the other hand, the curved profile allows relative pivoting between the first and second implant elements 100 and 200 about the first element z-axis Z1.

It is to be understood that various other variations of the mandible endoprosthesis implant 10 according to the first embodiment, in which relative pivoting between the first and second implant elements 100 and 200 about at least one of its axes is at least substantially prevented by accordingly reducing at least one of the first abutment sub-clearance C1$a$, the second abutment sub-clearance C1$b$, the third abutment sub-clearance C1$c$, the fourth abutment sub-clearance C1$d$ and the second abutment clearance C2 close to zero, can be contemplated in view of the teachings of the present invention.

Figure 11:
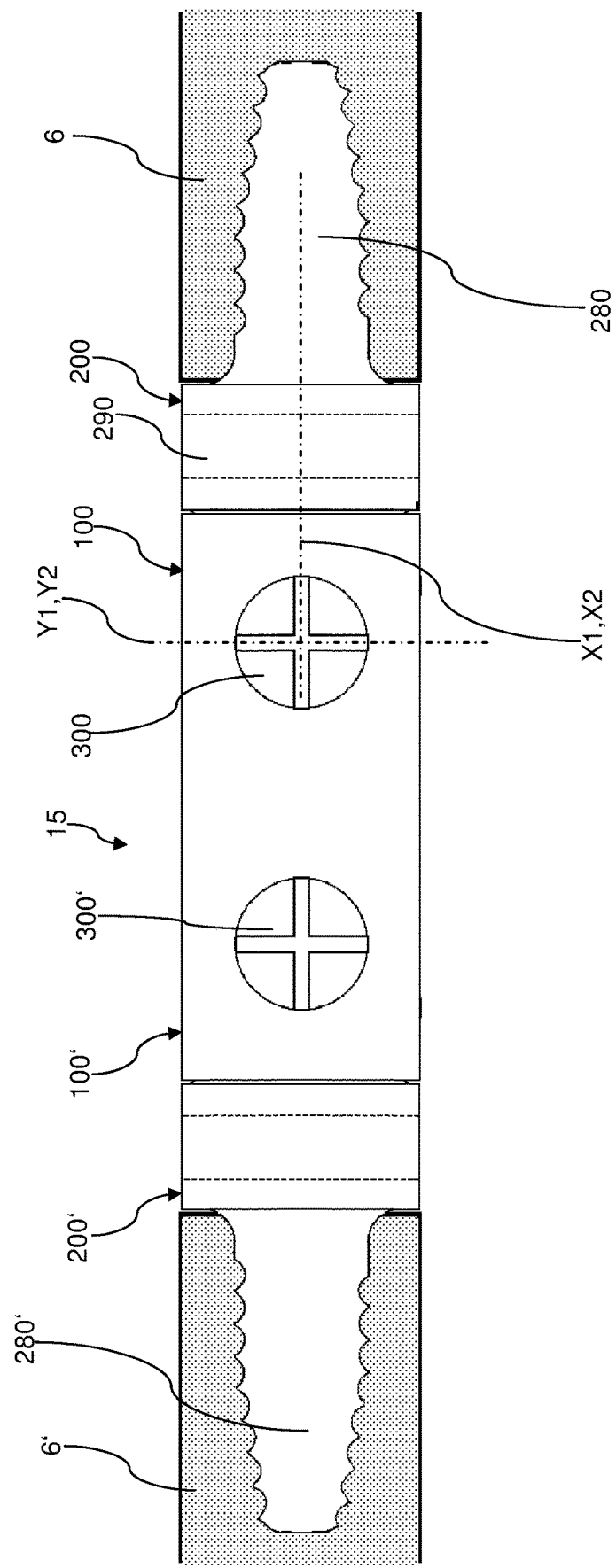
FIG. 11 is a top view of the mandible endoprosthesis implant according to the second embodiment of FIG. 10.

A mandible endoprosthesis implant 15 according to a second embodiment is shown in FIGS. 10 and 11. The mandible endoprosthesis implant 15 according to the second embodiment is also formed by coupling first and second implant elements 100, 100', 200 and 200' by respective fasteners 300, 300', wherein the respective first and second implant elements 100, 100', 200 and 200' have configurations which differ from those used in the mandible endoprosthesis implant 10 according to the first embodiment.

The mandible endoprosthesis implant 15 according to the second embodiment comprises a second implant element 200 having a second stem portion 280, comprises a first implant element 100 which is formed in one piece with a further first implant element 100', and comprises a further second implant element 200' having a further second stem portion 280'. The first and second implant elements 100 and 200 are coupled with each other by their corresponding coupling portions and by the fastener 300 in the same manner as described above for the mandible endoprosthesis implant 10 according to the first embodiment, and the further first and further second implant elements 100' and 200' are also coupled together in the same manner by their corresponding coupling portions and by the respective fastener 300'.

Since the principles of the coupling mechanism in the mandible endoprosthesis implant 15 according to the second embodiment are identical to those for the mandible endoprosthesis implant 10 according to the first embodiment, a separate description thereof will be omitted.

In FIGS. 12 to 21, embodiments of the first and second implant elements 100 and 200 are shown which are used for fixing the mandible endoprosthesis implant of the present invention to the bone portion 6, 6' of the mandible 1 (e.g. to a corresponding bone end portion or bone stump of the mandible body 3 which remains after resection of a portion 2 of the mandible 1).

Figure 13:
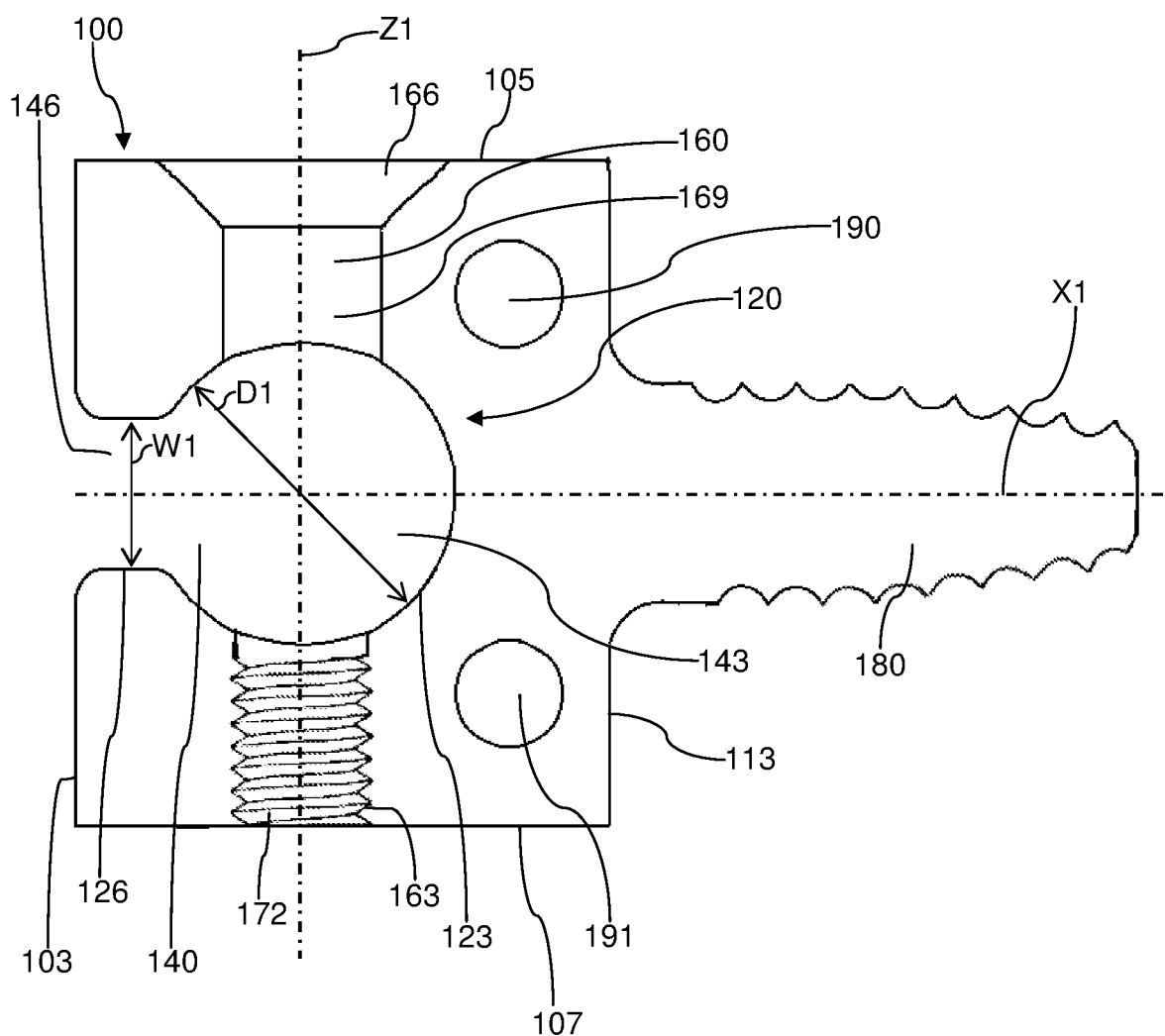
FIG. 13 is a sectional view along the plane formed by the first element x- and z-axis of the first implant element of FIG. 12.
Figure 14:
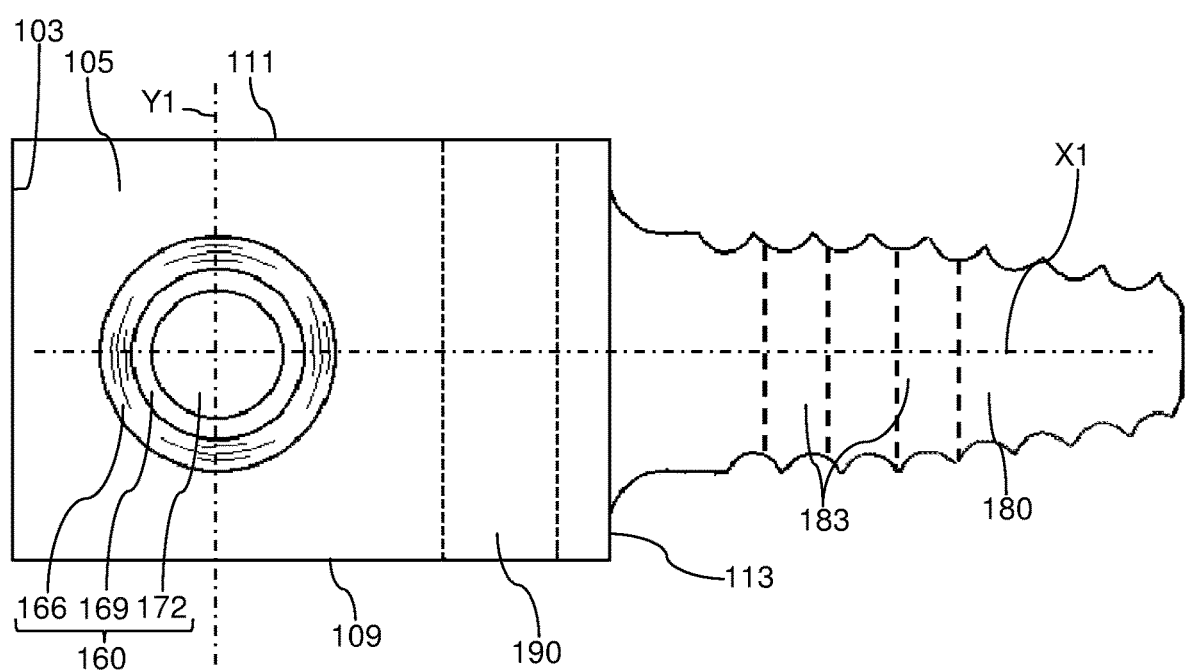
FIG. 14 is a top view of the view of the first implant element of FIG. 12.

In FIGS. 12 to 16, an exemplary first implant element 100 according to the present invention is shown. FIG. 12 is a perspective view, FIG. 13 is a sectional view along the plane formed by the first element x- and z-axis X1 and Z1, and FIG. 14 is a top view of the exemplary first implant element 100. Further, FIGS. 15 and 16 are a sectional view and a top view, respectively, of an exemplary first implant element 100 which comprises two first bone screw through-holes 193.

The exemplary first implant element 100 extends along the first element x-axis X1, along the first element y-axis Y1 which extends transverse to the first element x-axis X1, and along the first element z-axis Z1 which extends transverse to the first element x- and z-axes X1 and Y1 and may have a block shaped body. The exemplary first implant element 100 comprises the first coupling portion 120 which comprises the accommodation recess 140 and the first insertion hole 160.

The accommodation recess 140 is provided within the first end face 103 of the first implant element 100 and extends from said first end face 103 along the first element x-axis X1 into the first implant element 100. The first end face 103 may extend at least substantially parallel to the plane formed by the first element y- and z-axes Y1 and Z1. The accommodation recess 140 comprises the hollow cylindrical portion 143 defined by the inner wall 123 of the first coupling portion 120 and comprises the hollow channel portion 146 defined by the channel wall 126 of the first coupling portion 120.

In the exemplary first implant element 100 of FIGS. 12 to 14, the first insertion hole 160 extends along the first element z-axis between an upper surface 105 and an opposite lower surface 107 of the first implant element 100. The upper surface 105 and the lower surface 107 of the first implant element 100 may extend at least substantially parallel to the plane formed by the first element x- and y-axes X1 and Y1. The first insertion hole 160 comprises the first passage 169 and the second passage 172 which are formed in the first coupling portion 120 on opposite sides of the accommodation recess 140. For example, the first passage 169 may connect the upper surface 105 with the accommodation recess 140 (e.g. with the hollow cylindrical portion 143 thereof) and the second passage 172 may connect the lower surface 107 with the accommodation recess 140 (e.g. with the hollow cylindrical portion 143 thereof). The first passage 169 of the first insertion hole comprises the countersunk hole portion 166. An inner thread 163 is formed in the first insertion hole 160. In the exemplary first implant element 100 of FIGS. 12 to 14, the inner thread 163 is formed within the second passage 172 of the first insertion hole 160. However, it is also possible that, alternatively or additionally, an inner thread is formed within the first passage 169 (e.g. below and adjacent to the countersunk hole portion 166 of the first passage 169).

The exemplary first implant element 100 of FIGS. 12 to 14 further includes the elongated first stem portion 180 as described in this application. The first stem portion 180 extends along the first element x-axis X1 from an opposite end face 113 of the first implant element 100 (e.g. from an opposite end face 113 of the block shaped body of the first implant element 100), the opposite end face 113 being disposed opposite to the first end face 103. The first stem portion 180 is shaped such that it can be inserted into a first bone portion (e.g. bone portion 6, 6') of a patient's mandible 1 (e.g. inserted into a predrilled hole in the cancellous bone region of the first bone portion) in order to fixedly attach the first implant element 100 to said first bone portion. In this embodiment, the first stem portion 180 is provided with an outer thread which is to be threadedly engaged with the first bone portion. The first stem portion 180 allows the fixation of the first implant element 100 to the first bone portion by osseointegration that occurs at the first stem portion 180. As schematically shown in FIG. 14 with dashed lines, the first stem portion 180 may include one or more first stem through-holes 183 as described in this application. Further, the opposite end face 113 of the first implant element 100 may come into contact with the first bone portion upon fixation of the first implant element 100 to the first bone portion by the first stem portion 180. In order to promote osseointegration at the opposite end face 113 of the first implant element 100, said end face 113 may include topological surface modification(s) thereon and/or include active material(s) coated thereon. Said surface modification(s) and active material(s) may be the same or similar surface modification(s) and active material(s) for promoting osseointegration as mentioned hereinbefore.

The exemplary first implant element 100 of FIGS. 12 to 14 also comprises an upper first plate attachment hole 190 and a lower first plate attachment hole 191. The upper and lower first plate attachment holes 190 and 191 comprise a thread for establishing a threaded engagement with a corresponding plate attachment screw 63a and 63b. The upper and lower first plate attachment holes 190 and 191 extend in a direction parallel to the first element y-axis Y1 from a (e.g. first) lateral surface 109 to the opposite (e.g. second) lateral surface 111 of the first implant element 100, the lateral surfaces 109 and 111 extending at least substantially parallel to the plane formed by the first element x- and z-axes X1 and Z1. The upper and lower first plate attachment holes 190 and 191 may extend entirely through the first implant element 100 as shown in FIG. 14, but are not limited thereto and may also extend only partially through the first implant element 100. The upper and lower first plate attachment holes 190 and 191 are arranged between the first coupling portion 120 and the first stem portion 180. Further, the upper and lower first plate attachment holes 190 and 191 are disposed on opposite sides with respect to the first element x-axis X1. The upper first plate attachment holes 190 is for example formed through the first implant element 100 at an upper portion of the first implant element 100 which is located above a lower portion of the first implant element 100 through which the lower first plate attachment holes 191 is formed.

In addition to or as an alternative to one or both of the upper and lower first plate attachment holes 190 and 191, the exemplary first implant element 100 may comprise one or more first bone screw through-holes 193 as described in this application. For example, the exemplary first implant element 100 as shown in FIGS. 15 and 16 comprises two first bone screw through-holes 193 in a lower portion of the first implant element 100 (e.g. at a level below the stem portion 180) instead of the lower first plate attachment holes 191. The first bone screw through-holes 193 in FIGS. 15 and 16 extend from the first end face 103 to the opposite end face 113 of the first implant element 100. Further, the first bone screw through-holes 193 are disposed adjacent to the first insertion hole 160 within the first implant element 100. In other words, the first bone screw through-hole 193 passes through the first implant element 100 without intersecting the first insertion hole 160.

Figure 20:
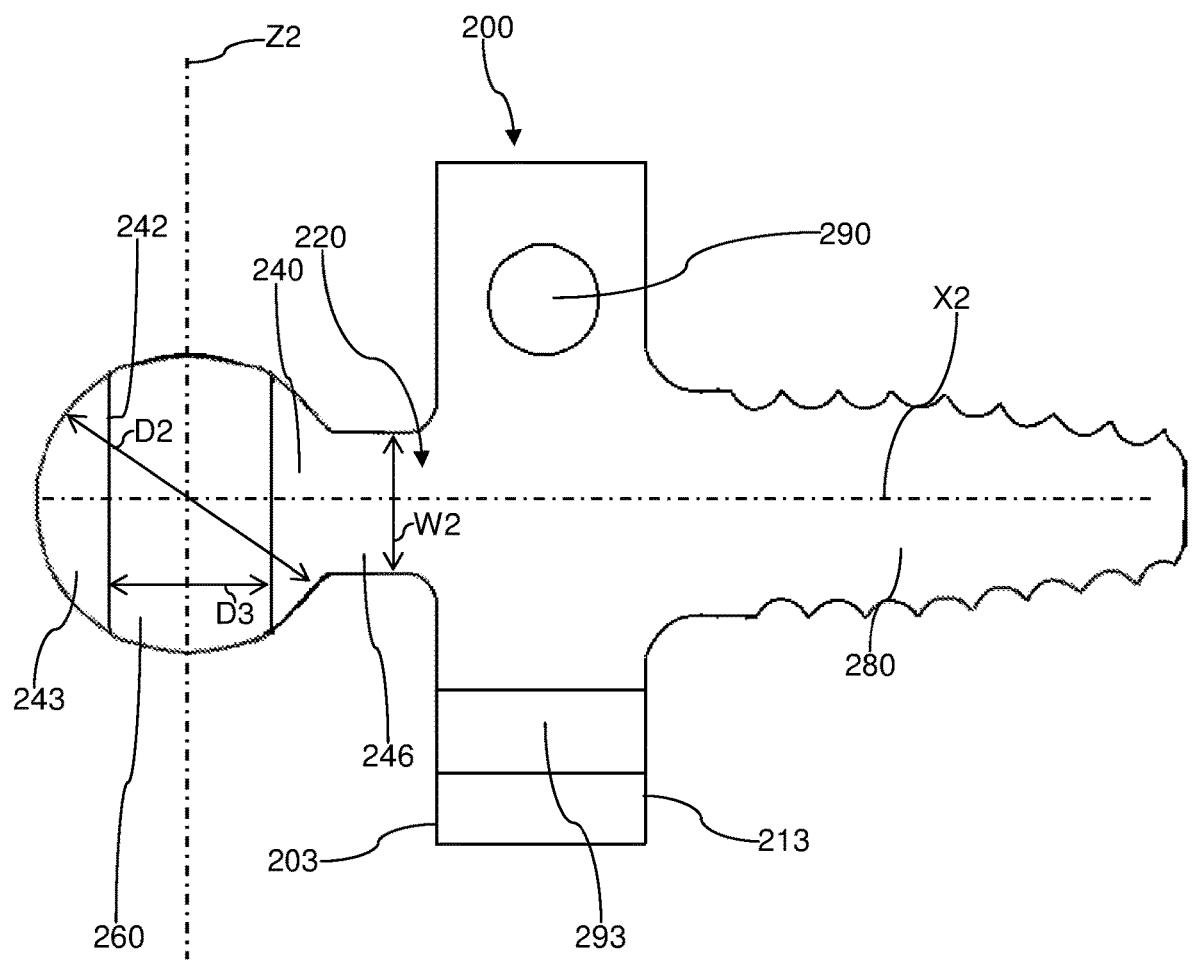
FIGS. 20 and 21 are a sectional view and a top view, respectively, illustrating a second implant element with a stem portion according to an embodiment of the invention, which further comprises first bone screw through-holes instead of a lower plate attachment hole.

In FIGS. 17 to 21, an exemplary second implant element 200 according to the present invention is shown. FIG. 17 is a perspective view, FIG. 18 is a sectional view along a plane formed by the first element x- and z-axis X1 and Z1, and FIG. 19 is a top view of the exemplary second implant element 200. Further, FIGS. 20 and 21 are a sectional view and a top view, respectively, of an exemplary second implant element 200 which comprises two second bone screw through-holes 293.

The exemplary second implant element 200 extends along the second element x-axis X2, the second element y-axis Y2 which extends transverse to the second element x-axis X2, and the second element z-axis Z2 which extends transverse to the second element x- and z-axes X2 and Y2 and may have a block shaped body. The exemplary second implant element 200 comprises the second coupling portion 220 which comprises the protrusion 240 and the second insertion hole 260.

The protrusion 240 extends from the second end face 203 of the second implant element 200 and extends from said second end face 203 along the second element x-axis X2. The second end face 203 may extend at least substantially parallel to the plane formed by the second element y- and z-axes Y2 and Z2. Further, the protrusion 240 comprises the at least substantially cylindrical head portion 243 and the elongated neck portion 246 as described in this application. The neck portion 246 connects the head portion 243 with a remainder of the second implant element 200 (e.g. with the block shaped body of the second implant element 200).

As specifically shown in FIG. 19, the first and the second cylinder end faces 244a and 244b of the head portion 243 have a chamfered circumferential edge 245a and 245b, respectively. Further, the neck portion 246, on its first and second longitudinal ends 247a and 247b, may respectively have upper and lower chamfered edges 248a and 248b smoothly transitioning into the corresponding chamfered circumferential edge 245a and 245b. However, the circumferential edges 245a and 245b of the cylinder end faces 244a and 244b may also be provided without being chamfered as shown in FIGS. 6 and 7.

In the exemplary second implant element 200 of FIGS. 17 to 21, the second insertion hole 260 comprises a diameter D3 and extends along the second element z-axis Z2 through the protrusion 240. As specifically shown in FIG. 18, the peripheral surface 242 of the protrusion 240 defines the circumferential portion of the second insertion hole 260 and thus the diameter D3 of the second insertion hole 260.

The exemplary second implant element 200 of FIGS. 17 to 21 further includes an elongated second stem portion 280. The second stem portion 280 extends along the second element x-axis X2 from an opposite end face 213 of the second implant element 200 which is disposed opposite to the second end face 203. The second stem portion 280 is shaped such that it can be inserted into a second bone portion (e.g. bone portion 6, 6' as shown in FIGS. 10 and 11) of a patient's mandible 1 (e.g. inserted into a predrilled hole in the cancellous bone region of the second bone portion) in order to fixedly attach the second implant element 200 to said second bone portion. In this embodiment, the second stem portion 280 is provided with an outer thread which is to be threadedly engaged with the second bone portion (e.g. bone portion 6, 6'). Similar to the first stem portion 180, the second stem portion 280 allows the fixation of the second implant element 200 to the second bone portion by osseointegration that occurs at the second stem portion 280. Further, the second stem portion 280 may also include one or more second stem through-holes 283 which are formed like the first stem through-holes 183 described above. Similar to the opposite end face 113 of the first implant element 100, the opposite end face 213 of the second implant element 200 may come into contact with the second bone portion upon fixation of the first implant element 200 to the first bone portion by the second stem portion 280 and may thus also include topological surface modification(s) thereon and/or include active material(s) coated thereon. Said surface modification(s) and active material(s) may be the same or similar surface modification(s) and active material(s) for promoting osseointegration as mentioned hereinbefore.

The exemplary second implant element 200 of FIGS. 17 to 19 also comprises an upper and a lower threaded second plate attachment holes 290 and 291. The upper and lower second plate attachment holes 290 and 291 extend in a direction parallel to the second element y-axis Y2 from a (e.g. first) lateral surface 209 to the opposite (e.g. second) lateral surface 211 of (e.g. the block shaped body of) the second implant element 200, the lateral surfaces 209 and 211 extending at least substantially parallel to the plane formed by the second element x- and z-axes X2 and Z2. The upper and lower second plate attachment holes 290 and 291 may extend entirely through the second implant element 200, but are not limited thereto and may also extend only partially through the second implant element 200. The upper and lower second plate attachment holes 290 and 291 are arranged between the second coupling portion 220 and the second stem portion 280. Further, the upper and lower second plate attachment holes 290 and 291 are disposed on opposite sides with respect to the second element x-axis X2. The upper second plate attachment holes 290 is for example formed through the second implant element 200 at an upper portion of the second implant element 200 which is located above a lower portion of the second implant element 200 through which the lower second plate attachment holes 291 is formed.

In addition to or as an alternative to one or both of the upper and lower second plate attachment holes 290 and 291, the exemplary second implant element 200 may comprise one or more second bone screw through-holes 293 as described in this application. For example, the exemplary second implant element 200 as shown in FIGS. 20 and 21 comprises a second bone screw through-hole 193 in a lower portion of the second implant element 200 (e.g. at a level below the second stem portion 280) instead of the lower second plate attachment holes 291. The second bone screw through-hole 293 in FIGS. 20 and 21 extends from the second end face 203 to the opposite end face 213 of the second implant element 200.

In FIGS. 22 and 23, embodiments of first and second implant elements 100 and 200 are illustrated, which can be used for reconstruction of the condyle-ramus region 7 of the mandible 1.

FIG. 22 illustrates an embodiment of a first implant element 100 which comprises the first coupling portion 120 as described in this application and comprises the curved shaft portion 196 which extends from the first coupling portion 120 in a curved shape which corresponds to the angle and contour of the mandible's ramus region 4 to be replaced by the first implant element 100. An end of the shaft portion 196 which is located distally from the first coupling portion 120 comprises the joint head 198.

Further, FIG. 23 illustrates an embodiment of a second implant element 200 which comprises a second coupling portion 220 as described in this application and comprises the curved shaft portion 296 which extends from the second coupling portion 220. Similar to the curved shaft portion 196 of the first implant element 100 in FIG. 22, the curved shaft portion 296 of the second implant element 200 in FIG. 23 has a curved shape which corresponds to the angle and contour of the mandible's ramus region 4 to be replaced by the second implant element 200. An end of the shaft portion 296 which is located distally from the second coupling portion 220 comprises the joint head 298.

The joint heads 198 and 298 are shaped to resemble the condyle 5 so that they can engage with the natural articular disk and fossa of the temporomandibular joint, respectively. The shaft portions 196 and 296 of the embodiment in FIGS. 22 and 23 may include topological surface modification(s) and/or may include active material(s) on their respective outer surfaces (e.g. coated thereon) to promote adhesion of soft tissue to the shaft portions 196 and 296, respectively.

In FIGS. 24 to 30, embodiments of first and second implant elements 100 and 200, which are formed in one piece with further first and/or second implant elements 100' and 200', are shown. The embodiments of first and second implant elements 100 and 200 in FIGS. 24 to 30*c* are also referred to as "monolithically formed implant elements" in this application. The embodiments shown in FIGS. 24 to 30*c* can be used as intermediate implant elements to bridge the resected region of the mandible by interconnecting implant elements that are fixed to bone portions (such as those shown in FIGS. 12 to 21) with each other and/or with implant elements that are used for reconstruction of the condyle-ramus region 7 (such as those shown in FIGS. 22 and 23).

According to an embodiment as shown in FIGS. 24 and 25, the first implant element 100 is formed in one piece (i.e. monolithically) with a further first implant element 100'. FIG. 24 shows a sectional view along the plane formed by the x- and z-axes of the implant elements and FIG. 25 is a top view of the first implant element 100 which is formed in one piece with the further first implant element 100'.

The first implant element 100 in FIGS. 24 and 25 comprises the first coupling portion 120 which comprises the accommodation recess 140 and the first insertion hole 160 which are formed as described in this application. The further first implant element 100' is formed like the first implant 100 as described in this application and extends along its corresponding further first element x-axis X1', along its corresponding further first element y-axis Y1' which extends transverse to the further first element x-axis X1', and along its corresponding further first element z-axis Z1' which extends transverse to the further first element x- and z-axes X1' and Y1'. The further first implant element 100' comprises the first coupling portion 120' which comprises the accommodation recess 140' and the first insertion hole 160', and the accommodation recess 140' and the first insertion hole 160' are formed like the accommodation recess 140 and the first insertion hole 160 as described in this application, respectively. The accommodation recess 140' of the further first implant element 100' and the accommodation recess 140 of the first implant element 100 are oppositely arranged. In the embodiment of FIGS. 24 and 25, the x-axes X1 and X1' of the first and further first implant elements 100 and 100' are aligned with each other.

According to an embodiment as shown in FIGS. 26 and 27, the first implant element 100 is formed in one piece with the further second implant element 200'. FIG. 26 shows a sectional view along the plane formed by the x- and z-axes of the implant elements and FIG. 27 is a top view of the first implant element 100 which is formed in one piece with the further second implant element 200'.

The first implant element 100 in FIGS. 26 and 27 comprises the first coupling portion 120 which comprises the accommodation recess 140 and the first insertion hole 160 which are formed as described in this application. The further second implant element 200' is formed like the second implant 200 as described in this application and extends along its corresponding further second element x-axis X2', along its corresponding further second element y-axis Y2' which extends transverse to the further second element x-axis X2', and along its corresponding further second element z-axis Z2' which extends transverse to the further second element x- and z-axes X2' and Y2'. The further second implant element 200' comprises the second coupling portion 220' which comprises the protrusion 240' and the second insertion hole 260', and the protrusion 240' and the second insertion hole 260' are formed like the protrusion 240 and the second insertion hole 260 described in this application, respectively. The protrusion 240' of the further second implant element 200' and the accommodation recess 140 of the first implant element 100 are oppositely arranged. In the embodiment of FIGS. 26 and 27, the x-axes X1 and X2' of the first and further second implant elements 100 and 200' are aligned with each other. It is to be understood that an embodiment, in which a second implant element 200 is formed in one piece with a further first implant element 100' is a mirrored version of the embodiment of FIGS. 26 and 27, and a detailed description thereof is therefore omitted.

In the embodiment of FIGS. 28*a*, 28*b* and 29, the second implant element 200 is formed in one piece with a further second implant element 200'. FIG. 28*a* shows a sectional view along the plane formed by the x- and z-axes of the implant elements, FIG. 28*b* shows a perspective view of this embodiment, and FIG. 29 is a top view of the second implant element 200 which is formed in one piece with the further second implant element 200'.

The second implant element 200 in FIGS. 28*a*, 28*b* and 29 comprises the second coupling portion 220 which comprises the accommodation recess 140 and the first insertion hole 160 which are formed as described in this application. The further second implant element 200' is formed like the second implant 200 as described in this application and which also extends along its corresponding further second element x-, y- and z-axes X2', Y2' and Z2'. The further second implant element 200' comprises the second coupling portion 220' which comprises the protrusion 240' and the second insertion hole 260' which are formed like the protrusion 240 and the second insertion hole 260 described in this application, respectively. The protrusion 240' of the further second implant element 100' and the accommodation recess 140 of the first implant element 100 are oppositely arranged, and the x-axes X2 and X2' of the first and further second implant elements 100 and 200' are aligned with each other.

Figure 30B:
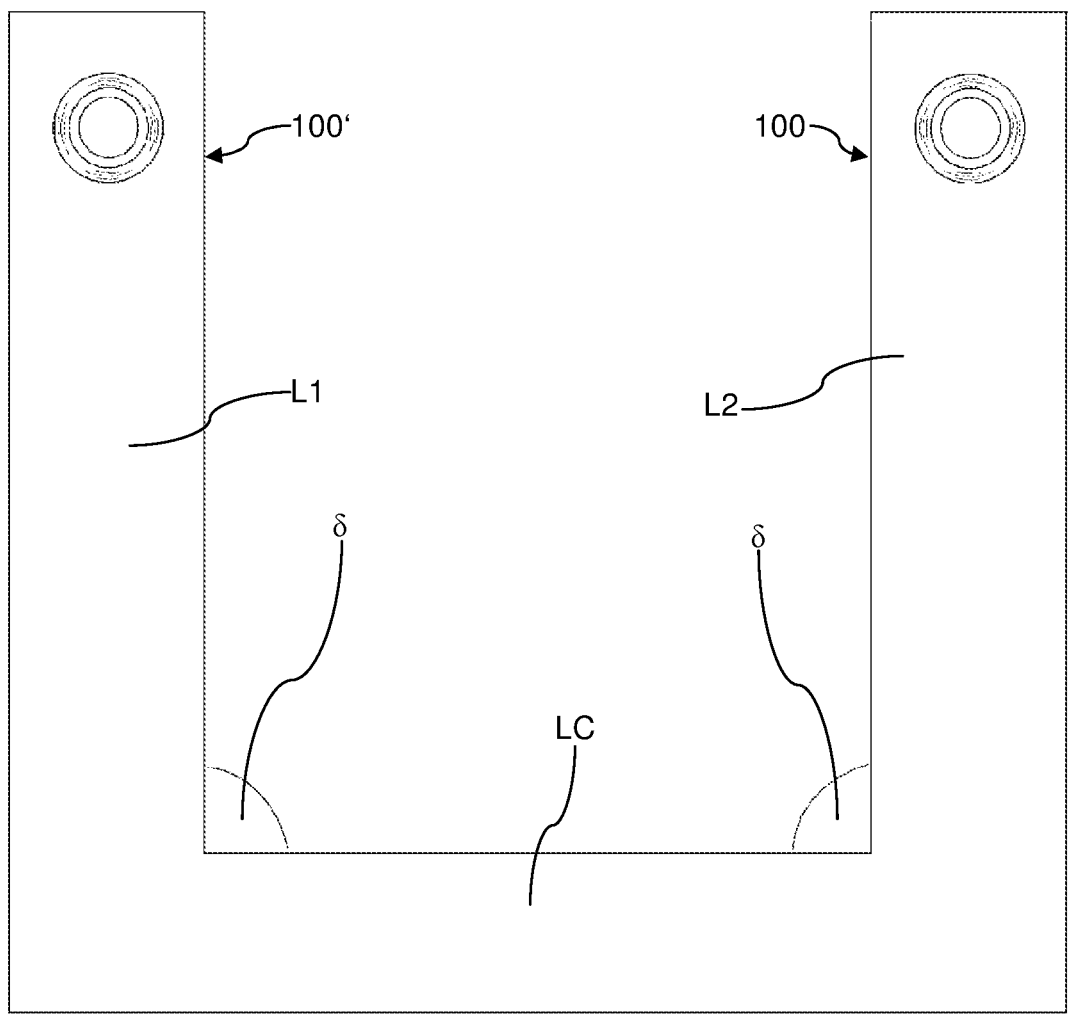
FIG. 30b is a top view of a first implant element which is formed in one piece in a U-shape with a further first implant element.
Figure 30C:
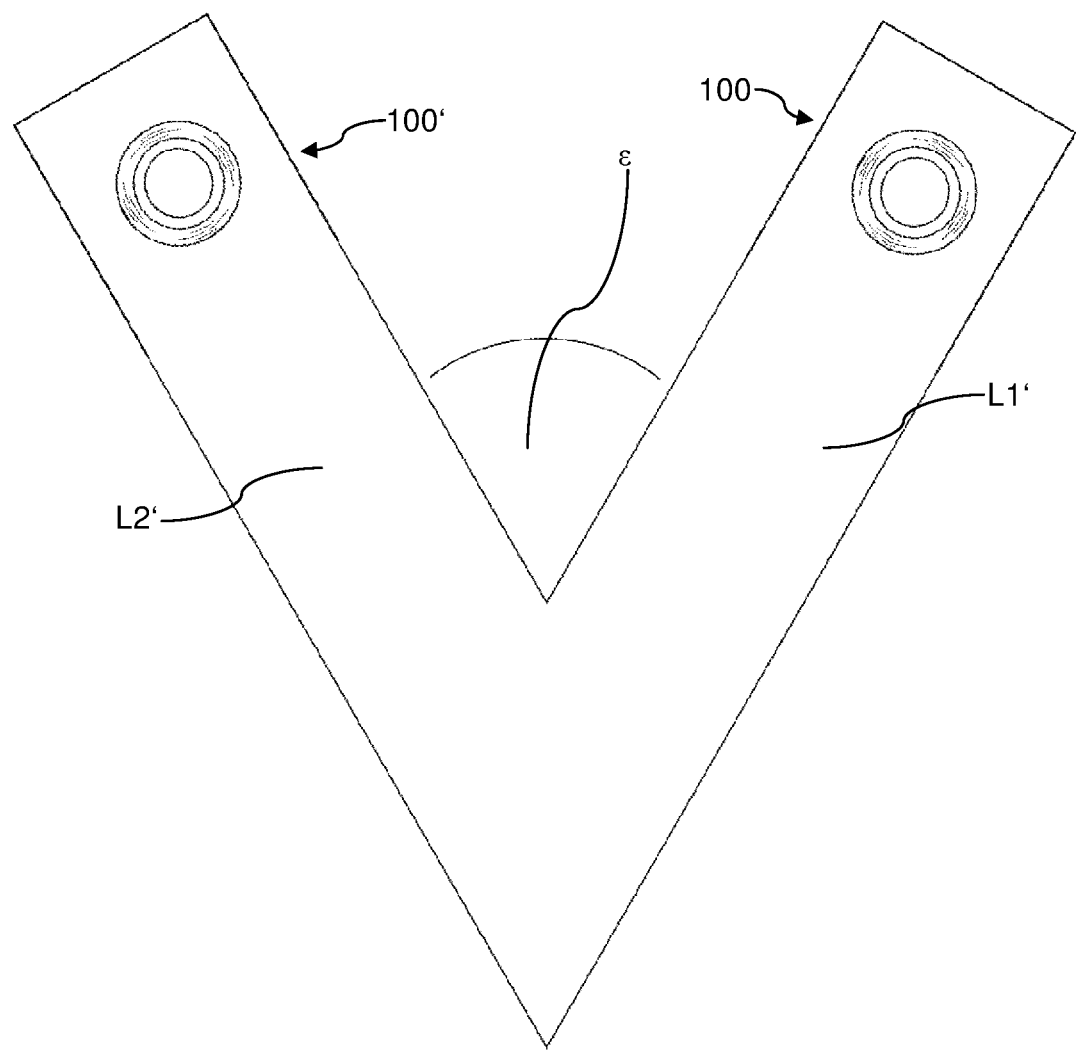
FIG. 30c is a top view of a first implant element which is formed in one piece in a V-shape with a further first implant element.

The monolithically formed implant elements shown in FIGS. 24 to 29 may also have angled configurations, in which one implant element (such as a first or further implant element 100 or 200) is formed in one piece with another implant element (such as a further first or further second implant element 100' or 200') in such a manner that an angle is formed therebetween. In the sectional view of FIG. 30a, a variation of the embodiment of FIGS. 24 and 25 is illustrated, in which the first and further first implant elements 100 and 100' are formed in one piece and are orientated at an angle γ relatively to each other. In other word, the first and further first implant elements 100 and 100' are formed in one piece with each other while being rotated relatively to each other in the plane formed by their x- and z-axes about the angle γ. Accordingly, the first and further first implant elements 100 and 100' are formed in one piece such that the first and further first implant elements 100 and 100' form the angle γ between each other (e.g. between the x-axes X1 and X1' and between the z-axes Z1 and Z1', respectively). Such an angled configuration as illustrated in FIG. 30a may also be applied to any one of the embodiments as shown in FIGS. 26 to 29. Further, other angled configurations with angles of different values and in different directions between the implant elements are also possible, and the present invention is not limited to the exemplary variation shown in FIG. 30a. For example, FIG. 30b illustrates a top view of another angled configuration of a monolithically formed implant element according to the present invention. As can be seen in FIG. 30b, a first implant element 100 is formed in one piece with a further first implant element 100', wherein the resulting monolithically formed implant element is formed in a substantially U-shape when viewed from above (e.g. in a cross section transverse to the first element z-axis Z1). The U-shape of the monolithically formed implant element in FIG. 30b comprises a first leg portion L1, a second leg portion L2 and a leg connection portion LC which connects the first leg and the second leg. An angle δ1 is formed between the first leg portion L1 and the leg connection portion LC, and an angle δ2 is formed between the second leg portion L2 and the leg connection portion LC. The angles δ1 and δ2 may form mirrored angles with the same value. Although the angles δ1 and δ2 exemplarily shown in FIG. 30b are right angles (i.e. angles of 90 degree), the angles δ1 and δ2 are not limited thereto and may have any angle which is appropriate for the desired application (e.g. 45 degree, 60 degree, 120 degree, 135 degree etc.). Further, FIG. 30c illustrates a top view of another angled configuration of a monolithically formed implant element according to the present invention. As can be seen in FIG. 30c, a first implant element 100 is formed in one piece with a with a further first implant element 100', wherein the resulting monolithically formed implant element comprises a V-shape when viewed from above (e.g. in a cross section transverse to the first element z-axis Z1). The V-shape of the monolithically formed implant element in FIG. 30c comprises a first leg portion L1' and a second leg portion L2' which are directly connected with each other and form an angle between each other. Although the angle ε exemplarily shown in FIG. 30c is approximately 60 degree, the angle ε is not limited thereto and may have any angle which is appropriate for the desired application (e.g. 45 degree, 30 degree, 75 degree, etc.). Accordingly, the monolithically formed implant elements of FIGS. 30b and 30c may be shaped according to the contour of the mandible and may be used to reconstruct the mandibular symphysis of the mandible. It is to be understood that such an angled configuration as illustrated in FIGS. 30b and 30c may also be applied to the embodiments as shown in FIGS. 26 to 29, e.g. the U-shaped or V-shaped monolithically formed implant element may be formed in one piece from the first implant element and the further second implant elements as in FIGS. 26 and 27 or may be formed in one piece from the second implant element and further second implant elements as in FIGS. 28a, 28b and 29.

Figure 31:
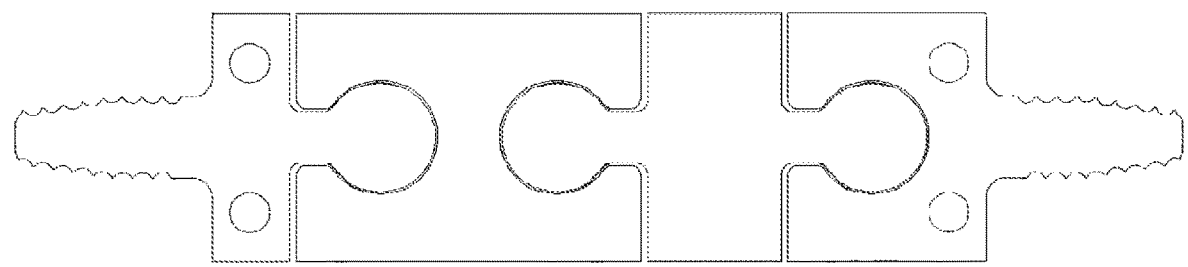
FIGS. 31 and 32 show mandible endoprosthesis implants according to still further embodiments of the invention, which are formed by coupling multiple different of the previously described implant elements.
Figure 32:
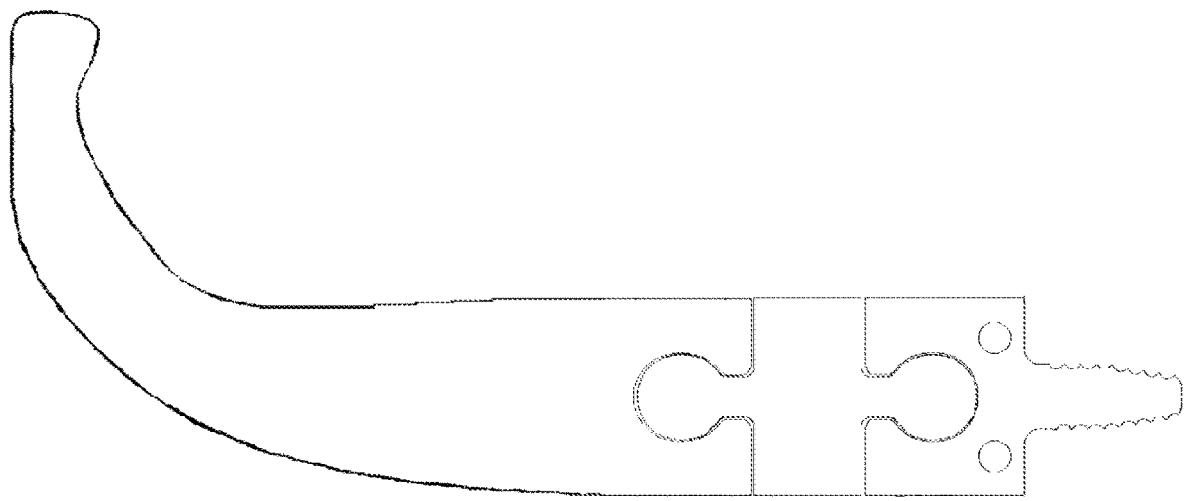

The monolithically formed implant elements shown in FIGS. 26 to 30c may have various lengths and angled configuration. Accordingly, the monolithically formed implant elements shown in FIGS. 26 to 30c may be connected with each other and/or with implant elements having a stem portion and/or with implant elements having a shaft portion by their corresponding coupling portions in order to form a mandible endoprosthesis implant according to the invention of a desired total length and suited for the specific application (e.g. depending on the part of the mandible 1 that needs to be reconstructed by the mandible endoprosthesis implant of the present invention). Due to this modular design, various configurations of the mandible endoprosthesis implant according to the present invention may be realized by coupling different types of first and second implant elements as described in this application with each other. For example, two implant elements, each provided with a respective stem portion, as shown in FIGS. 12 to 21 may be coupled with each other by one or a series of monolithically formed implant elements as shown in FIGS. 24 to 30c for reconstruction of the mandible body 3, wherein said implant elements may be respectively coupled to each other in the manner as described in this application to allow relative pivoting between adjacent implant elements. In another example, one implant element provided with a stem portion as shown in FIGS. 12 to 21 may be directly coupled with an implant element provided with a curved shaft portion as shown in FIGS. 22 to 23 or may be indirectly coupled with an implant element provided with a curved shaft portion as shown in FIGS. 22 to 23 by one or a series of monolithically formed implant elements as shown in FIGS. 24 to 30c for reconstruction of the condyle-ramus region 7 and, if necessary, also of a part of the mandible body 3. Non-limiting further examples of mandible endoprosthesis implants according to the invention, which are formed by coupling multiple different implant elements of the described implant elements as described in this application, are illustrated in FIGS. 31 and 32.

FIG. 33 is a cross-sectional view of a fastener 300 of the mandible endoprosthesis implant according to the present invention. Here, the fastener 300 is a screw which comprises the countersunk head 303 and further comprises the threaded shaft 306. The threaded shaft 306 comprises the elongated shaft portion 307 which extends from the countersunk head 303 and has the outer diameter D4. Further, the threaded shaft 306 comprises the outer thread 308 for engagement with the inner thread 163 of the first insertion hole 160. In the embodiment of FIG. 33, the fastener 300 comprises a shoulder 309 which is formed between the shaft portion 307 and the outer thread 308 of the fastener (e.g. since the outer thread 308 has a smaller maximum outer diameter D5 than the outer diameter D4 of the shaft portion 307). The shoulder 309 may rest against the inner wall 123 of the first implant element 100. However, the fastener 300 may be formed without shoulder 309 (e.g. by providing the outer thread 308 with a maximum outer diameter D5 that is at least substantially equal to the outer diameter D4 of the of the shaft portion 307). Any kind of complementary inner and outer threads may be used for the inner thread 163 of the first insertion hole 160 and the outer thread 308 of the fastener 300, respectively, in order to fixedly attach the fastener 300 to the first coupling portion 120.

When the fastener 300 is to be inserted into a first insertion hole 160 which comprises, alternatively or additionally to the inner thread 163 in the second passage 172, an inner thread within its first passage 169, said inner thread within the first passage 169 being disposed below and adjacent to the countersunk hole portion 166 of the first passage 169, the fastener 300 may, alternatively or additionally, have an outer thread below the countersunk head 303 of the fastener 300.

It is to be understood that the fastener 300 of the present invention is not limited to a screw and other types of fasteners 300 may also be used. For example, the fastener 300 may be a pin that is press-fitted into a correspondingly shaped first insertion hole 160 of the first implant element 100.

In the following, embodiments of the mandible endoprosthesis implant system according to the present invention will described with reference to FIGS. 34 to 37.

Figure 34:
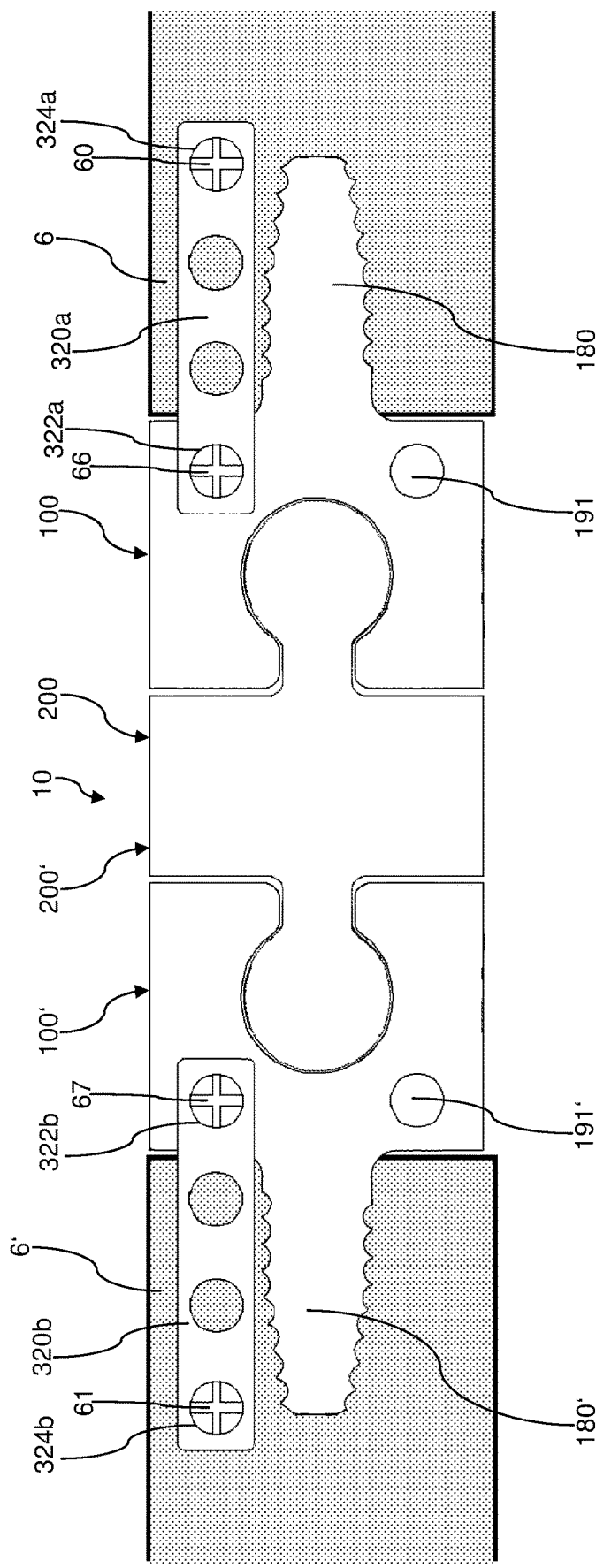
FIG. 34 is a side view illustrating an assembled state of a mandible endoprosthesis implant system according to a first embodiment of the present invention.
Figure 35:
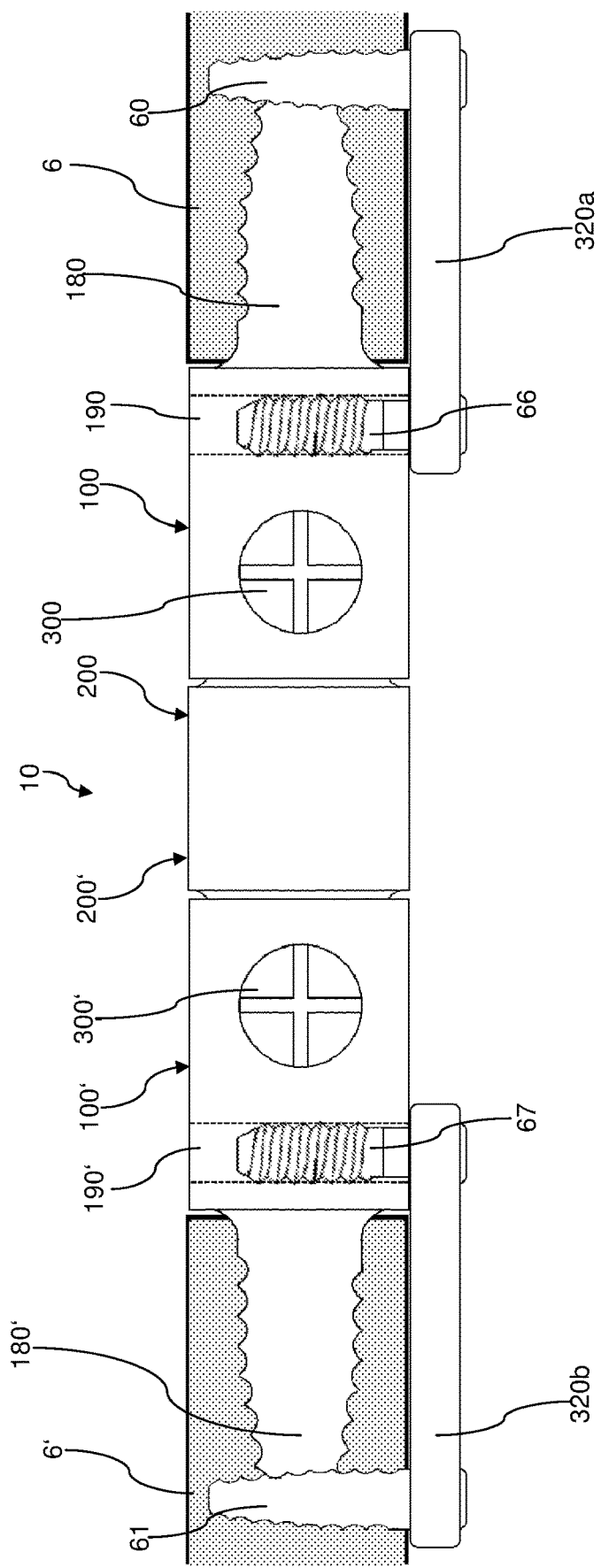
FIG. 35 is a top view of the mandible endoprosthesis implant system according to the first embodiment.

FIGS. 34 and 35 illustrate an assembled state of a mandible endoprosthesis implant system according to a first embodiment. The mandible endoprosthesis implant system according to the first embodiment comprises the mandible endoprosthesis implant 10 as shown in FIGS. 2 and 3, in which the first implant element 100 has upper and lower first plate attachment holes 190 and 191 and in which the further first implant element 100' has upper and lower first plate attachment holes 190' and 191'.

Further, the system comprises a first elongated implant fixation plate 320a which includes a plurality of screw insertion through-holes and a second elongated implant fixation plate 320b which also includes a plurality of screw insertion through-holes. The first elongated implant fixation plate 320a has a length which is at maximum the length of the first implant element 100 along the first element x-axis X1, and the second elongated implant fixation plate 320b has a length which is at maximum the length of the further first implant element 100' along the x-axis X1' of the further first element 100. The system also comprises a first and a second bone screw 60 and 61, and comprises a first and a second plate attachment screw 66 and 67.

The first implant fixation plate 320a is attached to the first implant element 100 by the first plate attachment screw 66 passing through the first screw insertion through-hole 322a among the plurality of screw insertion through-holes of the first implant fixation plate 320a and engaging the first upper plate attachment hole 190 of the first implant element 100. Further, the first implant fixation plate 320a is attached to the first bone portion 6 of the patient's mandible 1 by the first bone screw 60 passing through the second screw insertion through-hole 324a among the plurality of screw insertion through-holes of the first implant fixation plate 320a and engaging the corresponding bone portion 6 of the patient's mandible 1.

Similarly, the second implant fixation plate 320b is attached to the further first implant element 100' by the second plate attachment screw 67 passing the first screw insertion through-hole 322b among the plurality of screw insertion through-holes of the second implant fixation plate 320b and engaging the upper first plate attachment hole 190' of the further first implant element 100'. Also, the second implant fixation plate 320b is attached to the corresponding bone portion 6' of the patient's mandible 1 by the second bone screw 61 passing through the second screw insertion through-hole 324b among the plurality of screw insertion through-holes of the second implant fixation plate 320b and engaging the corresponding bone portion 6' of the patient's mandible 1.

It is to be understood that the two implant fixation plates 320a and 320b may be connected to the lower first plate attachment holes 191 and 191' of the first and further first implant elements 100 and 100' instead of the upper first plate attachment holes 190 and 190'.

The first and second implant fixation plates 320a and 320b may serve to additionally hold the first and further first stem portions 180 and 180' in the corresponding bone portions 6 and 6', thereby further improving the distribution of loads in order to minimize loads and stress concentration at the first and further first stem portions 180 and 180'. Accordingly, the risk of loosening of the first and further first stem portions 180 and 180' from the corresponding bone portions may be further reduced and the osseointegration of the first stem portions 180 and 180' may be allowed to occur.

Figure 36:
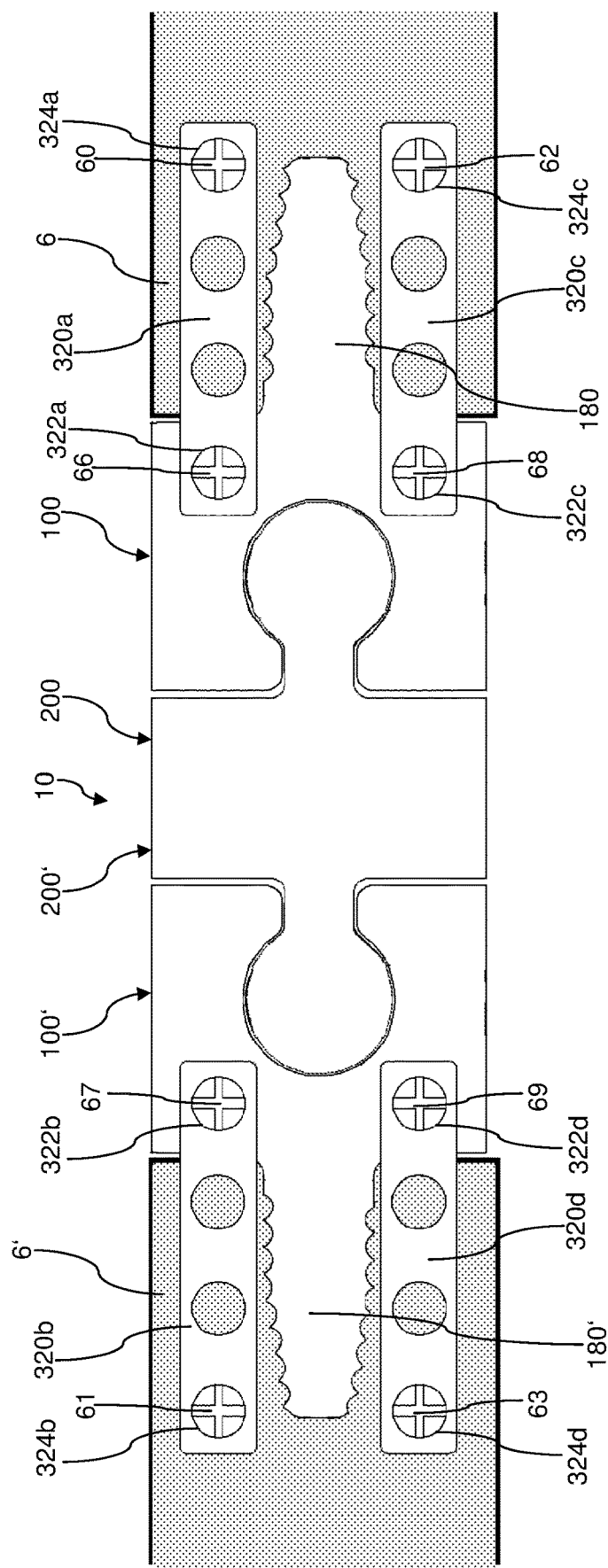
FIG. 36 is a side view illustrating an assembled state of a mandible endoprosthesis implant system according to a second embodiment of the present invention.

FIG. 36 illustrates an assembled state of a mandible endoprosthesis implant system according to a second embodiment. The mandible endoprosthesis implant system according to the second embodiment differs from the first embodiment of the mandible endoprosthesis implant system in that the mandible endoprosthesis implant system according to the second embodiment additionally includes a third implant fixation plate 320c and a fourth implant fixation plate 320d, each having a plurality of screw insertion through-holes, the third and fourth plate attachment screws 68 and 69 and the third and fourth bone screws 62 and 63. As shown in FIG. 36, the third and fourth implant fixation plates 320c and 320d extend in a direction opposite to the first and second implant fixation plates 320a and 320b

The third implant fixation plates 320c is attached to the lower first plate attachment hole 191 of the first implant element 100 by the third plate attachment screw 68 passing through the first screw insertion through-hole 322c of the third implant fixation plate 320c and engaging the first lower plate attachment hole 191 of the first implant element 100, and is attached to the first bone portion 6 of the patient's mandible 1 by the third bone screw 62 passing through the second screw insertion through-hole 324c of the third implant fixation plate 320c and engaging the corresponding bone portion 6 of the patient's mandible 1. The fourth implant fixation plate 320d is attached to the further first implant element 100' by the fourth plate attachment screw 69 passing the first screw insertion through-hole 322d of the fourth implant fixation plate 320d and engaging the lower first plate attachment hole 191' of the further first implant element 100' and is attached to the corresponding bone portion 6' of the patient's mandible 1 by the fourth bone screw 63 passing through the second screw insertion through-hole 324d of the fourth implant fixation plate 320d and engaging the corresponding bone portion 6' of the patient's mandible 1.

Figure 37:
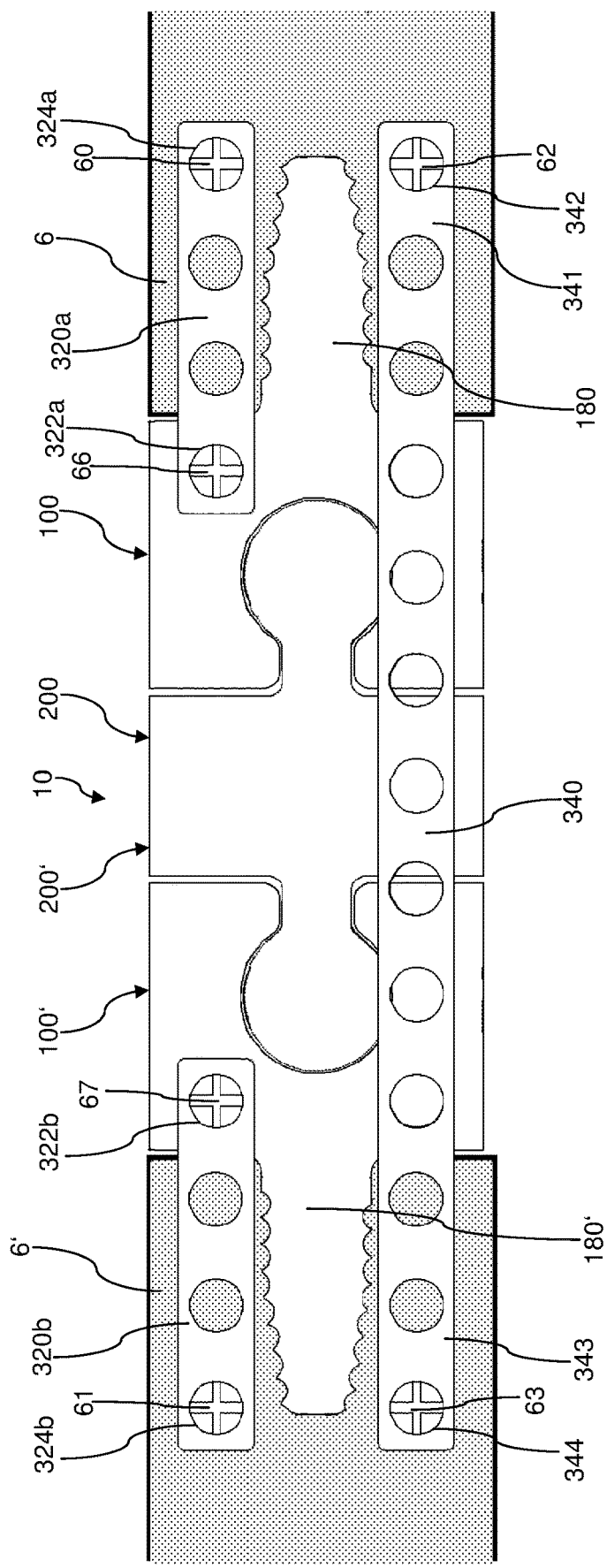
FIG. 37 is a side view illustrating an assembled state of a mandible endoprosthesis implant system according to a third embodiment of the present invention.

FIG. 37 illustrates an assembled state of a mandible endoprosthesis implant system according to a third embodiment. The third embodiment differs from the first embodiment of the mandible endoprosthesis implant system in that it additionally includes one elongated bone fixation plate 340 which has a plurality of through-holes and which is longer than each of the first and second implant fixation plates 320a and 320b. The bone fixation plate 340 has first and second longitudinal plate ends 341 and 343, wherein each of the first and second longitudinal plate ends 341 and 343 is provided with a respective bone fixation through-hole 342 and 344 among the plurality of through-holes of the bone fixation plate 340. The third and fourth bone screws 62 and 63 are passed through the bone fixation through-holes 342 and 344, respectively, in order to fix the bone fixation plate 340 to the bone portions 6, 6', respectively. As can be seen in FIG. 37, the bone fixation plate 340 is disposed below the first and second implant fixation plates 320a and 320b (e.g. at the level of the lower first plate attachment holes 191 and 191'). The bone fixation plate 340 is connected to the bone portions 6 and 6' and serves to bridge the resected portion 2 of the mandible 1. In FIG. 37, the bone fixation plate 340 is connected to the bone portions 6 and 6' without being connected to the mandible endoprosthesis implant 10 in order to further minimize relative movement between the bone portions 6 and 6' and to thus further reduce movement at the interface between the first stem portion 180 and the bone portion 6 and at the interface between the further first stem portion 180' and the bone portion 6'. Optionally, the through-holes of the bone fixation plate 340 may be sized for allowing the passage of the third and fourth plate attachment screws 68 and 69 therethrough in order to attach the bone fixation plate 340 also to the lower first plate attachment holes 191 and 191' by the third and fourth plate attachment screws 68 and 69, respectively. It is to be understood that the positions of the bone fixation plate 340 and the pair of fixation plates 320a and 320b may also be exchanged with each other so that the bone fixation plate 340 is arranged above the first and second fixation plates 320a and 320b (which would in such a case be attached to the lower first plate attachment holes 191 and 191', respectively). It is to be further understood that the bone fixation plate 340 may also be used alone (i.e. without the pair of fixation plates 320a and 320b). In addition, the system may be provided with a further bone fixation plate instead of the pair of fixation plates 320a and 320b, wherein said further bone fixation plate connected to the bone portions 6 and 6' and serves to bridge the resected portion 2 of the mandible 1 in a similar manner as the bone fixation plate 340 which is shown in FIG. 37 and has been described above.

In the first to third embodiments of the mandible endoprosthesis implant system, the first to fourth implant fixation plates 320a to 320d as well as the bone fixation plate 340 may be plastically deformed, e.g. prior to or during surgery, such that they correspond to the outer contour of the mandible's bone portions 6 and 6', respectively. As shown in the second embodiment, the first and third implant fixation plates 320a and 320c and the second and fourth implant fixation plates 320b and 320d may be disposed in parallel to each other, respectively. It is, however, to be understood that each of the first to fourth implant fixation plates 320a to 320d as well as the bone fixation plate 340 may be orientated relatively to each other at various angles as being found appropriate by the surgeon. Although, the first screw insertion through-holes 322a to 322d and 324a to 324d of the first to fourth implant fixation plates 320a to 320d as well as the bone fixation through-holes 343 and 344 of the bone fixation plate 340 are shown as the longitudinally outer most screw through-holes in FIGS. 34 to 37, it is to be understood that any appropriate through-hole among the plurality of through-holes of the first to fourth implant fixation plates 320a to 320d and of the bone fixation plate 340 may be configured and selected for passing the respective plate attachment screw or bone screw therethrough. The selection of the orientation of the plates relative to each other as well as the exact positioning of the bone screws in the bone portion of the mandible may depend on the potential interference with tooth roots and/or the structural integrity of the bone portion. The bone screws may be engaged to bone by a mono-cortical bone engagement or by a bi-cortical bone engagement. The selection of mono or bi-cortical bone engagement for a specific bone screw may depend on the desired load bearing capabilities of corresponding plate (e.g. any one among the implant fixation plates 320a to 320d and the bone fixation plate 340) to be attached by said specific bone screw.

Although FIGS. 35 to 37 illustrate the assembled state of a mandible endoprosthesis implant system according to the invention which includes a mandible endoprosthesis implant 10 according to the first embodiment shown in FIGS. 1 to 9, it is apparent that the same principles also apply to mandible endoprosthesis implant system which include mandible endoprosthesis implant having configurations that are different from the mandible endoprosthesis implant 10 according to the first embodiment, such as, but not limited to, those shown in FIGS. 10, 11 and 31. It is to be understood that the various plates may be attached to the implant elements and/or to the bone portions by more screws than illustrated in FIGS. 35 to 37 and that the present invention is not limited to the number of screws as in illustrated in FIGS. 35 to 37.

The various components of the mandible endoprosthesis implant system (e.g. the implant elements and fastener of the mandible endoprosthesis implant and the various plates and screws) may be manufactured from biologically acceptable materials suitable for medical applications, including metal materials, ceramic materials, polymer materials and composites thereof, depending on the particular application and/or preference of a medical practitioner. Non-limiting examples for such materials may include metal materials such as stainless steel and alloys thereof, titanium and alloys thereof, cobalt-chromium or others, ceramic materials, such as zirconia or others, polymer composites, such as polycaprolactone-tricalcium phosphate or others, and other composite materials or the aforementioned materials used in combination.

Figure 38A:
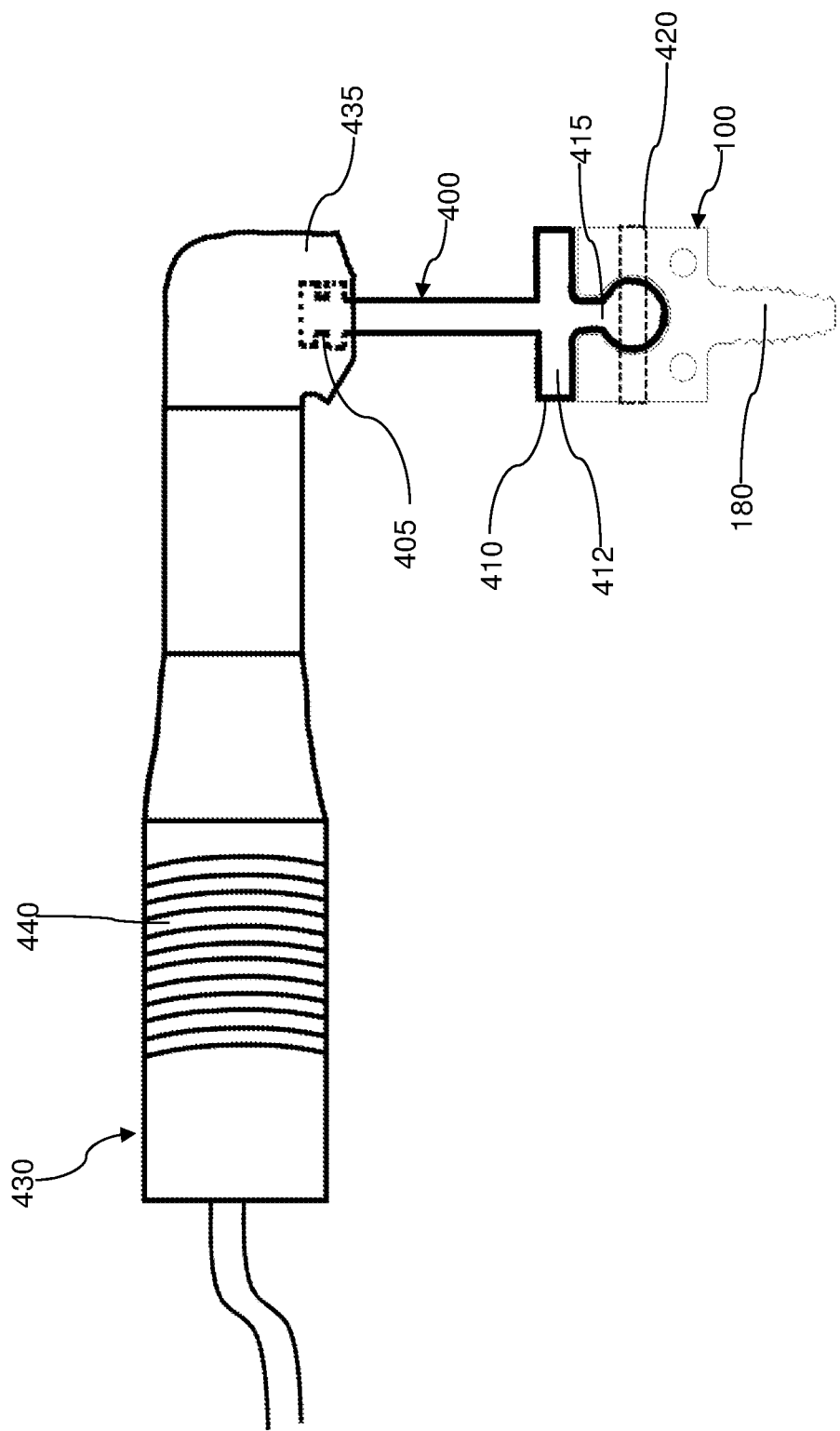
FIG. 38a is a schematic illustration of a hand tool and a first embodiment of a first implant element mount according to the present invention, in which the first implant element mount connects a first implant element of the present invention to the hand tool.

Further, FIGS. 38a to 38e schematically illustrate a first exemplary embodiment of the first implant element mount 400 according to the present invention and the use thereof. As can be seen in FIG. 38a, the first end 405 of the first implant element mount 400 is attached to a mount attachment portion 435 of a hand tool 430. The hand tool 430 further comprises a grip portion 440 which can be gripped by the surgeon. The hand tool 430 may for example be a dental hand tool and may be configured to rotate the first implant element mount 400 when the first implant element mount 400 is attached to the mount attachment portion 435 of the hand tool 430. As shown in FIGS. 38a to 38e, the second end 410 of the first implant element mount 400 comprises a block portion 412 from which a mount protrusion 415 extends. The mount protrusion 415 is engageable with the accommodation recess 140 of a first implant element 100, said first implant element 100 comprising a first stem portion 180. The block portion 412 and the mount portion 415 of the first implant element mount 400 may be formed in a shape such that, when the mount protrusion 415 is engaged with the accommodation recess 140, relative pivoting between the first implant element mount 400 and the first implant element 100 is at least substantially prevented. In the first embodiment, the first locking device is an elongated first locking rod 420, and the mount protrusion 415 comprises a rod insertion hole 417 (as shown in FIGS. 38b to 38e). When the mount protrusion 415 is engaged with the accommodation recess 140 of the first implant element 100, the first insertion hole 160 of the first implant element 100 and the rod insertion hole 417 are at least substantially aligned with each other and a coupled condition between the first implant element mount 400 and the first implant element 100 is established. FIG. 38a schematically illustrates a state in which the first locking rod 420 is engaged into both the first insertion hole 160 of the first implant element 100 and the rod insertion hole 417. The first locking rod 420 may for example comprise an outer thread that can cooperate with the inner thread 163 (see e.g. FIG. 13) formed within the first insertion hole 160. For example, the first locking rod 420 may be in the form of a fastener 300 as described in this application (such as the screw with the countersunk head as shown in FIG. 33). When inserted into both the first insertion hole 160 of the first implant element 100 and the rod insertion hole 417, the first locking rod 420 maintains the coupled condition of the first implant element mount 400 and the first implant element 100 and locks the first implant element 100 and the first implant element mount 400 together. For example, the first locking rod 420 locks the first implant element 100 and the first implant element mount 400 together in a manner such that the first implant element 100 and the first implant element mount 400 are rotated together. By attaching the first implant element mount 400 to a hand tool 430, which can rotate the first implant element mount, and by locking the first implant element 100 to the first implant element mount 400 in the above described manner, it is possible to facilitate the insertion of the first stem portion 180 into the respective bone portion (e.g. the cancellous region thereof) of the mandible and reduce pressure on the surrounding bone tissues during the procedure. After the insertion of the first stem portion 180 into the respective bone portion, the first locking rod 420 can be easily removed from both the first insertion hole 160 of the first implant element 100 and the rod insertion hole of the first implant element mount 400, and the first implant element mount 400 can be removed from the first implant element 100. It is to be understood that the first locking rod 420 may have a diameter that is smaller than or at least matches the diameter of the first insertion hole 160 of the first implant element 100 and that is smaller than or at least matches the diameter of the rod insertion hole 417 of the first implant element mount 400 such that it can be accordingly inserted into the first insertion hole 160 of the first implant element 100 and the rod insertion hole 417 of the first implant element mount 400.

Figure 38F:
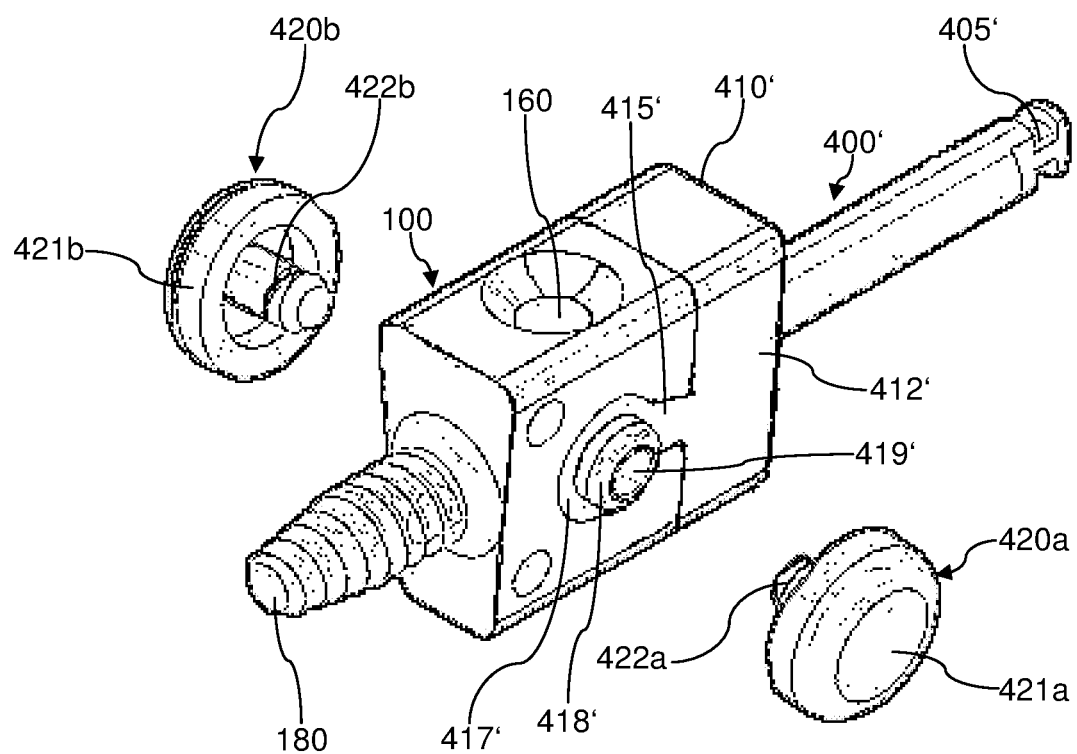
FIG. 38f is a partially exploded perspective view illustrating a second embodiment of a first implant element mount and a first implant element of the present invention.
Figure 38G:
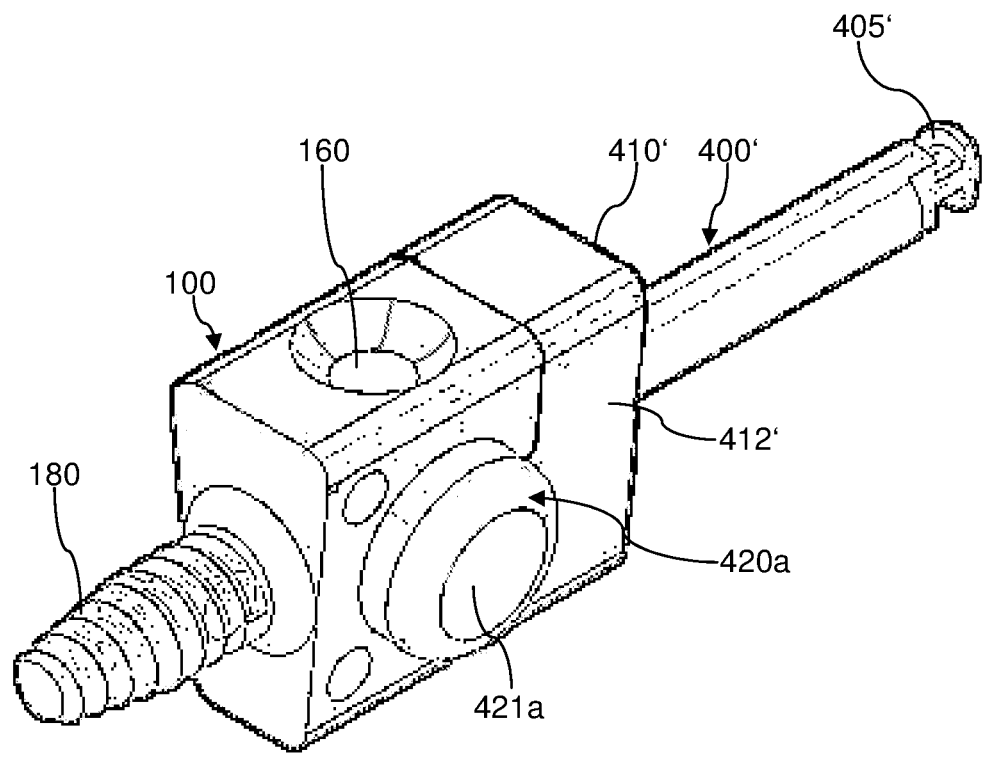
FIG. 38g is perspective view illustrating an assembled state of the second embodiment of the first implant element mount and the first implant element of the present invention.

A second exemplary embodiment of the first implant element mount 400' according to the present invention is illustrated in FIGS. 38f and 38g. The first implant element mount 400' according to the second exemplary embodiment comprises a first end 405' and a second end 410'. The first end 405' is attachable to the mount attachment portion 435 of the hand tool 430. The second end 410' comprises a block portion 412' from which a mount protrusion 415' extends. The mount protrusion 415' is engaged with the accommodation recess 140 of a first implant element 100, said first implant element 100 comprising a first stem portion 180. The block portion 412' and the mount portion 415' of the first implant element mount 400' may be formed in a shape such that, when the mount protrusion 415' is engaged with the accommodation recess 140, relative pivoting between the first implant element mount 400' and the first implant element 100 is at least substantially prevented. In the second embodiment of the first implant element mount, the first locking device includes a first locking cap 420a and a second locking cap 420b. The first locking cap 420a comprises a first cap base 421a and an elongated first threaded portion 422a extending from the first cap base 421a. Similarly, the second locking cap 420b comprises a second cap base 421b and an elongated second threaded portion 422b extending from the second cap base 421b. Further, the mount protrusion 415' of the first implant element mount 400' comprises a lateral first cap attachment part 418' disposed at a first end face 417' of the mount protrusion 415' and comprises a second lateral second cap attachment part (not shown) disposed at a second end face (not shown) of the mount protrusion 415', the second end face being disposed opposite to the first end face 417'. The first cap attachment part 418' has a first threaded hole 419' and the second cap attachment part comprise a second threaded hole (not shown). The first locking cap 420a can be coupled to the first cap attachment part 417' by threaded engagement between the first threaded portion 422a and the first threaded hole 419', and the second locking cap 420b can be coupled to the second cap attachment part by threaded engagement between the second threaded portion 422b and the second threaded hole. By coupling the first locking cap 420a to the first cap attachment part 417' and coupling the second locking cap 420b to the second cap attachment part, the first implant element 100 can be engaged by the first and second locking caps 420a and 420b, respectively, such that the first implant element 100 and the first implant element mount 400' are locked together. For example, the first and second locking caps 420a and 420b lock the first implant element 100 and the first implant element mount 400' together in a manner such that the first implant element 100 and the first implant element mount 400' are rotated together. It may be contemplated that the first locking cap 420a and the second locking cap 420b clamp the first implant element 100 between each other. By attaching the first implant element mount 400' according to the second embodiment to a hand tool 430, which can rotate the first implant element mount 400', and by locking the first implant element 100 to the first implant element mount 400 by use of the first and second locking caps 420a and 420b, it is possible to facilitate the insertion of the first stem portion 180 into the respective bone portion (e.g. the cancellous region thereof) of the mandible 1 and reduce pressure on the surrounding bone tissues during the procedure. After the insertion of the first stem portion 180 into the respective bone portion, the first and second locking caps 420a and 420b can be easily removed from the first and second cap attachment parts, respectively, and the first implant element mount 400' can accordingly be removed from the first implant element 100.

Figure 39A:
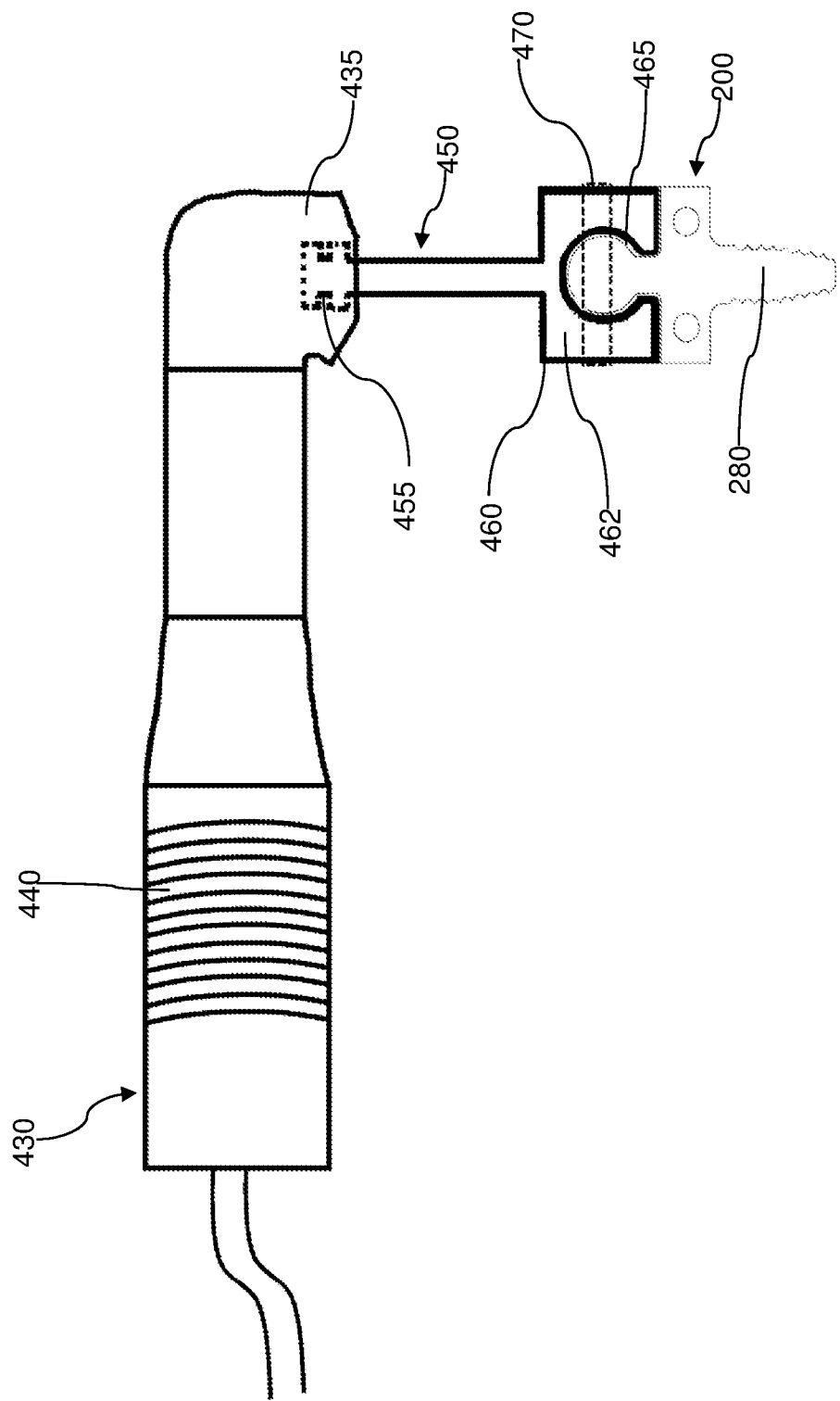
FIG. 39a is a schematic illustration of a hand tool and an embodiment of a second implant element mount according to the present invention, in which the second implant element mount connects a second implant element of the present invention to the hand tool.
Figure 39D:
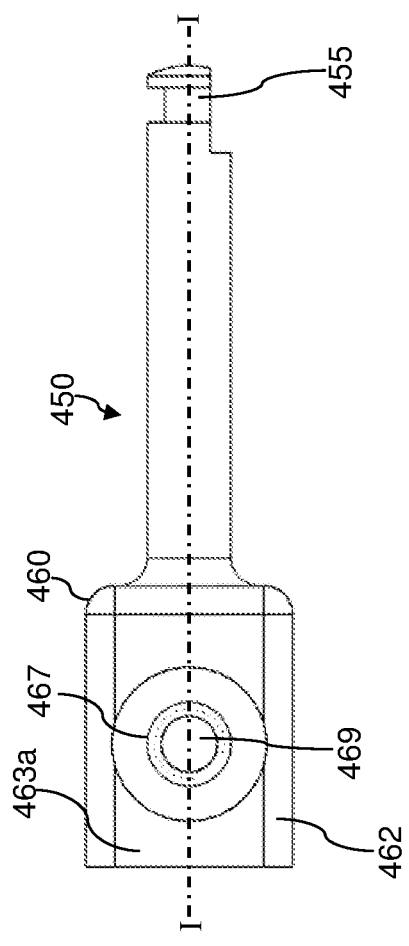
FIG. 39d is a top view of the second implant element mount according of FIG. 39b.
Figure 39E:
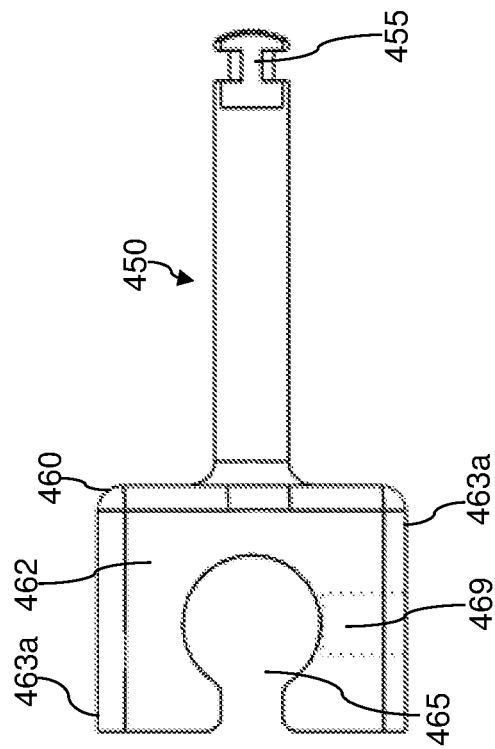
FIG. 39e is a cross-sectional view along line I-I of FIG. 39d.
Figure 39B:
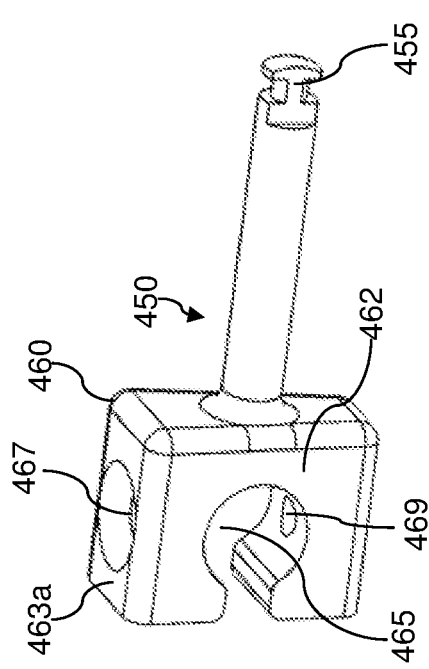
FIG. 39b is a perspective view of the second implant element mount according to an embodiment of the present invention.
Figure 39C:
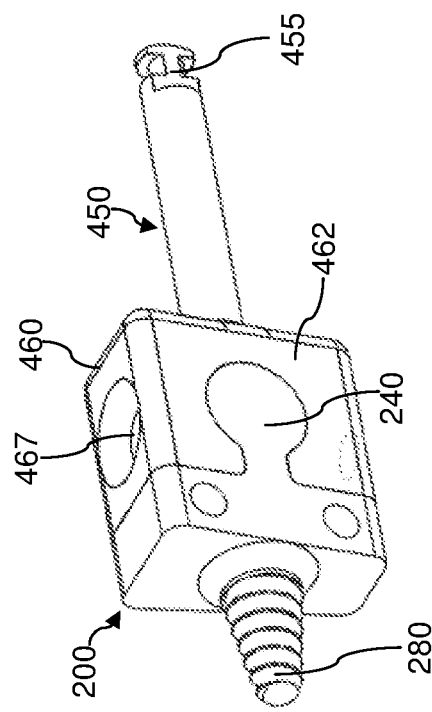
FIG. 39c is a perspective view illustrating a coupled condition of the second implant element mount according and the second implant element of the present invention.

Further, FIGS. 39a to 39e illustrate an exemplary embodiment of the second implant element mount 450 according to the present invention and the use thereof. As can be seen in FIGS. 39a to 39e, the first end 455 of the second implant element mount 400 is attached to a mount attachment portion 435 of a hand tool 430. The hand tool 430 further comprises a grip portion 440 and may for example be a dental hand tool as described above which can rotate the second implant element mount 400 when the second implant element mount 400 is attached to the mount attachment portion 435 of a hand tool 430. As shown in FIGS. 39a to 39e, the second end 460 of the second implant element mount 450 comprises a block portion 462 and a mount recess 465 which is formed in the block portion 462. The mount recess 465 is engageable engaged with the protrusion 240 of a second implant element 200, said second implant element 200 comprising a first stem portion 280. The second implant element mount 450 further has a first rod insertion hole 467 and a second rod insertion hole 469 which extend through the block portion 462 and connect the upper and lower block surfaces 463a and 463b with the mount recess 465, respectively. The first and second rod insertion holes 467, 469 may be similar to the first passage 169 and the second passage 172 of the first implant element 100. When the mount recess 465 is appropriately engaged with the protrusion 240 of the second implant element 200, the second insertion hole 260 of the second implant element 200 and the first and a second rod insertion holes 467, 469 are at least substantially aligned with each other. Thereby, a coupled condition between the second implant element mount 450 and the second implant element 200 is established. As schematically illustrated in FIG. 39a, the second locking device may be an elongated second locking rod 470 (illustrated by a dashed line in FIG. 39a). The second locking rod 470 may for example comprise an outer thread that can cooperate with an inner thread formed within the first and/or second rod insertion hole 467, 469 of the second implant element mount 450. For example, the locking rod 420 may be in the form of a fastener 300 as described in this application (such as the screw with the countersunk head as shown in FIG. 33). It is further schematically illustrated in FIG. 39 that the second locking rod 470 is engaged into both the second insertion hole 260 of the second implant element 200 and the first and a second rod insertion holes 467, 469 of the second implant element mount 450. Thus, the second locking rod 470 maintains the coupled condition of the second implant element mount 450 and the second implant element 200 and locks the second implant element mount 450 and the second implant element 200 together. Similar to the first embodiment of the first implant element mount 400, the second implant element mount 450 can be attached to a hand tool 430, which can rotate the second implant element mount 450, and the second implant element mount 450 can simultaneously be coupled to the second implant element 200. Thus, it is also possible to facilitate the insertion of the second stem portion 280 into the respective bone portion (e.g. the cancellous region thereof) of the mandible and also reduce pressure on the surrounding bone tissues during the procedure. After the insertion of the second stem portion 280 into the respective bone portion, the second locking rod 470 can also be easily removed from the second insertion hole 260 of the second implant element 200 and the first and second rod insertion holes 467, 469 of the second implant element mount 450. Then, the second implant element mount 450 can be removed from the second implant element 200. It is to be understood that the second locking rod 470 has a diameter that is smaller than or at least matches the diameter of the of the second insertion hole 260 of the second implant element 200 and that is smaller than or at least matches the diameter of the first and second rod insertion holes 467, 469 of the second implant element mount 450 such that it can be accordingly inserted into the second insertion hole 160 of the first implant element 100 and the first and second rod insertion holes 467, 469 of the second implant element mount 450.

Figure 40A:
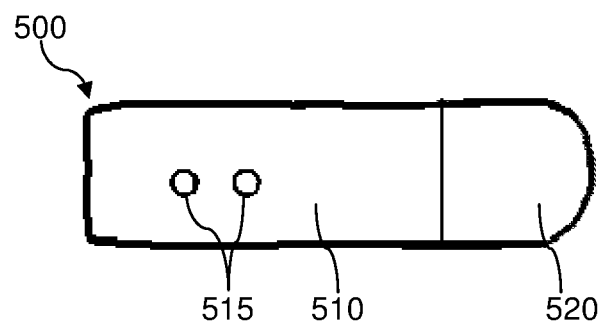
FIG. 40a is a side view of a first surgical guide according to an embodiment the present invention.
Figure 40B:
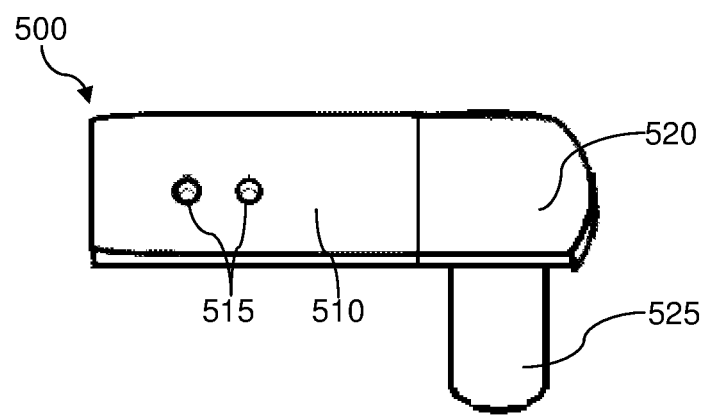
Figure 40C:
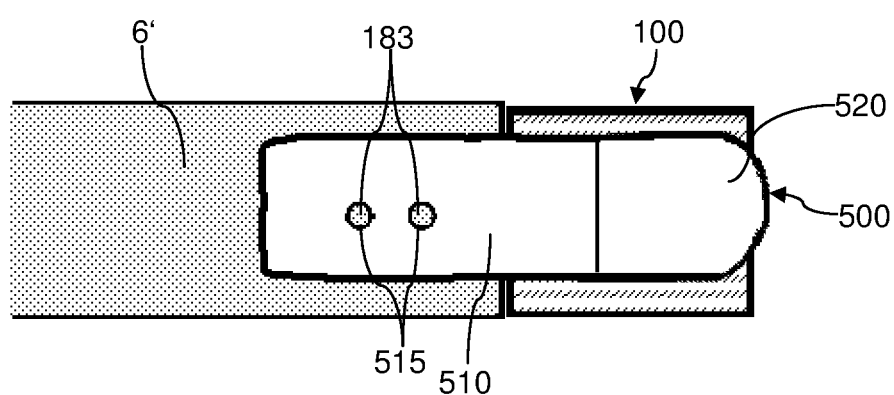
FIG. 40c is a side view illustrating a state in which the first surgical guide of FIGS. 40a and 40b is attached to a first implant element, which is fixed to a bone portion of a patient's mandible.
Figure 40D:
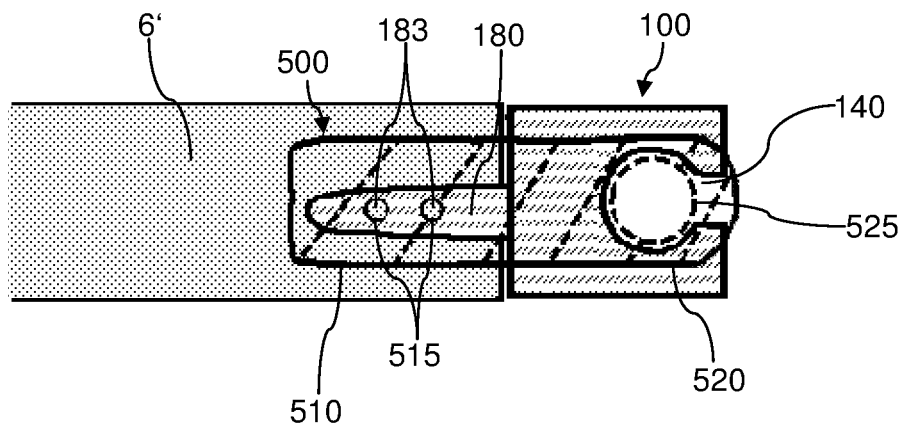
FIG. 40d is a side view illustrating the state of FIG. 40c by showing the first surgical guide in a transparent manner.
Figure 41A:
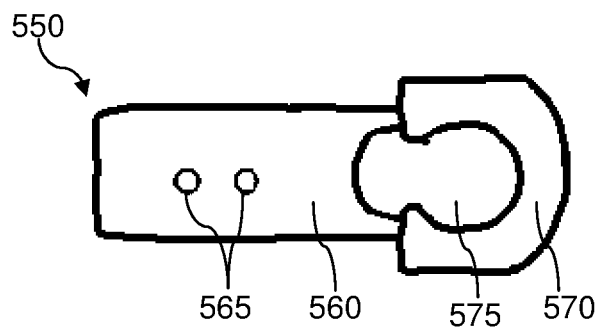
FIG. 41a is a side view of a second surgical guide according to an embodiment the present invention.
Figure 41B:
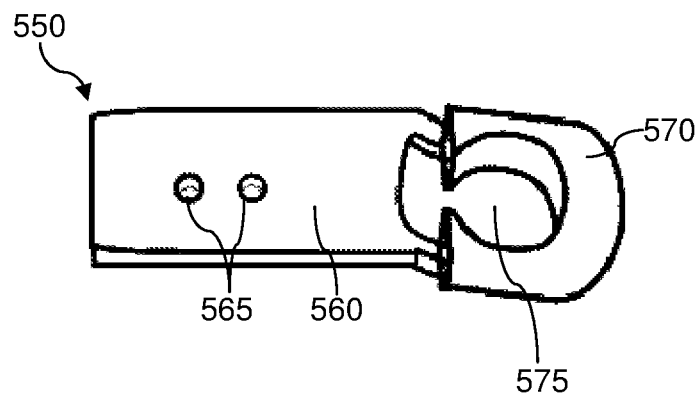
Figure 41C:
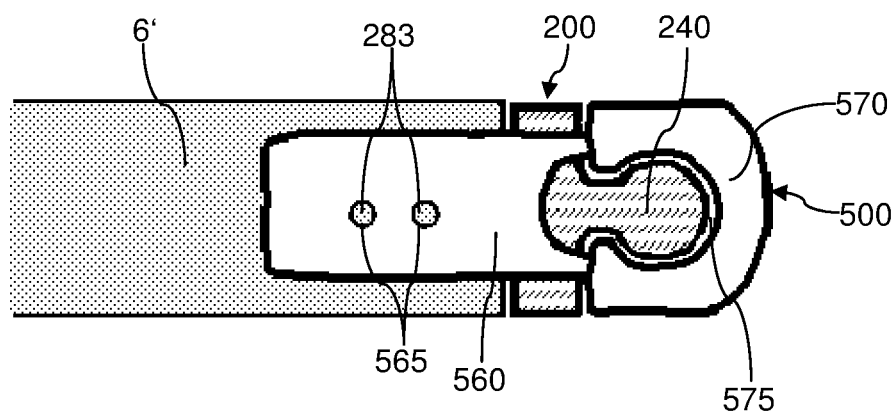
FIG. 41c is a side view illustrating a state in which the second surgical guide of FIGS. 40a and 40b is attached to a second implant element, which is fixed to a bone portion of a patient's mandible.
Figure 41D:
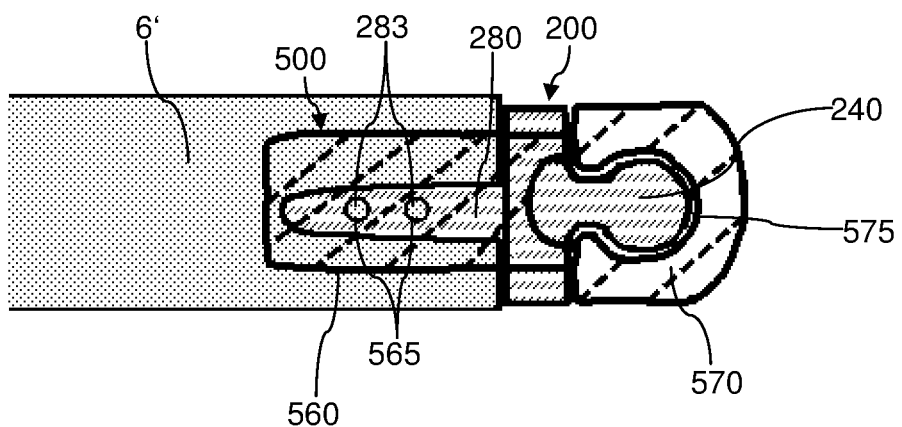
FIG. 41d is a side view illustrating the state of FIG. 41c by showing the second surgical guide in a transparent manner.

An exemplary embodiment of the first surgical guide 500 according to the present invention is schematically illustrated in FIGS. 40a to 40d. As shown in FIGS. 40a and 40b, the first surgical guide 500 comprises the first guide plate 510 and the first guide locking head 520 connected to the first guide plate 510. Further, the first guide locking head 520 comprises a guide protrusion 525 which is engageable with the accommodation recess 140 of the first implant element 100. To this end, guide protrusion 525 has a shape that is complementary to the shape of the accommodation recess 140 of the first implant element 100. The first guide plate 510 comprises one or more first guide apertures 515 which extend entirely through the first guide plate 510. In the embodiment shown in FIGS. 40a to 40d, the first guide plate 510 comprises two first guide apertures, but the first surgical guide 500 according to the present invention is not limited thereto and may comprise more or less first guide apertures. In FIGS. 40c and 40d, the first surgical guide 500 is engaged with the first implant element 100, which comprises the first stem portion 180 having first stem through-holes 183. Specifically, the guide protrusion 525 is engaged with the accommodation recess of the first implant element 100. As can be seen from FIGS. 40c and 40d, the first guide apertures 515 are disposed in the first guide plate 510 such that they match with pre-determined positions of one or more first stem through-holes 183 on the first stem portion 180, respectively, when the guide protrusion 525 is engaged with the accommodation recess 140 of the first implant element 100. Thus, the first guide apertures 515 of the first surgical guide 500 aid the surgeon to drill holes in precise alignment with the first stem through-holes 183 of the first stem portion 180 through the cortical bone. This is then followed by inserting stem fixation screws through the drilled holes into the first stem through-holes 183 of the stem portion 180.

An exemplary embodiment of the second surgical guide 550 according to the present invention is schematically illustrated in FIGS. 41a to 41d. Similar to the first surgical guide 500, the second surgical guide 550 comprises the second guide plate 560 and the second guide locking head 570 connected to the second guide plate 560. As can be seen from FIG. 40b, the second guide plate 560 may be slightly elevated (e.g. about 1.5 mm) with regard to the second guide locking head 570. As shown in FIGS, the first guide locking head 570 comprises a guide recess 575 which has a shape that is complementary to the shape of the protrusion 240 of the second implant element 200 to be engageable with the protrusion 240 of the second implant element 200. The second guide plate 560 comprises one or more second guide apertures 565 which extend entirely through the second guide plate 560. In the embodiment shown in FIGS. 41a to 41d, the second guide plate 560 comprises two second guide apertures, but the second surgical guide 550 according to the present invention is not limited thereto and may comprise more or less second guide apertures. In FIGS. 40c and 40d, the second surgical guide 550 is engaged with the second implant element 200, which comprises the second stem portion 280 having second stem through-holes 283. Specifically, the guide recess 575 is engaged with the protrusion 240 of the second implant element 200. The second guide apertures 565 are disposed in the second guide plate 560 such that they match with pre-determined positions of one or more second stem through-holes 283 on the second stem portion 280, respectively, when the guide recess 575 is engaged with the protrusion 240 of the second implant element 200 (see specifically FIGS. 41c and 41d). Similar to the first surgical guide 500, the second guide apertures 565 of the second surgical guide 550 therefore provide an aid for the surgeon when the surgeon has to drill holes in precise alignment with the second stem through-holes 283 of the second stem portion 280 through the cortical bone in order to subsequently insert stem fixation screws through the drilled holes into the second stem through-holes 283 of the stem portion 280.

Both, the first and the second surgical guides 500 and 550 may, e.g., be made from a metal material.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A mandible endoprosthesis implant, comprising:

a first implant element which extends along a first element x-axis and which includes a first coupling portion which comprises an accommodation recess which extends along the first element x-axis, and a first insertion hole which extends along a first element z-axis transverse to the first element x-axis;

a second implant element which extends along a second element x-axis and which includes a second coupling portion which comprises a protrusion which extends along the second element x-axis, and a second insertion hole which extends through the protrusion along a second element z-axis transverse to the second element x-axis, wherein the protrusion and the accommodation recess are engageable with each other such that the first and second insertion holes are at least substantially aligned with each other, thereby establishing a coupled condition between the first and second implant elements; and a fastener which, when the protrusion and the accommodation recess are engaged with each other to have the first and second insertion holes at least substantially aligned with each other, is engageable into both the first and second insertion holes so as to extend along the first element z-axis and in order to maintain the coupled condition of the first and second implant elements, and which is fixedly attachable to the first coupling portion, wherein, when the first and second implant elements are in their coupled condition and when the fastener is fixedly attached to the first coupling portion, there is provided a first abutment clearance between the first coupling portion and the second coupling portion and there is provided a second abutment clearance between the fastener and the second coupling portion, and the first and second abutment clearances are provided such that the first and second implant elements are pivotable relatively to each other about at least one of the first element z-axis and a first element y-axis, which extends transverse to the first element x- and z-axes, by a maximum angle in a range from 0.01 to 10°, (A) wherein the first implant element further comprises an elongated first stem portion which extends along the first element x-axis and which is to be inserted into a first bone portion of a patient's mandible in order to fixedly attach the first implant element to said first bone portion, wherein the first stem portion is provided with an outer thread, wherein the mandible endoprosthesis implant includes at least one of the following:

(i) the first stem portion comprises one or more first stem through-holes which extend through the first stem portion in a direction at least substantially parallel to the first element y-axis, and which are sized for accommodating a respective stem fixation screw, or (ii) the first implant element further comprising one or more threaded first plate attachment holes which extend in a direction at least substantially parallel to the first element y-axis and which are arranged between the first coupling portion and the first stem portion and which are sized to accommodate a respective plate attachment screw for attaching a respective implant fixation plate thereto, or (iii) the first implant element further comprising one or more first bone screw through-holes which extend therethrough in a direction transverse to the first element z- and y-axes and which are sized for accommodating a respective bone screw, or (B) wherein the second implant element further comprises an elongated second stem portion which extends along the second element x-axis and which is to be inserted into a second bone portion of a patient's mandible in order to fixedly attach the second implant element to said second bone portion, wherein the second stem portion is provided with an outer thread, wherein the mandible endoprosthesis implant includes at least one of the following:

(i) the second stem portion comprises one or more second stem through-holes which extend through the second stem portion in a direction, which is at least substantially parallel to a second element y-axis which is transverse to the second element x- and z-axes, and which are sized for accommodating a respective stem fixation screw, (ii) the second implant element further comprising one or more second threaded plate attachment holes which extend in a direction, which is at least substantially parallel to a second element y-axis which is transverse to the second element x- and z-axes, and which are arranged between the second coupling portion and the second stem portion and which are sized to accommodate a respective plate attachment screw for attaching a respective implant fixation plate thereto, or (iii) the second implant element further comprising one or more second bone screw through-holes which extend therethrough in a direction, which is transverse to the second element z-axis and to a second element y-axis which is transverse to the second element x- and z-axes, and which is sized for accommodating a respective bone screw.

2. The mandible endoprosthesis implant according to claim 1, wherein the first abutment clearance comprises:

a first abutment sub-clearance provided between the protrusion and the accommodation recess, and related to a relative pivoting between the first and second implant elements about the first element z-axis;

a second abutment sub-clearance provided between the protrusion and the accommodation recess, and related to relative pivoting between the first and second implant elements about the first element y-axis;

a third abutment sub-clearance provided between a first end face, in which the accommodation recess is provided, of the first coupling portion and a corresponding second end face, from which the protrusion extends, of the second coupling portion, and related to relative pivoting between the first and second implant elements about the first element z-axis; and a fourth abutment sub-clearance provided between the first end face of the first coupling portion and the corresponding second end face of the second coupling portion, and related to a relative pivoting between the first and second implant elements about the first element y-axis.

3. The mandible endoprosthesis implant according to claim 1,
wherein the protrusion and the accommodation recess are engageable with each other in a form-fit manner.

4. The mandible endoprosthesis implant according to claim 1,
wherein the protrusion and the accommodation recess are engageable with each other to form a joint which is configured to allow the first and second coupling portions to pivot about only one or about at least one or about both of the first element y- and z-axes.

5. The mandible endoprosthesis implant according to claim 1,
wherein the accommodation recess comprises a hollow cylindrical portion having a first longitudinal cylinder axis which extends along the first element y-axis and having a diameter, and comprises a hollow channel portion extending parallel to the longitudinal cylinder axis and connecting the hollow cylindrical portion to an exterior and having a channel width dimension which is smaller than the diameter of the hollow cylindrical portion,
wherein the protrusion comprises an at least substantially cylindrical head portion having a second longitudinal cylinder axis and having a diameter matching the diameter of the hollow cylindrical portion, and an elongated neck portion extending parallel to the second longitudinal cylinder axis and having a neck width dimension matching the channel width dimension and connecting the head portion with a remainder of the second implant element, whereby the protrusion is insertable into the accommodation recess along the first element y-axis, with its head and neck portions engaging the hollow cylindrical and hollow channel portions, respectively, thereby establishing the coupled condition between the first and second implant elements.

6. The mandible endoprosthesis implant according to claim 5, wherein cylinder end faces of the head portion have a chamfered circumferential edge, and wherein the neck portion, on its longitudinal ends, respectively has upper and lower chamfered edges smoothly transitioning into the corresponding chamfered circumferential edge.

7. The mandible endoprosthesis implant according to claim 1,
wherein the fastener is a screw which can be tightly screwed into an inner thread formed within the first insertion hole to thereby fixedly attach the fastener to the first coupling portion,
wherein the screw has a countersunk head, and
wherein the first insertion hole comprises a complementary countersunk hole portion to receive the countersunk head in a flush manner.

8. The mandible endoprosthesis implant according to claim 1, wherein the first insertion hole has a first passage and a second passage which are formed in the first coupling portion on opposite sides of the accommodation recess so that, in the coupled condition of the first and second implant elements, the second insertion hole is arranged between the first and second passages in a sandwiched manner,
wherein the fastener is a screw having a head and a threaded shaft, wherein the threaded shaft can be tightly screwed into an inner thread formed within the second passage to fixedly attach the fastener to the first coupling portion with the head supported against the first coupling portion at a position proximal to the first passage and distal to the second passage.

9. The mandible endoprosthesis implant according to claim 1, wherein (i) when the first implant element further comprises the elongated first stem portion:
the second implant element is formed in one piece with a further first implant element,
wherein an accommodation recess of the further first implant element and the protrusion of the of the second implant element are oppositely arranged,
wherein the x-axes of the second and further first implant elements are at least substantially aligned with each other,
wherein the first implant element is coupled to the second implant element and a further second implant element is coupled to the further first implant element,
or wherein (ii) when the first implant element further comprises the elongated first stem portion:
the second implant element is formed in one piece with a further second implant element,
wherein the protrusion of the further second implant element and the protrusion of the second implant element are oppositely arranged,
wherein the x-axes of the second and further second implant elements are at least substantially aligned with each other,
wherein the first implant element is coupled to the second implant element and a further second implant element is coupled to the further second implant element.

10. The mandible endoprosthesis implant according to claim 1, wherein (i) when the second implant element further comprises the elongated second stem portion:
the first implant element is formed in one piece with a further first implant element,
wherein an accommodation recess of the further first implant element and the accommodation recess of the of the first implant element are oppositely arranged,
wherein the x-axes of the first and further first implant elements are at least substantially aligned with each other,
wherein the first implant element is coupled to the second implant element and a further
second implant element is coupled to the further first implant element,
or wherein (ii) when the second implant element further comprises the elongated second stem portion:
the first implant element is formed in one piece with a further second implant element,
wherein the protrusion of the further second implant element and the accommodation recess of the of the first implant element are oppositely arranged,
wherein the x-axes of the first and further second implant elements are at least substantially aligned with each other,
wherein further the first implant element is coupled to the second implant element and a further first implant element is coupled to the further second implant element.

11. The mandible endoprosthesis implant according to claim 1, wherein when the second implant element further comprises the elongated second stem portion,
the first implant element further comprising a curved shaft portion which is formed in a shape that corresponds to a ramus region, which is to be replaced by the first implant element, of a patient's mandible,
wherein the shaft portion further comprising a joint head which is shaped so that it can engage with the natural articular disk and fossa of a temporomandibular joint of the patient.

12. The mandible endoprosthesis implant according to claim 1, wherein when the first implant element further comprises the elongated first stem portion,
the second implant element further comprising a curved shaft portion which is formed in a shape that corresponds to a ramus region, which is to be replaced by the second implant element, of a patient's mandible,
wherein the shaft portion further comprising a joint head which is shaped so that it can engage with the natural articular disk and fossa of a temporomandibular joint of the patient.

13. A mandible endoprosthesis implant system, comprising:
a first mandible endoprosthesis implant or a second mandible endoprosthesis implant;
the first mandible endoprosthesis implant comprising:
a first implant element which extends along a first element x-axis and which includes a first coupling portion which comprises an accommodation recess which extends along the first element x-axis, and a first insertion hole which extends along a first element z-axis transverse to the first element x-axis;
a second implant element which extends along a second element x-axis and which includes a second coupling portion which comprises a protrusion which extends along the second element x-axis, and a second insertion hole which extends through the protrusion along a second element z-axis transverse to the second element x-axis, wherein the protrusion and the accommodation recess are engageable with each other such that the first and second insertion holes are at least substantially aligned with each other, thereby establishing a coupled condition between the first and second implant elements; and
a fastener which, when the protrusion and the accommodation recess are engaged with each other to have the first and second insertion holes at least substantially aligned with each other, is engageable into both the first and second insertion holes so as to extend along the first element z-axis and in order to maintain the coupled condition of the first and second implant elements, and which is fixedly attachable to the first coupling portion,
wherein, when the first and second implant elements are in their coupled condition and when the fastener is fixedly attached to the first coupling portion, there is provided a first abutment clearance between the first coupling portion and the second coupling portion and there is provided a second abutment clearance between the fastener and the second coupling portion, and the first and second abutment clearances are provided such that the first and second implant elements are pivotable relatively to each other about at least one of the first element z-axis and a first element y-axis, which extends transverse to the first element x- and z-axes, by a maximum angle in a range from 0.01 to 10°;
wherein the first implant element further comprises an elongated first stem portion which extends along the first element x-axis and which is to be inserted into a first bone portion of a patient's mandible in order to fixedly attach the first implant element to said first bone portion,
wherein the first stem portion is provided with an outer thread,
the first implant element further comprising one or more threaded first plate attachment holes which extend in a direction at least substantially parallel to the first element y-axis and which are arranged between the first coupling portion and the first stem portion and which are sized to accommodate a respective plate attachment screw for attaching a respective implant fixation plate thereto;
the second mandible endoprosthesis implant comprising:
a first implant element which extends along a first element x-axis and which includes a first coupling portion which comprises an accommodation recess which extends along the first element x-axis, and a first insertion hole which extends along a first element z-axis transverse to the first element x-axis;
a second implant element which extends along a second element x-axis and which includes a second coupling portion which comprises a protrusion which extends along the second element x-axis, and a second insertion hole which extends through the protrusion along a second element z-axis transverse to the second element x-axis, wherein the protrusion and the accommodation recess are engageable with each other such that the first and second insertion holes are at least substantially aligned with each other, thereby establishing a coupled condition between the first and second implant elements; and
a fastener which, when the protrusion and the accommodation recess are engaged with each other to have the first and second insertion holes at least substantially aligned with each other, is engageable into both the first and second insertion holes so as to extend along the first element z-axis and in order to maintain the coupled condition of the first and second implant elements, and which is fixedly attachable to the first coupling portion,
wherein, when the first and second implant elements are in their coupled condition and when the fastener is fixedly attached to the first coupling portion, there is provided a first abutment clearance between the first coupling portion and the second coupling portion and there is provided a second abutment clearance between the fastener and the second coupling portion, and the first and second abutment clearances are provided such that the first and second implant elements are pivotable relatively to each other about at least one of the first element z-axis and a first element y-axis, which extends transverse to the first element x- and z-axes, by a maximum angle in a range from 0.01 to 10°;
wherein the second implant element further comprises an elongated second stem portion which extends along the second element x-axis and which is to be inserted into a second bone portion of a patient's mandible in order to fixedly attach the second implant element to said second bone portion,
wherein the second stem portion is provided with an outer thread,
the second implant element further comprising one or more second threaded plate attachment holes which extend in a direction, which is at least substantially parallel to a second element y-axis which is transverse to the second element x- and z-axes, and which are arranged between the second coupling portion and the second stem portion and which are sized to accommodate a respective plate attachment screw for attaching a respective implant fixation plate thereto;

one or more implant fixation plates, having at least a first and a second screw insertion through-hole, the implant fixation plates being plastically deformable;
one or more plate attachment screws;
one or more bone screws;
wherein for the first mandible endoprosthesis implant:
the respective implant fixation plate is attachable to the first implant element by the respective plate attachment screw passing through the first screw insertion through-hole and engaging the respective first plate attachment hole, and is attachable to the first bone portion of the patient's mandible by the respective bone screw passing through the second screw insertion through-hole and engaging the first bone portion of the patient's mandible,
wherein for the second mandible endoprosthesis implant:
the respective implant fixation plate is attachable to the second implant element by the respective plate attachment screw passing through the first screw insertion through-hole and engaging the respective second plate attachment hole, and is attachable to the second bone portion of the patient's mandible by the respective bone screw passing through the second screw insertion through-hole and engaging the second bone portion of the patient's mandible.

14. The mandible endoprosthesis implant system according to claim 13,
wherein for the first mandible endoprosthesis implant, the one or more implant fixation plates are elongated and have a length which is at maximum the length of the first implant element along the first element x-axis, or
wherein for the second mandible endoprosthesis implant, the one or more implant fixation plates are elongated and have a length which is at maximum the length of the second implant element along the second element x-axis.

15. The mandible endoprosthesis implant system according to claim 13,
the system further including one or more elongated bone fixation plates having first and second longitudinal plate ends, each provided with a respective bone fixation through-hole for being passed by a respective one of the one or more bone screw,
wherein the one or more bone fixation plates are each longer than each of the one or more implant fixation plates.

16. A surgical kit, comprising:
a plurality of mandible endoprosthesis implants, each of the plurality of mandible endoprosthesis implants comprising:
a first implant element which extends along a first element x-axis and which includes a first coupling portion which comprises an accommodation recess which extends along the first element x-axis, and a first insertion hole which extends along a first element z-axis transverse to the first element x-axis;
a second implant element which extends along a second element x-axis and which includes a second coupling portion which comprises a protrusion which extends along the second element x-axis, and a second insertion hole which extends through the protrusion along a second element z-axis transverse to the second element x-axis, wherein the protrusion and the accommodation recess are engageable with each other such that the first and second insertion holes are at least substantially aligned with each other, thereby establishing a coupled condition between the first and second implant elements; and
a fastener which, when the protrusion and the accommodation recess are engaged with each other to have the first and second insertion holes at least substantially aligned with each other, is engageable into both the first and second insertion holes so as to extend along the first element z-axis and in order to maintain the coupled condition of the first and second implant elements, and which is fixedly attachable to the first coupling portion,
wherein, when the first and second implant elements are in their coupled condition and when the fastener is fixedly attached to the first coupling portion, there is provided a first abutment clearance between the first coupling portion and the second coupling portion and there is provided a second abutment clearance between the fastener and the second coupling portion, and the first and second abutment clearances are provided such that the first and second implant elements are pivotable relatively to each other about at least one of the first element z-axis and a first element y-axis, which extends transverse to the first element x- and z-axes, by a maximum angle in a range from 0.01 to 10°,
wherein the surgical kit further comprises:
(i) a first locking device and a first implant element mount which comprises a first end and a second end,
wherein the first end of the first implant element mount is attachable to a hand tool; and
wherein the second end of the first implant element mount comprises a mount protrusion which is engageable with the accommodation recess of the first implant element, thereby establishing a coupled condition between the first implant element mount and the first implant element,
and wherein the first locking device is engageable with the first implant element mount and is engageable with the first implant element to lock the first implant element and the first implant element mount together,
and/or the surgical kit further comprises:
(ii) a second locking device and a second implant element mount which comprises a first end and a second end;
wherein the first end of the second implant element mount is attachable to a hand tool; and
wherein the second end of the second implant element mount comprises a mount recess which is engageable with the protrusion of the second implant element, thereby establishing a coupled condition between the second implant element mount and the second implant element; and
wherein the second locking device is engageable with the second implant element and engageable with the second implant element mount to lock the second implant element and the second implant element mount together.

17. The surgical kit according to claim 16, further comprising:
a hand tool which comprises a mount attachment portion for attaching the first end of a respective implant element mount thereto, and comprises a grip portion to be gripped by a surgeon,
wherein the hand tool is configured to rotate the respective implant element mount when the respective implant element mount is attached to the mount attachment portion of the hand tool.

18. The surgical kit according to claim 16, further comprising:
- (i) a first surgical guide which comprises a first guide plate and a first guide locking head connected to the first guide plate,
- wherein the first guide locking head comprises a guide protrusion which is engageable with the accommodation recess of the first implant element; and
- wherein the first guide plate comprises one or more first guide apertures which are matchable with positions of one or more first stem through-holes on the first stem portion, respectively, by engaging the guide protrusion with the accommodation recess of the first implant element and/or further comprising:
- (ii) a second surgical guide which comprises a second guide plate and a second guide locking head connected to the second guide plate,
- wherein the second guide locking head comprises a guide recess which is engageable with the protrusion of the second implant element; and
- wherein the second guide plate comprises one or more second guide apertures which are matchable with positions of one or more second stem through-holes on the second stem portion, respectively, by engaging the guide recess with the protrusion of the second implant element.

\* \* \* \* \*